US012594308B2

(12) United States Patent
    Nigro

(10) Patent No.: US 12,594,308 B2
(45) Date of Patent: Apr. 7, 2026

(54) METHODS OF PREPARING A POSTBIOTIC COMPOSITION

(71) Applicant: SCIENCE POWER SRL, Milan (IT)

(72) Inventor: Federica Nigro, Naples (IT)

(73) Assignee: SCIENCE POWER SRL, Milan (IT)

( * ) Notice: Subject to any disclaimer, the term of this patent is extended or adjusted under 35 U.S.C. 154(b) by 0 days.

(21) Appl. No.: 18/909,568

(22) Filed: Oct. 8, 2024

(65) Prior Publication Data

US 2025/0114409 A1 Apr. 10, 2025

Related U.S. Application Data

(60) Provisional application No. 63/688,678, filed on Aug. 29, 2024, provisional application No. 63/677,259, filed on Jul. 30, 2024, provisional application No. 63/667,555, filed on Jul. 3, 2024, provisional application No. 63/665,111, filed on Jun. 27, 2024, provisional application No. 63/651,254, filed on May 23, 2024.

(30) Foreign Application Priority Data

Oct. 9, 2023 (IT) ........................ 102023000020844

(51) Int. Cl.

| A61K 35/74 | (2015.01) |
| A61K 36/064 | (2006.01) |
| A61K 47/12 | (2006.01) |
| A61P 1/00 | (2006.01) |
| C12N 1/18 | (2006.01) |
| C12N 1/20 | (2006.01) |
| C12N 1/36 | (2006.01) |

(52) U.S. Cl.
CPC ............ *A61K 35/74* (2013.01); *A61K 36/064* (2013.01); *A61K 47/12* (2013.01); *A61P 1/00* (2018.01); *C12N 1/18* (2013.01); *C12N 1/20* (2013.01); *C12N 1/36* (2013.01)

(58) Field of Classification Search
CPC ...... A61K 35/74; A61K 36/064; A61K 47/12; A61P 1/00; C12N 1/18; C12N 1/20; C12N 1/36
See application file for complete search history.

(56) References Cited

U.S. PATENT DOCUMENTS

| 9,408,818 B2 | 8/2016 | McMahon et al. |
| 9,408,819 B2 | 8/2016 | Herz et al. |
| 2009/0317892 A1 | 12/2009 | Miura et al. |
| 2016/0029666 A1 | 2/2016 | Carpenter et al. |
| 2023/0067393 A1* | 3/2023 | Huchette-Defretin ...................... A23L 33/185 |
| 2023/0157344 A1 | 5/2023 | Seidensticker et al. |
| 2024/0180978 A1 | 6/2024 | Speckmann et al. |

FOREIGN PATENT DOCUMENTS

| BR | 102017025878 A2 | 6/2019 |
| CN | 113575722 A | 11/2021 |
| CN | 115305191 A | 11/2022 |
| CN | 116138462 A | 5/2023 |
| CN | 116515909 A | 8/2023 |
| CN | 118252248 A | 6/2024 |
| GB | 2625740 A | 7/2024 |
| KR | 102149102 B1 | 8/2020 |
| WO | WO-2025078948 A2 | 4/2025 |

OTHER PUBLICATIONS

Salminen et al (2021, Date Published: Sep. 2021, Gastroenterology & Hepatology, https://doi.org/10.1038/s41575-021-00440-6, cited on IDS filed Oct. 8, 2024) {herein Salminen }. (Year: 2021).*

WebMD et al (Date Published 2022, Lacticaseibacillus Paracasei, https://www.webmd.com/vitamins/ai/ingredientmono-1668/lacticaseibacillus-paracasei, examiner cited) {herein WebMD). (Year: 2022).*

Shu et al (2022, Original Article, examiner cited) {herein Shu}. (Year: 2022).*

Gurunathan et al (Date Published: Dec. 26, 2023, foods, examiner cited) {herein Gurunathan}. (Year: 2023).*

Chen et al (Date Published: Jan. 23, 2023, Ffermentation, examiner cited ) {herein Chen} (Year: 2023).*

Salminen et al (Date Published: Sep. 2021, Gastroenterology & Hepatology, cited on IDS filed Oct. 8, 2024) {herein Salminen} (Year: 2021).*

Bueno et al (Date Published: 2025, Fermentation, Examiner cited) (Year: 2025).*

Bengoa, A.A., et al., "Health-promoting Properties of Lacticaseibacillus Paracasei: a Focus on Kefir Isolates and Exopolysaccharide-producing Strains," Foods 10(10):2239, MDPI AG, Switzerland (Sep. 2021).

Brunner, J., et al., "Target Specific Tight Junction Modulators," Advanced Drug Delivery Reviews 171:266-288, Elsevier Science Publishers, Netherlands (Apr. 2021).

Canani, R.B., et al., "Potential Beneficial Effects of Butyrate in Intestinal and Extraintestinal Diseases," World Journal of Gastroenterology 17(12):1519-1528, Baishideng Publishing Group, United States (Mar. 2011).

Cervantes-Barragan, L., et al., "Lactobacillus Reuteri Induces Gut Intraepithelial CD4+CD8αα+ T Cells," Science 357(6353):806-810, American Association for the Advancement of Science, United States (Aug. 2017).

Da, M., et al., "Postbiotics: Enhancing Human Health With a Novel Concept," eFOOD 5:e180, Wiley, United States (Aug. 2024).

(Continued)

*Primary Examiner* — Manjunath N Rao
*Assistant Examiner* — Erica Nicole Jones-Foster
(74) *Attorney, Agent, or Firm* — STERNE, KESSLER, GOLDSTEIN & FOX P.L.L.C.

(57) ABSTRACT

The disclosure provides methods of preparing a postbiotic composition comprising multiple (i.e., two or more) separate microbial fermentations, which may be performed in parallel or sequential steps.

15 Claims, 32 Drawing Sheets

(56)        References Cited

OTHER PUBLICATIONS

Danladi, Y., et al., "Effects of Postbiotics and Paraprobiotics as Replacements for Antibiotics on Growth Performance, Carcass Characteristics, Small Intestine Histomorphology, Immune Status and Hepatic Growth Gene Expression in Broiler Chickens," Animals 12(7):917, Molecular Diversity Preservation International, Switzerland (Apr. 2022).

De Castro, C., et al., "Microbe-associated Molecular Patterns in Innate Immunity: Extraction and Chemical Analysis of Gram-negative Bacterial Lipopolysaccharides," Methods in Enzymology 480:89-115, Academic Press, United States (Jan. 2010).

De Filippis, F., et al., "Specific Gut Microbiome Signatures and the Associated Pro-inflammatory Functions Are Linked to Pediatric Allergy and Acquisition of Immune Tolerance," Nature Communications 12(1):5958, 1-11, Nature Publishing Group, United Kingdom (Oct. 2021).

Dodd, D., et al., "A Gut Bacterial Pathway Metabolizes Aromatic Amino Acids Into Nine Circulating Metabolites," Nature 551(7682):648-652, Nature Publishing Group, United Kingdom (Nov. 2017).

Fang, L., et al., "Effects of Mixed Fermentation of Different Lactic Acid Bacteria and Yeast on Phytic Acid Degradation and Flavor Compounds in Sourdough," LWT 174:114438, pp. 1-16, Elsevier, Netherlands (Jan. 2023).

Hill, C., et al., "Expert Consensus Document. The International Scientific Association for Probiotics and Prebiotics Consensus Statement on the Scope and Appropriate Use of the Term Probiotic," Nature Reviews. Gastroenterology & Hepatology 11(8):506-514, Nature Publishing Group, United Kingdom (Aug. 2014).

Italian Search Report and Written Opinion for IT202300020844, Italian Patent Office, Munich, Germany, mailed on Mar. 27, 2024, 12 pages.

Kiousi, D.E., et al., "Genomic Insight Into Lacticaseibacillus Paracasei SP5, Reveals Genes and Gene Clusters of Probiotic Interest and Biotechnological Potential," Frontiers in Microbiology 13:922689, Frontiers Research Foundation, Switzerland (Jun. 2022).

Krishnan, S., et al., "Gut Microbiota-derived Tryptophan Metabolites Modulate Inflammatory Response in Hepatocytes and Macrophages," Cell Reports 23(4):1099-1111, Cell Press, United States (Apr. 2018).

Lamas, B., et al., "CARD9 Impacts Colitis by Altering Gut Microbiota Metabolism of Tryptophan Into Aryl Hydrocarbon Receptor Ligands," Nature Medicine 22(6):598-605, Nature Publishing Company, United States (Jun. 2016).

Liu, W., et al., "Adjustment of Impact Phenolic Compounds, Antioxidant Activity and Aroma Profile in Cabernet Sauvignon Wine by Mixed Fermentation of Pichia Kudriavzevii and *Saccharomyces cerevisiae*," Food chemistry: X, 18:100685, Elsevier, Netherlands (Apr. 2023).

Ogyu, K., et al., "Kynurenine Pathway in Depression: a Systematic Review and Meta-analysis," Neuroscience and Biobehavioral Reviews 90:16-25, Pergamon Press, United States (Jul. 2018).

Osadchiy, V., et al., "Correlation of Tryptophan Metabolites With Connectivity of Extended Central Reward Network in Healthy Subjects," PLoS one 13(8):e0201772, Public Library of Science, United States (Aug. 2018).

Paparo, L., et al., "Direct Effects of Fermented Cow's Milk Product With Lactobacillus Paracasei Cba L74 on Human Enterocytes," Beneficial Microbes 9(1):165-172, Wageningen Academic Publishers, Netherlands (Jan. 2018).

Pimentel, T.C., et al., "Postbiotics: an Overview of Concepts, Inactivation Technologies, Health Effects, and Driver Trends," Trends in Food Science & Technology 138:199-214, Elsevier, Netherlands (Aug. 2023).

Qi, H., et al., "Lactobacillus Maintains Healthy Gut Mucosa by Producing L-ornithine," Communications Biology 2:171, Nature Publishing Group UK, United Kingdom (May 2019).

Ridyard, K.E., and Overhage, J., "The Potential of Human Peptide LL-37 as an Antimicrobial and Anti-biofilm Agent," Antibiotics 10(6):650, MDPI AG, Switzerland (May 2021).

Salminen, S., et al., "The International Scientific Association of Probiotics and Prebiotics (ISAPP) Consensus Statement on the Definition and Scope of Postbiotics," Nature Reviews. Gastroenterology & Hepatology 18(9):649-667, Nature Publishing Group, United Kingdom (Sep. 2021).

Speciale, I., et al., "Liquid-state NMR spectroscopy for complex carbohydrate structural analysis: A hitchhiker's guide," Carbohydrate Polymers 277:118885, Elsevier Applied Science Publishers, United Kingdom (Feb. 2022).

Venkatesh, M., et al., "Symbiotic Bacterial Metabolites Regulate Gastrointestinal Barrier Function via the Xenobiotic Sensor PXR and Toll-like Receptor 4," Immunity 41(2):296-310, Cell Press, United States (Aug. 2014).

Vinogradov, E., et al., "Structural Investigation of Cell Wall Polysaccharides of *Lactobacillus delbrueckii* Subsp. *bulgaricus* 17," Carbohydrate Research 413:93-99, Elsevier, Netherlands (Sep. 2015).

Vittoria, M., et al., "Probiotics as an Alternative to Antibiotics: Genomic and Physiological Characterization of Aerobic Spore Formers From the Human Intestine," Microorganisms 11(8):1978, MDPI AG, Switzerland (Jul. 2023).

Invitation to Pay Additional Fees for International Application No. PCT/IB2024/059839, European Patent Office, Netherlands, mailed on Jan. 30, 2025, 20 pages.

International Search Report and Written Opinion for International Application No. PCT/IB2024/059839, European Patent Office, Netherlands, mailed on Apr. 7, 2025, 33 pages.

* cited by examiner

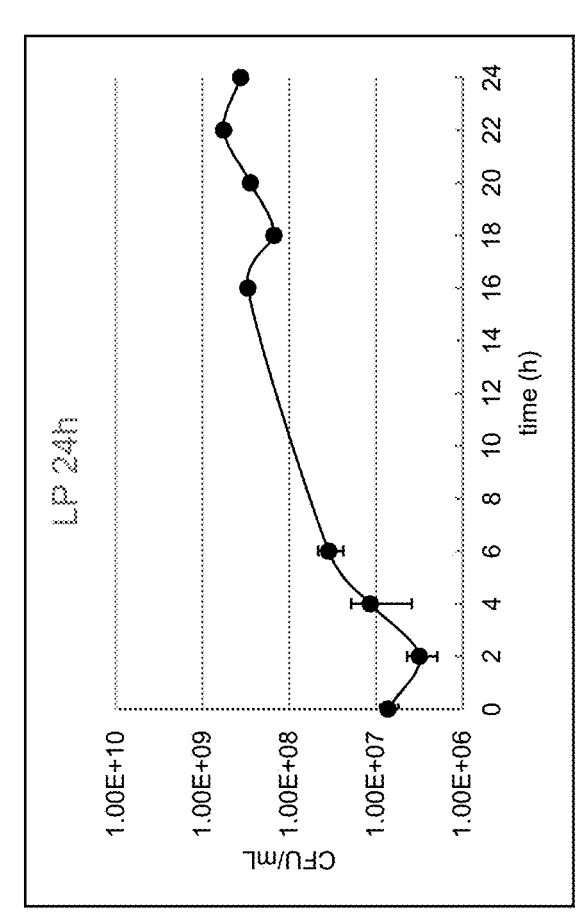
Figure 4A
Figure 4B

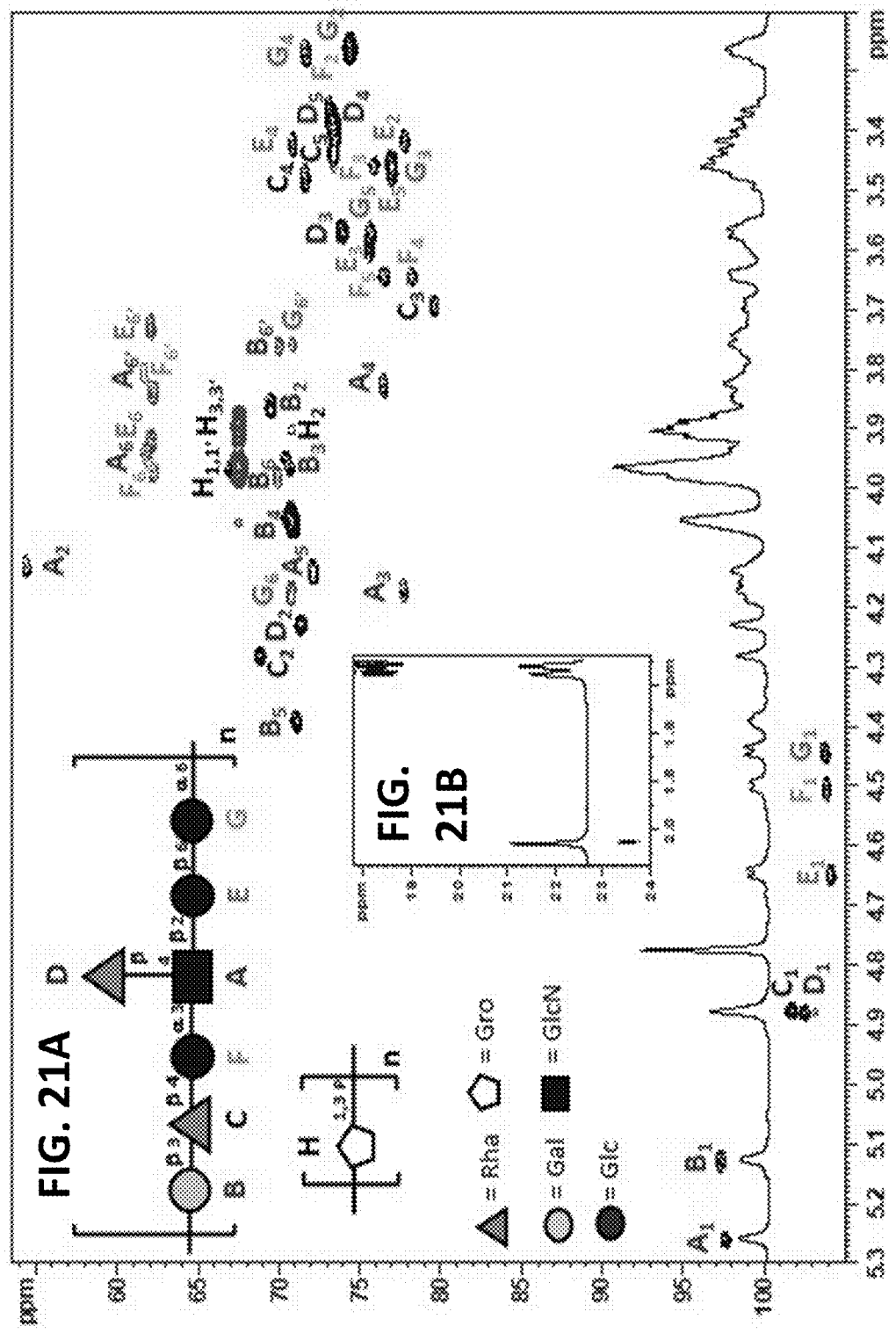

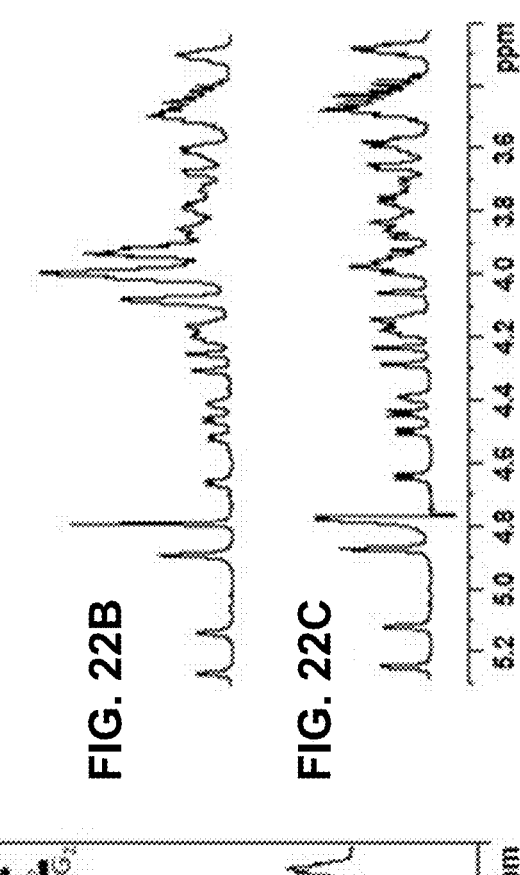
FIG. 22B
FIG. 22C
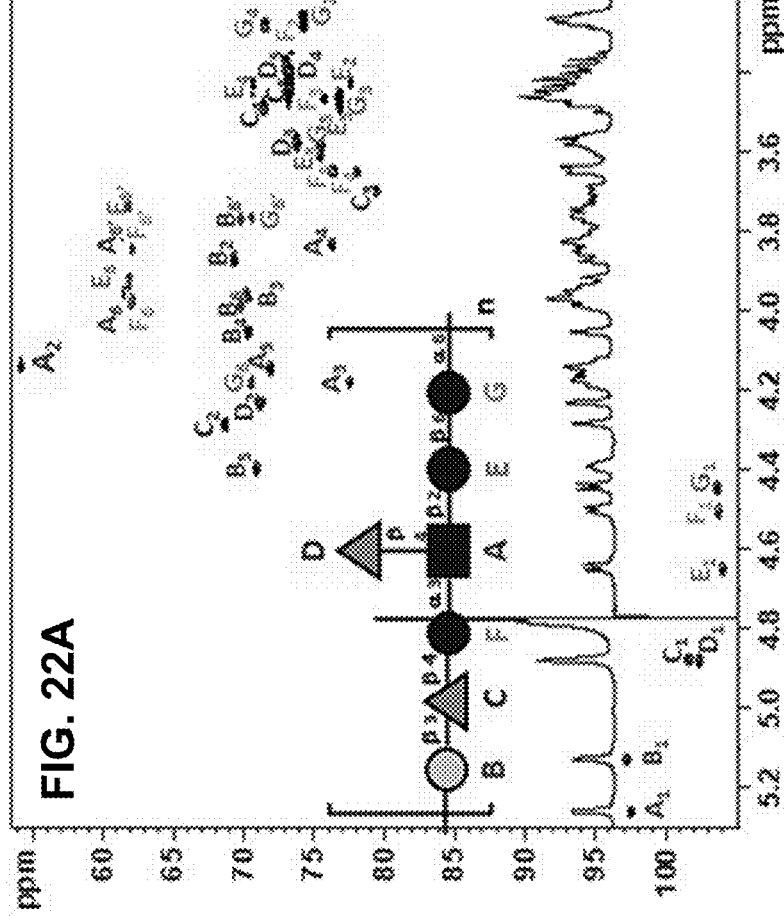
FIG. 22A

*B. velenzensis MV4*

*P. megaterium MV30*

METHODS OF PREPARING A POSTBIOTIC COMPOSITION

CROSS-REFERENCE TO RELATED APPLICATIONS

The present application claims the priority benefit of Italian Patent Application No. 102023000020844, filed Oct. 9, 2023, U.S. Provisional Patent Application No. 63/651,254, filed May 23, 2024, U.S. Provisional Patent Application No. 63/665,111, filed Jun. 27, 2024, U.S. Provisional Patent Application No. 63/667,555, filed Jul. 3, 2024, U.S. Provisional Patent Application No. 63/677,259, filed Jul. 30, 2024, and U.S. Provisional Patent Application No. 63/688,678, filed Aug. 29, 2024, each of which is incorporated by reference in its entirety.

FIELD OF THE INVENTION

The present invention pertains to methods for preparing a postbiotic composition from multiple strains of fermenting microorganisms.

BACKGROUND OF THE INVENTION

Fermentation processes are known to cause modifications to a fermented matrix, with microbiological, chemical and physical changes, as well as the potential acquisition of functionality (Handbook of Fermented Functional Foods, Second Edition-Google Books n.d.).

Probiotic products are characterized by the presence of living microorganisms that are able to confer health benefits to the host (Hill C., et al.; "The International Scientific Association for Probiotics and Prebiotics Consensus Statement on the Scope and Appropriate Use of the Term Probiotic," Nature Reviews Gastroenterology & Hepatology 2014 11(8): 506-14). However, probiotic products have poor tolerance to heat treatments and are characterized by a low stability and reduced shelf-life (Pimentel T C, et al.; 2023. "Postbiotics: An Overview of Concepts, Inactivation Technologies, Health Effects, and Driver Trends," Trends in Food Science & Technology 138:199-214).

Recently, a new concept has gained interest, based on postbiotic preparations. A postbiotic product is currently defined as "a preparation of inanimate microorganisms and/or their components that confer benefits on the health of the host". In this context, the term "preparation" is intended to mean the whole of the inactivated microbial biomass, their components (pili, cell wall components or other components), the matrix and the bacterial metabolites produced during fermentation (Salminen, S., et al. 2021, "The International Scientific Association of Probiotics and Prebiotics (ISAPP) Consensus Statement on the Definition and Scope of Postbiotics," Nature Reviews, Gastroenterology & Hepatology 18(9): 649).

The activity of a postbiotic product is linked to the specific microorganism from which it is derived as well as its fermentation substrate employed. Indeed, the substrate composition affects microorganism growth, production of metabolites and accordingly, the biological activity of the preparation.

It is known that specific fermentation matrices may significantly improve the production performance of biomass and the biological actions of postbiotics. Moreover, the growth of microorganisms and the production of functional compounds and/or metabolites is influenced by the composition of the fermentation matrix. The processes that use fermentation substrates containing prebiotics are widely known and used in the biotechnological sectors of reference.

Postbiotic products are fermented products, subsequently subjected to an inactivation process, that exert beneficial effects on the health of the subject. Such products are characterized by higher stability and prolonged shelf life, especially due to the absence of living microorganisms. Furthermore, postbiotics are a safer product in vulnerable and/or immunocompromised patients (Salminen S., et al.; 2021, "The International Scientific Association of Probiotics and Prebiotics (ISAPP) Consensus Statement on the Definition and Scope of Postbiotics," Nature Reviews, Gastroenterology & Hepatology 18(9): 649).

It is therefore an object of the present invention to provide methods that provide for the preparation of a postbiotic composition, particularly a postbiotic composition having enhanced bioactive properties.

It is another object of the present invention to provide methods for obtaining a safe postbiotic composition with high stability and long shelf-life.

SUMMARY OF THE INVENTION

In one aspect of the present invention is provided a method of preparing a postbiotic composition comprising the steps of: (i) inoculating a plurality of culture media with a plurality of fermenting microrganisms, wherein each culture medium is inoculated with a different fermenting microorganism; (ii) fermenting the inoculated plurality of culture media under conditions suitable for fermentation, thereby obtaining a plurality of fermentation products each containing a different fermenting microorganism; (iii) inactivating the fermenting microorganisms in the plurality of fermentation products to obtain a plurality of inactivated fermentation products; and (iv) mixing the plurality of inactivated fermentation products, thereby obtaining a postbiotic composition.

In another aspect of the present invention is provided a method of preparing a postbiotic composition comprising the steps of: (i) inoculating a culture medium with a first fermenting microorganism; (ii) fermenting the culture medium under conditions suitable for fermentation by the first fermenting microorganism, thereby obtaining a first fermentation product comprising the first fermenting microorganism; (iii) inactivating the first fermenting microorganism in the first fermentation product to obtain a first fermentation matrix; (iv) inoculating the first fermentation matrix with a second fermenting microorganism; (v) fermenting the first fermentation matrix under conditions suitable for fermentation by the second fermenting microorganism, thereby obtaining a second fermentation product comprising the second fermenting microorganism; (vi) inactivating the second fermenting microorganism in the second fermentation product to obtain a second fermentation matrix, thereby obtaining a postbiotic composition; and optionally repeating steps (iv) to (vi) one or more times with an additional fermenting microorganism. In some aspects, each fermenting microorganism is a different species from any other fermenting microorganism, thereby obtaining a postbiotic composition.

In some aspects, the fermenting microorganism is selected from the group consisting of a bacterial microorganism and a yeast microorganism. In some aspects, the bacterial microorganism is selected from the group consisting of a *Lactobacillus* species, a *Lactococcus* species, a *Lacticaseibacillus* species, a *Bifidobacterium* species, a *Streptococcus* species, an *Akkermansia* species, and an

3

*Escherichia* species. In some aspects, the yeast microorganism is selected from a *Saccharomyces* species.

In some aspects, the fermenting microorganism is selected from the group consisting of *Lactobacillus paracasei, Lactobacillus rhamnosus, Lactobacillus reuteri, Lactobacillus plantarum, Lactobacillus casei, Lacticaseibacillus paracasei, Bifidobacterium animalis, Bifidobacterium bifidum, Bifidobacterium infantis, Bifidobacterium breve, Bifidobacterium longum, Streptococcus salivarius, Akkermansia muciniphila, Escherichia coli*, and *Saccharomyces boulardii*. In some aspects, the *Lacticaseibacillus paracasei* is *Lacticaseibacillus paracasei* NPB01. In some aspects, the *Bifidobacterium animalis* is *Bifidobacterium animalis* subsp. *lactis*. In some aspects, the *Escherichia coli* is *Escherichia coli* Nissle 1917.

In some aspects, before inoculating with a fermenting microorganism, the inactivated fermentation product is supplemented with one or more additional ingredients.

In some aspects, the method further comprises drying the inactivated fermentation product and wherein said dried inactivated fermentation product is optionally rehydrated in water prior to subsequent inoculation with a fermenting microorganism.

In some aspects, the method further comprises the step of drying the postbiotic composition.

In some aspects, the culture medium comprises media selected from the group consisting of MRS media, Brain Heart Infusion (BHI) broth, Luria-Bertani (LB) broth, plant-derived media, functional media containing plant extracts with antioxidant, antiviral and/or antibacterial activity, culture media of natural origin, and any combination thereof. In some aspects, the Brain Heart Infusion (BHI) broth is supplemented with Porcin Gastric Mucin (PGM).

In some aspects, the fermentation step is carried out at a temperature from about 25° C. to about 45° C.

In some aspects, inactivation of the fermenting microorganism comprises a procedure selected from the group consisting of heat-inactivation, preferably at a temperature comprised between 50° C. and 100° C. for between 5 and 120 seconds, chemical treatment, gamma or ultraviolet irradiation, high pressure, sonication, and any combination thereof. In some aspects, the heat-inactivation occurs at a temperature from about 50° C. to about 100° C. for between about 5 and about 120 seconds.

Also provided herein is a postbiotic composition obtained by a method described herein, further comprising lactic acid at a concentration of about 1 g/L to about 30 g/L on the total volume of the composition and/or an amount of inactivated fermenting microorganisms of about 0.00015 g/L to about 150 g/L on the total volume of the composition. In some aspects, the amount of inactivated fermenting microorganisms comprises about $10^5$ cells/ml to about $10^{11}$ cells/ml.

Also provided herein is a postbiotic composition obtained by a method described herein, further comprising L-tryptophan or a dipeptide containing L-tryptophan. In some aspects, the composition comprises L-tryptophan at a concentration of at least about 0.01% w/w. In some aspects, the composition comprises L-tryptophan at a concentration of at least about 0.10% w/w. In some aspects, the L-tryptophan is present in an amount of at least about 10 mg, at least about 50 mg, or at least about 100 mg.

Also provided herein is a postbiotic composition obtained by a method described herein, wherein at least one of the fermenting microorganisms used to obtain the postbiotic composition is *L. paracasei* NPB01.

Also provided herein is a postbiotic composition described herein for use in the prevention or the therapeutic treatment of a disease in a subject in need thereof selected from the group consisting of infectious and inflammatory diseases, immune-mediated diseases, cancer diseases, skin disorders, gastrointestinal diseases, urogenital tract diseases, neurologic disorders, neuropsychiatric disorders, bone diseases, muscle diseases, malnutrition, metabolic diseases, and any combination thereof.

Also provided herein is a postbiotic composition described herein for use in promoting healthy aging in a mammal. Healthy aging is defined as a continuous process of optimizing opportunities to maintain and improve physical and mental health, independence, and quality of life throughout the life course.

Also provided herein is a postbiotic composition described herein for correcting drug-induced nutrient depletions in a mammal.

Also provided herein is a postbiotic composition described herein for use in improving the function of the gut barrier by increasing the expression of tight junction proteins and/or mucous proteins, and/or increasing enterocyte growth and differentiation in a subject in need thereof. In some aspects, the tight junction proteins comprise occludin and/or ZO-1. In some aspects, the mucous proteins comprise MUC5AC. In some aspects, following treatment with the postbiotic composition, the expression of occludin, ZO-1, and/or MUC5AC is increased by at least 2-fold, 3-fold, 4-fold, 5-fold, or more compared to an untreated subject. In some aspects, following treatment with the postbiotic composition, the expression of occludin, ZO-1, and/or MUC5AC is increased by at least 25%, 50%, 75% or more compared to treatment with a composition comprising a single living microorganism.

Also provided herein is a postbiotic composition described herein for use in increasing the expression of β-defensin-2 (HBD-2) in a subject in need thereof. In some aspects, following treatment with the postbiotic composition, the expression of HBD-2 is increased by at least 2-fold, 3-fold, 4-fold, 5-fold, 7-fold, 8-fold or more compared to an untreated subject. In some aspects, following treatment with the postbiotic composition, the expression of HBD-2 is at least 2-fold, 3-fold, 4-fold, or more compared to treatment with a composition comprising a single microorganism.

Also provided herein is a postbiotic composition described herein for use in increasing the expression of cathelicid LL-37 in a subject in need thereof. In some aspects, following treatment with the postbiotic composition, the expression of cathelicid LL-37 is increased by at least about 2-fold, about 3-fold, or more compared to an untreated subject.

Also provided herein is a use of a postbiotic composition described herein in a food, a beverage, a pharmaceutical, a nutraceutical, a cosmetic, or a packaging composition, and wherein the composition further comprises at least one pharmaceutically acceptable vehicle, excipient and/or diluent. In some aspects, the use is for improving the gut barrier function in a mammal. In some aspects, the use is for improving innate immune responses against infection in a mammal. In some aspects, the use is for generating a tolerogenic immune response in a mammal. In some aspects, the use is for protecting the skin against infections in a mammal.

Also provided herein is a use of a postbiotic composition described herein for increasing the total amount of one or more metabolites of L-tryptophan in a mammal. In some aspects, the one or more metabolites of L-tryptophan comprise indole-3-acetic acid, indole-3-lactic acid, and/or L-kynurenine.

Also provided herein is a use of a postbiotic composition described herein for increasing the total amount of L-tryptophan in a mammal.

Also provided herein is a use of a postbiotic composition described herein for increasing the ratio of L-tryptophan to large neutral amino acids in the plasma of a mammal.

Also provided herein is a use of a postbiotic composition described herein for increasing the biosynthesis of serotonin and/or melatonin in a mammal.

Also provided herein is a method of preventing or treating a disease selected from the group consisting of infectious and inflammatory diseases, immune-mediated diseases, cancer diseases, skin disorders, gastrointestinal diseases, urogenital tract diseases, neurologic disorders, neuropsychiatric disorders, bone diseases, muscle diseases, malnutrition, metabolic diseases, and any combination thereof, wherein the method comprises administering to a subject in need thereof a postbiotic composition described herein.

Also provided herein is a method of improving the function of the gut barrier by increasing the expression of tight junction proteins and/or mucous proteins, and/or increasing enterocyte growth and differentiation in a subject in need thereof, wherein the method comprises administering to the subject a postbiotic composition described herein. In some aspects, the tight junction proteins comprise occludin and/or ZO-1. In some aspects, the mucous proteins comprise MUC5AC. In some aspects, following treatment with the postbiotic composition, the expression of occludin, ZO-1, and/or MUC5AC is increased by at least about 2-fold, about 3-fold, about 4-fold, about 5-fold, or more compared to an untreated subject. In some aspects, following treatment with the postbiotic composition, the expression of occludin, ZO-1, and/or MUC5AC is increased by at least about 25%, about 50%, about 75% or more compared to treatment with a composition comprising a single living microorganism.

Also provided herein is a method of increasing the expression of β-defensin-2 (HBD-2) in a subject in need thereof, wherein the method comprises administering to the subject a postbiotic composition provided herein. In some aspects, following treatment with the postbiotic composition, the expression of HBD-2 is at least about 2-fold, about 3-fold, about 4-fold, about 5-fold, about 7-fold, about 8-fold or more compared to an untreated subject. In some aspects, following treatment with the postbiotic composition, the expression of HBD-2 is increased by at least about 2-fold, about 3-fold, about 4-fold, or more compared to treatment with a composition comprising a single microorganism.

Also provided herein is a method for increasing the total amount of one or more metabolites of L-tryptophan in a subject in need thereof, wherein the method comprises administering to the subject a postbiotic composition provided herein. In some aspects, the one or more metabolites of L-tryptophan comprise indole-3-acetic acid, indole-3-lactic acid, and/or L-kynurenine.

Also provided herein is a method for increasing the total amount of L-tryptophan in a subject in need thereof, wherein the method comprises administering to the subject a postbiotic composition provided herein.

Also provided herein is a method for increasing the ratio of L-tryptophan to large neutral amino acids in the plasma of a subject in need thereof, wherein the method comprises administering to the subject a postbiotic composition provided herein.

Also provided herein is a method for increasing the biosynthesis of serotonin and/or melatonin in a subject in need thereof, wherein the method comprises administering to the subject a postbiotic composition provided herein.

Also provided herein is a method for promoting healthy aging in a subject in need thereof, wherein the method comprises administering to the subject a postbiotic composition provided herein.

Also provided herein is a method for correcting correcting drug-induced nutrient depletions in a subject in need thereof, wherein the method comprises administering to the subject a postbiotic composition provided herein.

Also provided herein is a postbiotic composition produced from a multi-microorganism fermentation, wherein the multi-microorganism fermentation comprises the fermentation of two or more bacterial or yeast species. In some aspects, the postbiotic comprises two or more inactivated fermentation products. In some aspects, the multi-microorganism fermentation comprises a method described herein.

Also provided herein is a postbiotic composition comprising: (a) a first matrix comprising a first inactivated microorganism and the culture medium in which the microorganism was inactivated; and (b) one or more additional matrices each comprising an additional inactivated microorganism and the culture medium in which the microorganism was inactivated. In some aspects, the first inactivated microorganism and each additional inactivated microorganism is a different species. In some aspects, the postbiotic composition is prepared according to a method described herein.

Also provided herein is a kit comprising a postbiotic composition described herein. Also provided herein is a kit comprising a multi-microorganism fermentation matrix and an inoculum comprising two or more inactivated microorganisms. In some aspects, the postbiotic composition is prepared according to a method described herein. In some aspects, the kit further comprises documentation comprising steps and conditions for use.

BRIEF DESCRIPTION OF THE FIGURES

FIGS. 4A-4B illustrate *Lacticaseibacillus rhamnosus* (LGG)'s 24 h growth curve (FIG. 4A) and *Lacticaseibacillus paracasei* (LP)'s 24 h growth curve (FIG. 4B).

(FIG. 17B) illustrates the comparison between all the postbiotics tested belonging to Lactobacilli species.

FIGS. 21A-21B show the HSQC spectrum (600 MHZ, 298 K, $D_2O$) of the mixture of the CPS-1+TA isolated from *L. paracasei* NPB01 along with the proton NMR profile and the repeating unit structures (FIG. 21A). Letters refer to the carbohydrate residues as reported in the figure and drawn according to the symbolic nomenclature for glycans. All monosaccharides are in the pyranose form. Arabic numerals refer to the proton/carbon atoms of the respective residue. FIG. 21B shows the N-acetyl signal (2.05 ppm) of the glucosamine (residue A) plus methyl signals (1.35-1.30 ppm) of the rhamnoses units (C and D residues).

FIGS. 22A-22C show the HSQC spectrum (600 MHZ, 315 K, $D_2O$) of the CPS-1 isolated from *L. paracasei* NPB01 along with the proton profile and the structure (FIG.

22A). Letters refer to the carbohydrate residues as reported in the figure and drawn according to the symbolic nomenclature for glycans. All monosaccharides are in the pyranose form. Arabic numerals refer to the proton/carbon atoms of the respective residue. FIG. 22B shows the $^1$H NMR profile (600 MHZ, $D_2O$) of the mixture of CPS-1+TA. FIG. 22C shows the $^1$H NMR profile (600 MHz, $D_2O$) of the pure CPS-1.

FIGS. 24A-24B show the effects of *L. paracasei* NPB01 postbiotic, CPS-1, CPS-2, TA, or control (NT) on expression of LL-37 (FIG. 24A) and occludin (FIG. 24B) in Caco-2 cells. Experiments were performed in triplicates and repeated 3 times. Data were expressed as means±SD and were analysed using nonpaired t-test. *p<0.05 vs NT; ***p<0.0005 CPS-2 vs NT, vs CPS-1 vs *L. paracasei* NPB01 postbiotic; #p<0.05 TA vs *L. paracasei* NPB01 postbiotic; ##p<0.005 CPS-1 vs *L. paracasei* NPB01 postbiotic, CPS-2 vs *L. paracasei* NPB01 postbiotic.

Figures 31A, 31B, 31C:
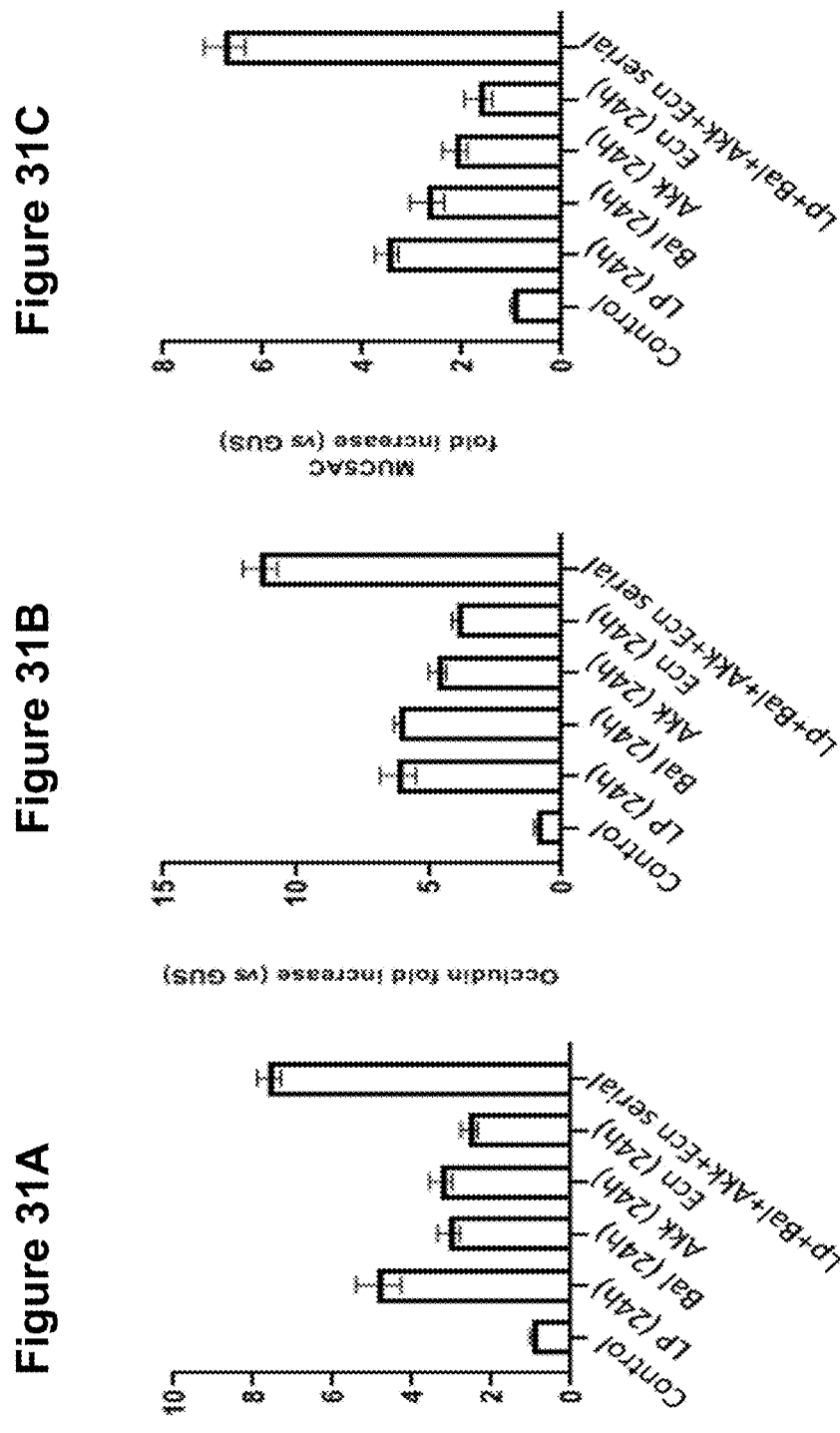
FIGS. 31A-31C show the effect of incubation with *L. paracasei* NPB-01, *B. animalis* subsp. *lactis, A. muciniphila*. and *E. coli* Nissle 1917 on the fold increase in expression of intestinal barrier integrity biomarkers (in Caco-2 cells): tight junction protein ZO-1 (FIG. 31A), tight junction protein occludin (FIG. 31B), and epithelial mucus layer protein MUC5AC (FIG. 31C).

DETAILED DESCRIPTION OF THE INVENTION

The present disclosure is directed to methods of preparing a postbiotic composition comprising multiple (i.e. two or more) separate microbial fermentations, which may be performed in parallel or sequential steps.

1. Definitions

In order that the present disclosure may be more readily understood, certain terms are first defined. As used in this application, except as otherwise expressly provided herein, each of the following terms shall have the meaning set forth below. Additional definitions are set forth throughout the application.

Before describing the present disclosure in detail, it is to be understood that this disclosure is not limited to specific compositions or process steps, as such can vary. As used in this specification and the appended claims, the singular forms "a", "an" and "the" include plural referents unless the context clearly dictates otherwise. The terms "a" (or "an"), as well as the terms "one or more," and "at least one" can be used interchangeably herein.

Furthermore, "and/or" where used herein is to be taken as specific disclosure of each of the two specified features or components with or without the other. Thus, the term and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Systeme International de Unites (SI) accepted form. Numeric ranges are inclusive of the numbers defining the range. Unless otherwise indicated, amino acid sequences are written left to right in amino to carboxy orientation. The headings provided herein are not limitations of the various aspects, which can be had by reference to the specification as a whole. Accordingly, the terms defined immediately below are more fully defined by reference to the specification in its entirety.

It is understood that wherever aspects are described herein with the language "comprising," otherwise analogous aspects described in terms of "consisting of" and/or "consisting essentially of" are also provided. As used herein, the terms "comprise" and "include" and variations thereof (e.g., "comprises," "comprising," "includes," and "including") will be understood to indicate the inclusion of a stated component, feature, element, or step or group of components, features, elements or steps but not the exclusion of any other component, feature, element, or step or group of components, features, elements, or steps. Any of the terms "comprising," "consisting essentially of," and "consisting of" may be replaced with either of the other two terms, while retaining their ordinary meanings.

The term "about" is used herein to mean approximately, roughly, around, or in the regions of. When the term "about" is used in conjunction with a numerical range, it modifies that range by extending the boundaries above and below the numerical values set forth. In general, the term "about" can modify a numerical value above and below the stated value by a variance of, e.g., 10 percent, up or down (higher or lower).

As used herein, the term "approximately," as applied to one or more values of interest, refers to a value that is similar to a stated reference value. In certain aspects, the term "approximately" refers to a range of values that fall within 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

As used herein, the terms "ug" and "uM" are used interchangeably with "µg" and "µM," respectively.

The term "probiotic" as used herein refers to live microorganisms which administered in adequate amounts are able to confer healthy effect on the host. Probiotics are discussed in, e.g., Hill, C., Guarner, F., Reid, G. et al., The International Scientific Association for Probiotics and Prebiotics consensus statement on the scope and appropriate use of the term probiotic, Nat Rev Gastroenterol Hepatol 11, 506-514 (2014).

The term "postbiotic" as used herein refers to a preparation derived from probiotic cells, after their fermentation and inactivation, composed of the same microorganisms or their components and fragments and/or their metabolites, which can confer healthy effect(s) on the host. Postbiotics are also known as "non-viable probiotics", "inactivate probiotics" or "ghost probiotics" and refer to both non-viable microbial cells and soluble factors secreted by live bacteria or released after their lysis, including various cell surface components, lactic acid, short-chain fatty acids (SCFAs) and bioactive peptides among other metabolites. The bacterial inactivation may occur, for example, by a mild heat treatment.

The term "fermentation" as used herein refers to a metabolic process by which organic molecules are broken down anaerobically.

The term "matrix" or "fermentation matrix" as used herein refers to a substrate, optionally mixed with nutrients, suitable for microbial growth and/or fermentation.

The term "multiple" as used herein means consisting of, comprising, and/or involving more than one.

"Gut barrier function" refers to the function of the intestinal epithelium to allow passage of desired nutrients through the intestinal epithelium to the rest of the body, but to prevent potentially harmful substances (e.g. antigens) from leaving the intestine.

"Immunotherapy" refers to the treatment of a subject afflicted with, or at risk of contracting or suffering a recurrence of, a disease by a method comprising inducing, enhancing, suppressing or otherwise modifying the immune system or an immune response.

As used herein, the terms "subject," "individual," or "patient," refer to any subject, particularly a mammalian subject, for whom diagnosis, prognosis, or therapy is desired. Mammalian subjects include, for example, humans, non-human primates, dogs, cats, guinea pigs, rabbits, rats, mice, horses, cattle, bears, and so on.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. The term "contacting" may include allowing two species to react, interact, or physically touch, wherein the two species may be a compound as described herein and a protein or enzyme.

"Administering" refers to the physical introduction of a composition comprising a postbiotic composition to a subject, using any of the various methods and delivery systems known to those skilled in the art. Routes of administration for the formulations disclosed herein include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In some aspects, the formulation is administered via a non-parenteral route, in some aspects, orally. Other non-parenteral routes include a topical, epidermal or mucosal route of administration, for example, intranasally, vaginally, rectally, sublingually or topically. Administering can also be performed, for example, once, a plurality of times, and/or over one or more extended periods.

"Treatment" or "therapy" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication or condition, or biochemical indicia associated with a disease.

As used herein, "effective treatment" refers to treatment producing a beneficial effect, e.g., amelioration of at least one symptom of a disease or disorder. A beneficial effect can take the form of an improvement over baseline, i.e., an improvement over a measurement or observation made prior to initiation of therapy according to the method.

The term "effective amount" refers to an amount of an agent that provides the desired biological, therapeutic, and/or prophylactic result. That result can be reduction, amelioration, palliation, lessening, delaying, and/or alleviation of one or more of the signs, symptoms, or causes of a disease, or any other desired alteration of a biological system. An effective amount can be administered in one or more administrations.

The term "combination" refers to either a fixed combination in one dosage unit form, or a combined administration where a compound of the present invention and a combination partner (e.g. another drug as explained below, also referred to as "therapeutic agent" or "co-agent") may be administered independently at the same time or separately within time intervals, especially where these time intervals allow that the combination partners show a cooperative, e.g.

synergistic effect. The single components may be packaged in a kit or separately. One or both of the components (e.g., powders or liquids) may be reconstituted or diluted to a desired dose prior to administration. The terms "co-administration" or "combined administration" or the like as utilized herein are meant to encompass administration of the selected combination partner to a single subject in need thereof (e.g. a patient), and are intended to include treatment regimens in which the agents are not necessarily administered by the same route of administration or at the same time. "Concurrently," as used herein to, refers to administration of two or more therapeutic agents, where at least part of the administration overlaps in time. Accordingly, concurrent administration includes a dosing regimen when the administration of one or more agent(s) continues after discontinuing the administration of one or more other agent(s).

A "cancer" refers a broad group of various diseases characterized by the uncontrolled growth of abnormal cells in the body. Unregulated cell division and growth results in the formation of malignant tumors that invade neighboring tissues and may also metastasize to distant parts of the body through the lymphatic system or bloodstream. A "cancer" or "cancer tissue" can include a tumor.

An "immune response" refers to the action of a cell of the immune system (for example, T lymphocytes, B lymphocytes, natural killer (NK) cells, macrophages, eosinophils, mast cells, dendritic cells and neutrophils) and soluble macromolecules produced by any of these cells or the liver (including antibodies, cytokines, and complement) that results in selective targeting, binding to, damage to, destruction of, and/or elimination from a vertebrate's body of invading pathogens, cells or tissues infected with pathogens, cancerous or other abnormal cells, or, in cases of autoimmunity or pathological inflammation, normal human cells or tissues. An immune reaction includes, e.g., activation or inhibition of a T cell, e.g., an effector T cell, a Th cell, a $CD4^+$ cell, a CD8+ T cell, or a Treg cell, or activation or inhibition of any other cell of the immune system, e.g., NK cell.

"Innate immune response" refers to the activation of one or more innate leukocytes of the innate immune system (or nonspecific immune system or in-born immunity system). The activated leukocytes of the innate immune response comprise natural killer (NK) cells, macrophages and dendritic cells. The innate immune system is distinct from the adaptive immune system (or specific immune system) which includes lymphocytes like CD4+ or CD8+ T-cells.

"Tolerogenic immune response" means any immune response that can lead to immune suppression specific to an antigen or a cell, tissue, organ, etc. that expresses such an antigen. Such immune responses include any reduction, delay or inhibition in an undesired immune response specific to the antigen or cell, tissue, organ, etc. that expresses such antigen. Such immune responses also include any stimulation, production, induction, promotion or recruitment in a desired immune response specific to the antigen or cell, tissue, organ, etc. that expresses such antigen. Tolerogenic immune responses, therefore, include the absence of or reduction in an undesired immune response to an antigen that can be mediated by antigen reactive cells as well as the presence or promotion of suppressive cells. Tolerogenic immune responses as provided herein include immunological tolerance. To "generate a tolerogenic immune response" refers to the generation of any of the foregoing immune responses specific to an antigen or cell, tissue, organ, etc. that expresses such antigen. The tolerogenic immune response can be the result of MHC Class I-restricted presentation and/or MHC Class II-restricted presentation and/or B cell presentation and/or presentation by CD1d, etc. Tolerogenic immune responses include any reduction, delay or inhibition in CD4+ T cell, CD8+ T cell or B cell proliferation and/or activity. Tolerogenic immune responses also include a reduction in antigen-specific antibody production. Tolerogenic immune responses can also include any response that leads to the stimulation, induction, production or recruitment of regulatory cells, such as CD4+ Treg cells, CD8+ Treg cells, Breg cells, etc. In some embodiments, the tolerogenic immune response, is one that results in the conversion to a regulatory phenotype characterized by the production, induction, stimulation or recruitment of regulatory cells. "Undesired immune response" refers to any undesired immune response that results from exposure to an antigen, promotes or exacerbates a disease, disorder or condition provided herein (or a symptom thereof), or is symptomatic of a disease, disorder or condition provided herein. Such immune responses generally have a negative impact on a subject's health or is symptomatic of a negative impact on a subject's health. Undesired immune responses include antigen-specific antibody production, antigen-specific B cell proliferation and/or activity or antigen-specific CD4+ T cell proliferation and/or activity.

A "control" or "standard control" refers to a sample, measurement, or value that serves as a reference, usually a known reference, for comparison to a test sample, measurement, or value. For example, a test sample can be taken from a patient suspected of having a given disease (e.g. cancer) and compared to a known normal (non-diseased) individual (e.g. a standard control subject). A standard control can also represent an average measurement or value gathered from a population of similar individuals (e.g. standard control subjects) that do not have a given disease (i.e. standard control population), e.g., healthy individuals with a similar medical background, same age, weight, etc. A standard control value can also be obtained from the same individual, e.g. from an earlier-obtained sample from the patient prior to disease onset. For example, a control can be devised to compare therapeutic benefit based on pharmacological data (e.g., half-life) or therapeutic measures (e.g., comparison of side effects). Controls are also valuable for determining the significance of data. For example, if values for a given parameter are widely variant in controls, variation in test samples will not be considered as significant. One of skill will recognize that standard controls can be designed for assessment of any number of parameters (e.g. RNA levels, protein levels, specific cell types, specific bodily fluids, specific tissues, synoviocytes, synovial fluid, synovial tissue, fibroblast-like synoviocytes, macrophage-like synoviocytes, etc).

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

The term "inactive" or "inactived," as used herein to describe, e.g., inactivated microbial biomass, inactivated fermentation products, and inactivated fermenting microorganisms—refers to a state wherein a microorganism is dead, non-reproductive, and/or otherwise metabolically dormant.

Various aspects of the disclosure are described in further detail in the following subsections.

2. Methods of the Disclosure

As illustrated below, the method according to the present invention is based on multiple (i.e. two or more) separate microbial fermentations, which may be performed in parallel or sequential steps. According to the invention, each fermentation process in the method is carried out on a different fermentation substrate by a fermenting microorganism, wherein each fermenting microorganism used is different from any other fermenting microorganism employed in the fermentation steps, conducted either in parallel or in sequence.

In the context of the present description, the term "different" means that the fermenting microorganisms used for multiple fermentations according to the invention differ from each other in the genus, species or strain to which they belong. For example, a succession pattern of microorganisms involved in the fermentation steps of the method of the invention may include a *Lactobacillus* species, a *Lacticaseibacillus* species, a *Bifidobacterium* species and a *Saccharomyces* species, or, as another example, the succession order of the fermenting microorganisms may consist of different strains of the same microbial species, such as for example, different strains of a certain *Lactobacillus* species.

By exploiting the fermentation abilities of a combination of different microorganisms grown separately, the present invention allows advantageously to obtain a postbiotic preparation containing a complex mixture of metabolic by-products of various microorganisms, while avoiding the drawbacks that are typically associated with simultaneous fermentation processes, such as microbial growth competition and inhibition of production of certain metabolites by others.

The possibility of fermenting a matrix with multiple microorganisms is known in the art. Fermenting microorganisms can be inoculated simultaneously, allowing a so-called "mixed" fermentation, or in sequence, as described for winemaking, brewing (Liu W, et al; 2023. "Adjustment of Impact Phenolic Compounds, Antioxidant Activity and Aroma Profile in Cabernet Sauvignon Wine by Mixed Fermentation of *Pichia* Kudriavzevii and *Saccharomyces Cerevisiae.*" *Food Chemistry: X* 18:100685) and breadmaking (Fang L., et al; 2023. "Effects of Mixed Fermentation of Different Lactic Acid Bacteria and Yeast on Phytic Acid Degradation and Flavor Compounds in Sourdough." *LWT* 174:114438) processes.

In the method according to the invention, after each fermentation step, the fermenting microorganism in the resulting fermentation product is inactivated. In this way, advantageously the postbiotic composition comprises the whole and/or components of a plurality of inactivated microorganisms (cellular protein material, cellular nucleic material, cellular protoplasmic material and/or cell wall components), thereby acquiring different functional properties while at the same time reducing safety risks and poor stability associated with the presence of living bacteria.

No final or intermediate microbial inactivation has yet been described for multiple fermentation processes.

Therefore, a first embodiment of the present invention is a method of preparing a postbiotic composition comprising the steps of: inoculating at least two culture media each with a fermenting microorganism of a genus selected from the group consisting of the genera *Akkermansia, Bifidobacterium, Escherichia, Lactobacillus, Lactococcus, Lacticaseibacillus, Saccharomyces,* and *Streptococcus*, the inoculated fermenting microorganism in each culture medium being different from each other; fermenting the at least two culture media each under conditions suitable for fermentation by the respective inoculated fermenting microorganism, thereby obtaining at least two fermentation products each containing a fermenting microorganism; inactivating the fermenting microorganism in each fermentation product to obtain at least two inactivated fermentation products; and mixing the at least two inactivated fermentation products, thereby obtaining a postbiotic composition.

The advantages of using postbiotics compared to probiotics, include, for example, higher stability, as they do not contain living bacteria, and higher levels of safety, as they reduce the risk of microbial translocation, infection or enhanced inflammatory responses in subjects with imbalanced or compromised immune systems.

Figure 1:
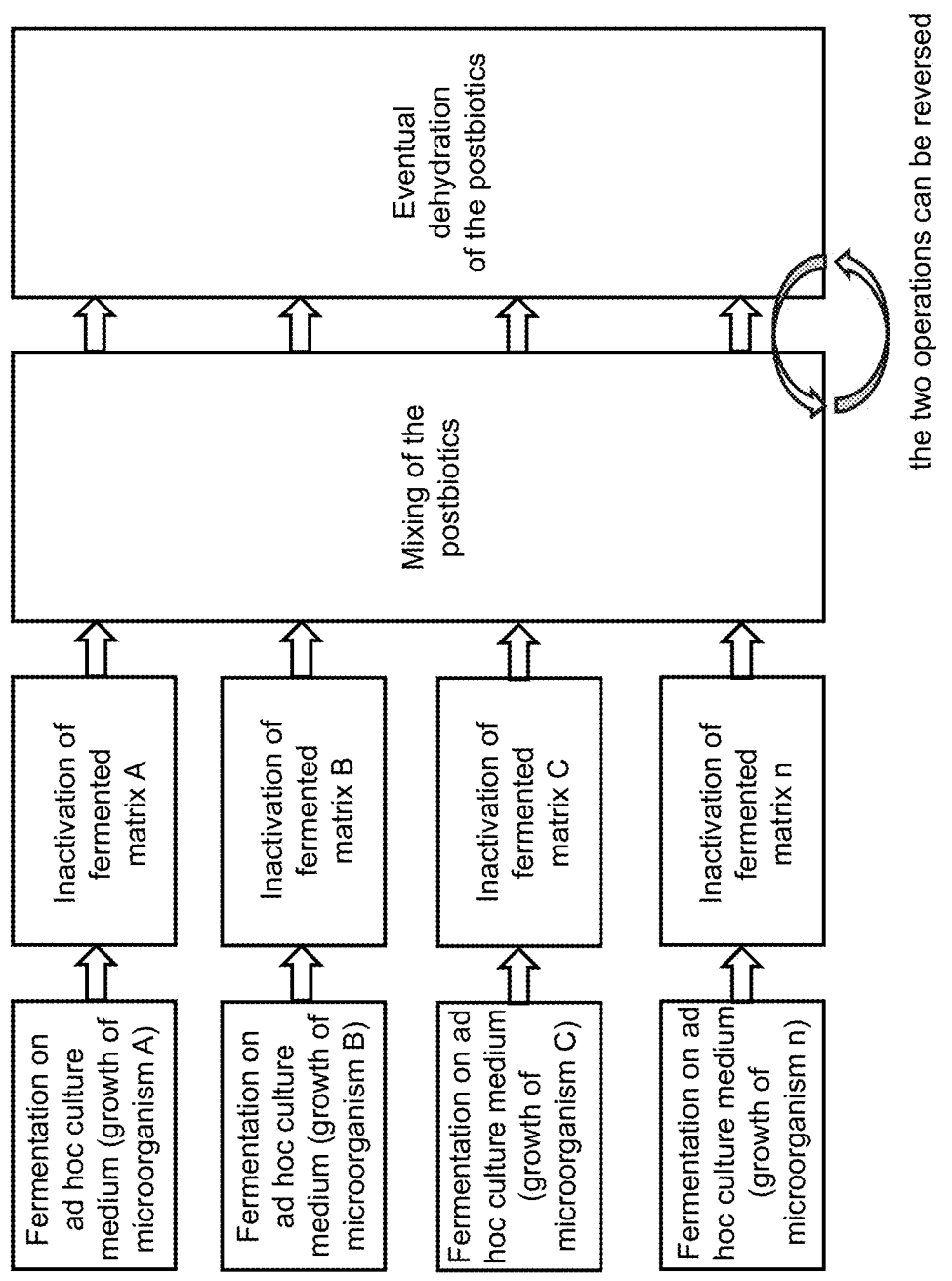
FIG. 1 illustrates the fermentation parallel process flow chart.

As shown in FIG. 1, two or more different microorganisms are allowed to be fermented in parallel, each in a culture medium containing sources of nutrients specific for the fermenting microorganism, and for a time that allows optimizing both the growth of microbial biomass and the production of functional and non-functional metabolites in the obtained fermentation products. After fermentation, the fermentation products are subjected to an inactivation process suitable for achieving microorganism death without modifying the bioactive components contained in said products. Subsequently, the inactivated fermentation products are combined with each other by mixing, thereby obtaining a postbiotic composition.

In this embodiment, the method according to the invention envisages the use of at least two culture media, more preferably more than two, for example at least 3, 4, 5, 6, 7, 8, 9, 10, 11, 12, 13, 14, 15, 16, 17, 18, 19 or 20 culture media which are inoculated each with a different fermenting microorganism, thus resulting in a multiple parallel fermentation process.

According to a second embodiment of the present invention, the method of preparing a postbiotic composition comprises the steps of: (i) inoculating a plurality of culture media with a plurality of fermenting microrganisms, wherein each culture medium is inoculated with a different fermenting microorganism; (ii) fermenting the inoculated plurality of culture media under conditions suitable for fermentation, thereby obtaining a plurality of fermentation products each containing a different fermenting microorganism; (iii) inactivating the fermenting microorganisms in the plurality of fermentation products to obtain a plurality of inactivated fermentation products; and (iv) mixing the plurality of inactivated fermentation products, thereby obtaining a postbiotic composition.

Figure 2:
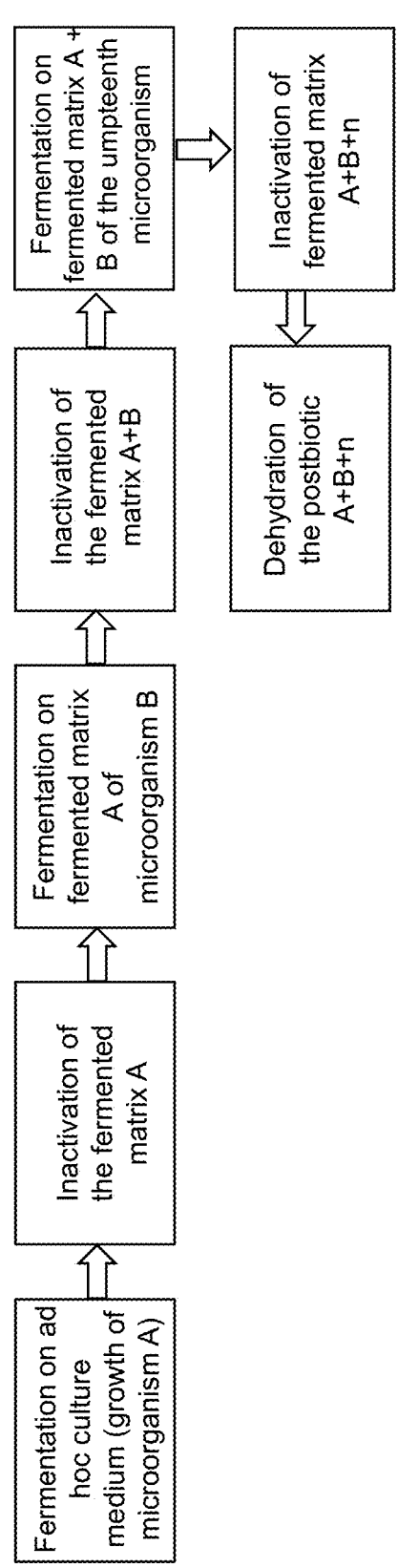
FIG. 2 illustrates the fermentation serial process flow chart.

FIG. 2 provides a schematic diagram of a method of preparing a postbiotic composition according to the second embodiment of the invention, wherein multiple sequential fermentations are carried out, each by a different microorganism on a different substrate. In said embodiment, a fermentation product obtained by the culture of a fermenting microorganism, after microbial inactivation, is used as a fermentation matrix for a next fermentation step wherein a microorganism different from the microorganisms previously employed is allowed to grow. By repeating in sequential order, the steps of microorganism inoculation, fermentation and inactivation as above described, a postbiotic composition can be obtained that includes all the employed inanimate fermenting microorganisms and their bioactive components.

In another aspect of the present invention is provided a method of preparing a postbiotic composition comprising the steps of: (i) inoculating a culture medium with a first fermenting microorganism; (ii) fermenting the culture medium under conditions suitable for fermentation by the first fermenting microorganism, thereby obtaining a first fermentation product comprising the first fermenting microorganism; (iii) inactivating the first fermenting microorganism in the first fermentation product to obtain a first fermentation matrix; (iv) inoculating the first fermentation matrix with a second fermenting microorganism; (v) fermenting the first fermentation matrix under conditions suitable for fermentation by the second fermenting microorganism, thereby obtaining a second fermentation product comprising the second fermenting microorganism; (vi) inactivating the second fermenting microorganism in the second fermentation product to obtain a second fermentation matrix, thereby obtaining a postbiotic composition; and optionally repeating steps (iv) to (vi) one or more times with an additional fermenting microorganism. In some aspects, each fermenting microorganism is a different species from any other fermenting microorganism, thereby obtaining a postbiotic composition. In some aspects, each fermenting microorganism is the same species.

According to the invention, steps (iv) to (vi) can be repeated any number of times, e.g., once, twice, three times, four times, five times, ten times, or more.

Optionally, in the aforementioned embodiment the inactivated fermentation product that is to be used as a matrix for a subsequent fermentation step may be supplemented with additional ingredients suitable for optimizing microbial growth and the performance of a fermentation process. Typical nutrient ingredients include, but are not limited to, sources of carbon, nitrogen, magnesium and phosphorus.

Suitable microorganisms for the parallel or sequential fermentation of the method of the present invention may be selected from a genus selected from the group consisting of the genera *Akkermansia, Bifidobacterium, Escherichia, Lactobacillus, Lactococcus, Lacticaseibacillus, Saccharomyces,* and *Streptococcus.*

In some embodiments, the fermenting microorganism is selected from the group consisting of a bacterial microorganism and a yeast microorganism. In some aspects, the bacterial microorganism is selected from the group consisting of an *Akkermansia* species, a *Bifidobacterium* species, an *Escherichia* species, *Lactobacillus* species, a *Lactococcus* species, a *Lacticaseibacillus* species, and a *Streptococcus* species. In some aspects, the yeast microorganism is selected from a *Saccharomyces* species.

In some embodiments, the fermenting microorganism is selected from the group consisting of *Akkermansia muciniphila, Bifidobacterium animalis, Bifidobacterium bifidum, Bifidobacterium infantis, Bifidobacterium breve, Bifidobacterium longum, Lactobacillus casei, Lactobacillus paracasei, Lactobacillus plantarum, Lactobacillus reuteri, Lactobacillus rhamnosus, Lacticaseibacillus paracasei, Saccharomyces boulardii,* and *Streptococcus salivarius.* In some embodiments, the fermenting microorganism is *Akkermansia muciniphila.* In some embodiments, the fermenting microorganism is *Bifidobacterium animalis.* In some embodiments, the fermenting microorganism is *Bifidobacterium bifidum.* In some embodiments, the fermenting microorganism is *Bifidobacterium infantis.* In some embodiments, the fermenting microorganism is *Bifidobacterium breve.* In some embodiments, the fermenting microorganism is *Bifidobacterium longum.* In some embodiments, the fermenting microorganism is *Lactobacillus casei.* In some embodiments, the fermenting microorganism is *Lactobacillus paracasei.* In some embodiments, the fermenting microorganism is *Lactobacillus plantarum.* In some embodiments, the fermenting microorganism is *Lactobacillus reuteri.* In some embodiments, the fermenting microorganism is *Lactobacillus rhamnosus.* In some embodiments, the fermenting microorganism is *Lacticaseibacillus paracasei.* In some embodiments, the fermenting microorganism is

*Lactobacillus plantarum*. In some embodiments, the fermenting microorganism is *Lactobacillus reuteri*. In some embodiments, the fermenting microorganism is *Lactobacillus rhamnosus*. In some embodiments, the fermenting microorganism is *Lacticaseibacillus paracasei*. In some embodiments, the fermenting microorganism is *Saccharomyces boulardii*. In some embodiments, the fermenting microorganism is *Streptococcus salivarius*.

In one embodiment, the *Bifidobacterium animalis* is *Bifidobacterium animalis* subsp. *lactis*.

In one embodiment, the *Escherichia coli* is *E. coli* Nissle 1917.

In some embodiments, the *Lacticaseibacillus paracasei* is *Lacticaseibacillus paracasei* NPB01.

In one embodiment, the fermenting microorganism is *Lacticaseibacillus paracasei* NPB-01. In some embodiments, the postbiotic composition comprises a teichoic acid. In some embodiments, the postbiotic composition comprises one or more polysaccharides. In some embodiments, the one or more polysaccharides comprise one or more capsular polysaccharides. In some embodiments, the teichoic acid is from *Lacticaseibacillus paracasei* NPB-01. In some embodiments, the one or more polysaccharides are from *Lacticaseibacillus paracasei* NPB-01. In some embodiments, the one or more capsular polysaccharides are from *Lacticaseibacillus paracasei* NPB-01 (e.g., a capsular polysaccharide described in Example 4).

In one embodiment, the microorganisms of the genus *Lactobacillus* are selected from the group consisting of *Lacticaseibacillus paracasei, Lacticaseibacillus rhamnosus, Lactiplantibacillus plantarum, Limosilactobacillus reuteri,* and *Lactobacillus delbrueckii*.

Non-limiting examples of microorganisms of the genus *Bifidobacterium* suitable for use in the method of the invention are the species *Bifidobacterium longum, Bifidobacterium animalis, Bifidobacterium breve*, and *Bifidobacterium infantis*.

According to the invention, the microorganism of the *Lactococcus* genus is preferably a *Lactococcus lactis* strain, the microorganism of the *Streptococcus* genus is preferably a *Streptococcus thermophilus* strain, and/or the microorganism of the *Saccharomyces* genus is preferably a strain selected from *Saccharomyces boulardii* and *Saccharomyces cerevisae*.

Any culture medium may be used in the present invention, which may be selected based on the nutritional requirements of the fermenting microorganisms in order to maximize bacterial growth, yield of postbiotic metabolites and bioactivity and to confer specific organoleptic characteristics to the postbiotic composition.

Non-limiting examples of suitable culture media include MRS media, BHI broth (including BHI broth supplemented with PGM), LB broth, plant-derived media, functional media containing plant extracts with antioxidant, antiviral and/or antibacterial activity, culture media of natural origin, and any combination thereof.

The selection of the most appropriate culture medium is well known to those skilled in the art.

According to the method of the invention, the fermentation step is preferably carried out at a temperature comprised between 25° C. and 45° C., more preferably at 37° C., for a time of at least two hours, more preferably for 6 to 24 hours. The pH is typically kept at a value comprised between 4.0 and 7.0, preferably at 6.2. In some aspects, the fermentation step is carried out at a temperature from about 25° C. to about 45° C.

In some aspects, there are one or more single fermentation steps followed by one or more serial fermentation steps. In some aspects, the single fermentation step is carried out for up to about 24 hours. In some aspects, the one or more serial fermentation steps are carried out for up to about 6 hours or up to about 12 hours. In some aspects, the total serial fermentation time is up to about 36 hours.

The fermentation process can be carried out in any type of stirred or wave-type bio-reactor. Examples of useful bioreactors for the present invention include, but are not limited to batch reactors, fed-batch reactors, CSTR (Continuous-flow Stirred-Tank Reactor) reactors.

In the method of the invention, the step of inactivating the fermenting microorganism in the fermentation product may be carried out by means of various techniques, as are known in the art. Such techniques include, but are not limited to, heat treatment, chemical treatment (e.g., formalin), gamma or ultraviolet irradiation, high pressure and sonication. Sonication, in particular is the method most commonly used to produce cell lysates: in the second embodiment, this method can increase the availability of functional components, enhancing the fermentation performances of the second microorganism.

Heat inactivation of the fermenting microorganism in the fermentation product is particularly preferred. Preferably, heat inactivation is conducted at a temperature comprised from about 50° C. to about 100° C. for a time of about 5 seconds to about 120 seconds. In an exemplary embodiment, heat inactivation is conducted at about 80° C. for about 30 seconds.

In a more preferred embodiment, the fermentation product of the method according to the invention is a culture broth.

Suitably the method of the present invention may additionally comprise the step of drying the postbiotic composition. Techniques for carrying out the drying step of the invention are known and described in the state of the art, therefore the selection and use thereof are within the skills of one of ordinary skill in the art.

The use of freeze-drying, granulation, and spray drying is mentioned by way of a non-limiting example.

Alternatively, in the embodiment of the invention based on multiple parallel fermentations, the inactivated fermentation products of step (iii) may be processed into a dried form, and then admixed together to obtain a dried postbiotic composition, or the wet inactivated fermentation products may be mixed and then processed into a dried form (FIG. 1).

In some embodiments, before inoculating with a fermenting microorganism, the inactivated fermentation product is supplemented with one or more additional ingredients.

In some embodiments, the method further comprises drying the inactivated fermentation product and wherein said dried inactivated fermentation product is optionally rehydrated in water prior to subsequent inoculation with a fermenting microorganism.

In some embodiments, the method further comprises the step of drying the postbiotic composition.

When the method of the invention is carried out by means of multiple sequential fermentations, after fermentation and inactivation of the first microorganism, the fermentation matrix is inoculated with a second microorganism, and fermentation of the second microorganism is performed (FIG. 2). According to one embodiment, after inactivation, the fermentation product may be subjected to a drying process and optionally stored in dried form, and the inactivated fermentation product in dried form may be rehydrated,

19

Figure 3:
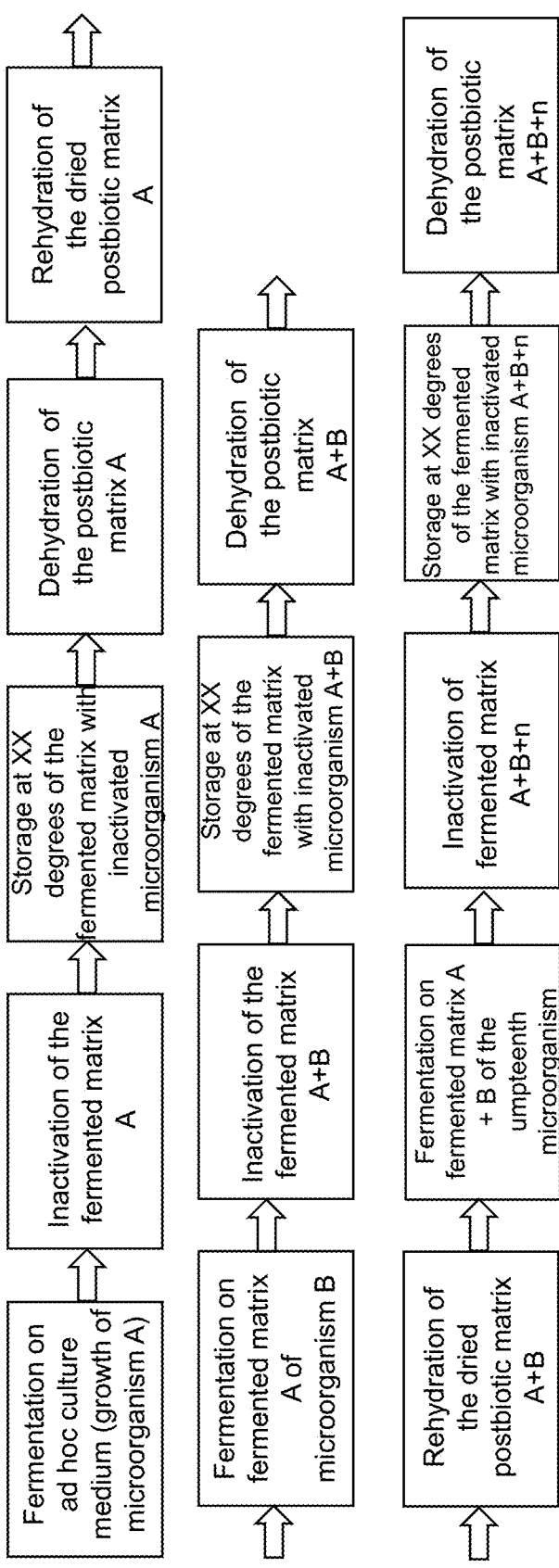
FIG. 3 illustrates a variant of the fermentation serial process allowing for optional intermediate storage phase.

20 for example in water, prior to inoculation with a different fermenting microorganism (FIG. 3).

Optionally, the method according to the invention, in both the first and second embodiments as above described, may further comprise subjecting the fermentation product to a centrifugation step after inactivation to separate the fraction consisting of the inactivated fermenting microorganisms (which form a pellet of cell bodies) from the remaining portion of the inactivated fermentation product, which contains the functional components (supernatant) and which in turn may be used as a fermentation matrix in or for the subsequent fermentation step. After the centrifugation step, either the pellet of cell bodies and/or the supernatant thus obtained may optionally be subjected to a drying phase.

Also provided herein is a postbiotic composition described herein for use in the prevention or the therapeutic treatment of a disease in a subject in need thereof selected from the group consisting of infectious and inflammatory diseases, immune-mediated diseases, cancer diseases, skin disorders, gastrointestinal diseases (e.g., Celiac disease), urogenital tract diseases, neurologic disorders, neuropsychiatric disorders, bone diseases, muscle diseases, malnutrition, metabolic diseases, and any combination thereof.

In some aspects, administration of a postbiotic composition described herein results in an increased production in the subject of one or more of short-chain fatty acids, bile acids, choline metabolites, vitamins, amino acids (e.g., tryptophan), and/or neurotransmitters (e.g., mucosal serotonin release).

Also provided herein is a postbiotic composition described herein for use in promoting healthy aging in a mammal. Healthy aging is defined as a continuous process of optimizing opportunities to maintain and improve physical and mental health, independence, and quality of life throughout the life course.

Also provided herein is a postbiotic composition described herein for correcting drug-induced nutrient depeletions (DIND) in a mammal. DIND is a side effect of some medications that can cause nutritional deficiencies. These deficiencies can start months or years after starting a medication and can lead to other health problems. Some common drugs that can cause DIND include oral contraceptives, cholesterol-lowering statins, antibiotics, and diuretics. In some aspects, the DIND is cause by a glucagonlike peptide 1 (GLP-1) agonists, for example, semaglutide.

Also provided herein is a postbiotic composition described herein for use in improving the function of the gut barrier by increasing the expression of tight junction proteins and/or mucous proteins, and/or increasing enterocyte growth and differentiation in a subject in need thereof. In some aspects, the tight junction proteins comprise occludin and/or ZO-1. In some aspects, the mucous proteins comprise MUC5AC. In some embodiments, following treatment with the postbiotic composition, the expression of occludin, ZO-1, and/or MUC5AC is increased by at least about 2-fold, about 3-fold, about 4-fold, about 5-fold, or more compared to an untreated subject. In some embodiments, following treatment with the postbiotic composition, the expression of occludin, ZO-1, and/or MUC5AC is increased by at least about 25%, about 50%, about 75% or more compared to treatment with a composition comprising a single living microorganism.

Also provided herein is a postbiotic composition described herein for use in increasing the expression of β-defensin-2 (HBD-2) in a subject in need thereof. In some embodiments, following treatment with the postbiotic composition, the expression of HBD-2 is increased by at least about 2-fold, about 3-fold, about 4-fold, about 5-fold, about 7-fold, about 8-fold or more compared to an untreated subject. In some embodiments, following treatment with the postbiotic composition, the expression of HBD-2 is at least about 2-fold, about 3-fold, about 4-fold, or more compared to treatment with a composition comprising a single microorganism.

Also provided herein is a postbiotic composition described herein for use in increasing the expression of cathelicid LL-37 in a subject in need thereof. In some aspects, following treatment with the postbiotic composition, the expression of cathelicid LL-37 is increased by at least about 2-fold, about 3-fold, or more compared to an untreated subject.

Also provided herein is a use of a postbiotic composition described herein in a food, a beverage, a pharmaceutical, a nutraceutical, a cosmetic, or a packaging composition, and wherein the composition further comprises at least one pharmaceutically acceptable vehicle, excipient and/or diluent. In some embodiments, the use is for improving the gut barrier function in a mammal. In some embodiments, the use is for improving innate immune responses against infection in a mammal. In some embodiments, the use is for generating a tolerogenic immune response in a mammal. In some embodiments, the use is for protecting the skin against infections in a mammal.

Also provided herein is a use of a postbiotic composition described herein for antiaging effects, including improving gut microbial composition in vivo, reducing cholesterol, and facilitating the production of SCFAs by modulating gut microbiota.

Also provided herein is a use of a postbiotic composition described herein for anticancer effects, including reducing the growth rate of human colon cancer cells in vitro.

Also provided herein is a use of a postbiotic composition described herein for antibacterial effects, including having antibacterial activity against *E. coli* and inhibiting of *S. aureus*.

Also provided herein is a use of a postbiotic composition described herein for antibiofilm effects, including having antibiofilm activity against *E. coli* biofilms.

Also provided herein is a use of a postbiotic composition described herein for anti-inflammatory effects, including protecting human colonic muscle from damage by pathogenic *E. coli*, having anti-inflammatory activity against porcine intestinal epithelial cell line IPEC-J2, promoting dendritic cell maturation, and eliciting secretion of anti-inflammatory cytokine IL-10 in vivo.

Also provided herein is a use of a postbiotic composition described herein for antioxidant effects, including having 2,2'-azino-bis-(3-ethylbenzothiazoline-6-sulfonic) acid (ABTS) radical scavenging activity, having 2,2-diphenyl-1-picrylhydrazyl (DPPH) radical scavenging activity, and having ferric-reducing power.

Also provided herein is a use of a postbiotic composition described herein for immune regulation effects, including balancing IL-8 mRNA expression induced by surface molecules (such as lipoteichoic acid), stimulating pro-inflammatory IL-12 and TNF-α cytokines, improving adhesion of probiotics to the epithelium, enhancing expression of tight junction proteins, and improving intestinal mucosal barrier function.

Also provided herein is a use of a postbiotic composition described herein for antitumor effects, including inhibiting proliferation of cancer and tumor cells.

Also provided herein is a use of a postbiotic composition described herein for inflammatory bowl disease (IBD)

effects, including reducing neutrophils in crypt and surface epithelial cells and reprogramming intraepithelial CD4+ T cells into CD4$^+$CD8aa$^+$ immunoregulatory T cells.

Also provided herein is a method of preventing or treating a disease selected from the group consisting of infectious and inflammatory diseases, immune-mediated diseases, cancer diseases, skin disorders, gastrointestinal diseases, urogenital tract diseases, neurologic disorders, neuropsychiatric disorders, bone diseases, muscle diseases, malnutrition, metabolic diseases, and any combination thereof, wherein the method comprises administering to a subject in need thereof a postbiotic composition described herein.

Also provided herein is a method of improving the function of the gut barrier by increasing the expression of tight junction proteins and/or mucous proteins, and/or increasing enterocyte growth and differentiation in a subject in need thereof. In some aspects, the tight junction proteins comprise occludin and/or ZO-1. In some aspects, the mucous proteins comprise MUC5AC. In some embodiments, following treatment with the postbiotic composition, the expression of occludin, ZO-1, and/or MUC5AC is increased by at least about 2-fold, about 3-fold, about 4-fold, about 5-fold, or more compared to an untreated subject. In some embodiments, following treatment with the postbiotic composition, the expression of occludin, ZO-1, and/or MUC5AC is increased by at least about 25%, about 50%, about 75% or more compared to treatment with a composition comprising a single living microorganism.

Also provided herein is a method of increasing the expression of β-defensin-2 (HBD-2) in a subject in need thereof, wherein the method comprises administering to the subject a postbiotic composition provided herein. In some embodiments, following treatment with the postbiotic composition, the expression of HBD-2 is at least about 2-fold, about 3-fold, about 4-fold, about 5-fold, about 7-fold, about 8-fold or more compared to an untreated subject. In some embodiments, following treatment with the postbiotic composition, the expression of HBD-2 is increased by at least about 2-fold, about 3-fold, about 4-fold, or more compared to treatment with a composition comprising a single microorganism.

Also provided herein is a method for increasing the total amount of one or more metabolites of L-tryptophan in a subject in need thereof, wherein the method comprises administering to the subject a postbiotic composition provided herein. In some aspects, the one or more metabolites of L-tryptophan comprise indole-3-acetic acid, indole-3-lactic acid, and/or L-kynurenine.

Also provided herein is a method for increasing the total amount of L-tryptophan in a subject in need thereof, wherein the method comprises administering to the subject a postbiotic composition provided herein.

Also provided herein is a method for increasing the ratio of L-tryptophan to large neutral amino acids in the plasma of a subject in need thereof, wherein the method comprises administering to the subject a postbiotic composition provided herein.

Also provided herein is a method for increasing the biosynthesis of serotonin and/or melatonin in a subject in need thereof, wherein the method comprises administering to the subject a postbiotic composition provided herein.

Also provided herein is a method for promoting healthy aging in a subject in need thereof, wherein the method comprises administering to the subject a postbiotic composition provided herein.

Also provided herein is a method for correcting drug-induced nutrient depletions in a subject in need thereof, wherein the method comprises administering to the subject a postbiotic composition provided herein.

Also provided herein is a postbiotic composition produced from a multi-microorganism fermentation, wherein the multi-microorganism fermentation comprises the fermentation of two or more bacterial or yeast species. In some embodiments, the postbiotic comprises two or more inactivated fermentation products. In some embodiments, the multi-microorganism fermentation comprises a method described herein.

Also provided herein is a postbiotic composition comprising: (a) a first matrix comprising a first inactivated microorganism and the culture medium in which the microorganism was inactivated; and (b) one or more additional matrices each comprising an additional inactivated microorganism and the culture medium in which the microorganism was inactivated. In some aspects, the first inactivated microorganism and each additional inactivated microorganism is a different species. In some embodiments, the first inactivated microorganism and each additional inactivated microorganism is the same species. In some embodiments, the postbiotic composition is prepared according to a method described herein.

The preferred embodiments described above can be combined with each other as required, and the implementation of these combinations falls within the skills of the person skilled in the art.

As mentioned above, advantageously, the present invention provides a method that allows the production of a postbiotic composition containing unique metabolic actives since each individual fermentation and inactivation process affects the quality and quantity of the final postbiotic produced and may results in different postbiotics with different effects and different properties.

As it will be illustrated in the following experimental section, it has surprisingly been found that the methods according to the invention allows to obtain a synergistically active postbiotic composition having beneficial properties, including for example, an immunopotentiation effect in human colon cells.

Therefore, the present invention also relates to a postbiotic composition that can be obtained by means of the methods of the present invention as above defined, characterized by comprising lactic acid at a concentration comprised within the range of from 1 to 30 g/L on the total volume of the composition and/or an amount of inactivated fermenting microorganisms comprised within the range of from 0.00015 g/L to 150 g/L on the total volume of the composition.

Preferred lactic acid concentrations in the postbiotic composition according to the present invention are within the range of from 5 to 25 g/L, more preferably within the range of 10 to 20 g/L.

Preferred amounts of inactivated fermenting microorganisms are within the range of 0.0005 g/L to 100 g/L, or within the range of 0.05 g/L to 50 g/L, or within the range of 0.2 g/L to 5 g/L.

3. Compositions and Kits of the Disclosure

Also provided herein are compositions comprising a postbiotic produced by a method of the disclosure. In a preferred embodiment the postbiotic composition according to the present invention is suitable for use as human and animal food supplement, or food ingredient, for example for food biopreservation.

Also provided herein is a postbiotic composition produced from a multi-microorganism fermentation, wherein the multi-microorganism fermentation comprises the fermentation of two or more bacterial or yeast species. In some aspects, the postbiotic comprises two or more inactivated fermentation products. In some aspects, the multi-microorganism fermentation comprises a method described herein.

Also provided herein is a postbiotic composition comprising: (a) a first matrix comprising a first inactivated microorganism and the culture medium in which the microorganism was inactivated; and (b) one or more additional matrices each comprising an additional inactivated microorganism and the culture medium in which the microorganism was inactivated. In some aspects, the first inactivated microorganism and each additional inactivated microorganism is a different species. In some aspects, the postbiotic composition is prepared according to a method described herein.

In some aspects, the postbiotic composition comprises cell-containing postbiotics. In some aspects, the postbiotic composition comprises cell-free postbiotics. In some aspects, the postbiotic composition comprises: inactivated microorganisms, primary microbial metabolites, secondary microbial metabolites, cell-free supernatant (CSF), cell-free spent media (CFSM), cell lysates, short chain fatty acids (SCFAs), vitamins, enzymes, proteins, peptides, organic acids, flavonoid-derived postbiotics, terpenoid-derived postbiotics, exopolysaccharides (EPS), peptidoglycan, lipoteichoic acids (LTAs), phenolic-derived postbiotics, cell wall fragments, and lipopolysaccharides (LPSs).

Also provided herein is a postbiotic composition obtained by a method described herein, further comprising lactic acid at a concentration of about 1 g/L to about 30 g/L on the total volume of the composition and/or an amount of inactivated fermenting microorganisms of about 0.00015 g/L to about 150 g/L on the total volume of the composition. In some aspects, the amount of inactivated fermenting microorganisms comprises about $10^5$ cells/ml to about $10^{11}$ cells/ml.

Also provided herein is a postbiotic composition obtained by a method described herein, further comprising L-tryptophan or a dipeptide containing L-tryptophan. In some aspects, the composition comprises L-tryptophan at a concentration of at least 0.01% w/w. In some aspects, the composition comprises L-tryptophan at a concentration of at least 0.10% w/w. In some aspects, the L-tryptophan is present in an amount of at least 10 mg, at least 50 mg, or at least 100 mg.

Also provided herein is a postbiotic composition obtained by a method described herein, wherein at least one of the fermenting microorganisms used to obtain the postbiotic composition is *L. paracasei* NPB01.

Also provided herein is a postbiotic composition obtained by a method described herein, wherein the postbiotic composition further comprises one or more *L. paracasei* NPB01-derived polysaccharides. In some aspects, the one or more *L. paracasei* NPB01-derived polysaccharides comprise a teichoic acid and/or one or more capsular polysaccharides (e.g., a capsular polysaccharide described in Example 4).

In another embodiment, the postbiotic composition according to the present invention is for use as a medicament, particularly as a beneficial modulator of the following: gut microbiome structure and function, immune system, cell growth and differentiation, gut barrier, brain function, skin health. More preferably, the postbiotic composition according to the invention is useful in the treatment and/or prevention of infectious and inflammatory diseases, immune-mediated disease, cancer, skin disorders, gastrointestinal diseases, urogenital tract diseases, and brain disorders.

According to the invention, the postbiotic composition can be administered via any suitable route of administration. For example, the composition may be administered to animals (including humans) in an orally ingestible form. In case of a food composition or nutraceutical, the postbiotic composition can simply be incorporated in a conventional food item or food supplement. Exemplary pharmaceutical formulations include capsules, microcapsules, tablets, granules, powder, troches, pills, suspensions and syrups. In another embodiment, the composition is in a form for rectal administration to an animal (including humans), for instance as rectal suppository or enema. For topical administration, the pharmaceutical composition may be formulated in a gel, ointment, cream, or salve.

Suitable formulations may be prepared by methods commonly employed using conventional organic and inorganic additives. The amount of active ingredient in the pharmaceutical composition may be at a level that will exercise the desired therapeutic effect.

A further aspect of the invention is a pharmaceutical, nutraceutical, or cosmetic composition, or a food product or food supplement comprising a postbiotic composition as described above, in combination with at least one pharmaceutically acceptable vehicle, excipient and/or diluent.

For preparing the food product according to the invention, the postbiotic composition may be incorporated into an edible material using a standard technique well known to one of ordinary skill in the art. For instance, the aforesaid postbiotic composition may be directly added to the edible material, or may be utilized for preparing an intermediate composition (e.g., a food additive or a premix) suitable to be subsequently added to the edible material.

According to the invention, the food product may be in the form of fermented foods, processed foods, health foods, or dietary supplements.

Also provided herein is a kit comprising a postbiotic composition described herein.

Also provided herein is a kit comprising a multi-microorganism fermentation matrix and an inoculum comprising two or more inactivated microorganisms. In some embodiments, the postbiotic composition is prepared according to a method described herein. In some embodiments, the kit further comprises documentation comprising steps and conditions for use.

In various embodiments, kits for use in the laboratory and therapeutic applications described herein are within the scope of the present disclosure. Such kits may comprise a carrier, package, or container that is compartmentalized to receive one or more containers such as vials, tubes, and the like, each of the container(s) comprising one of the separate elements to be used in a method disclosed herein, along with a label or insert comprising instructions for use, such as a use described herein.

Kits may comprise the container described above, and one or more other containers associated therewith that comprise materials desirable from a commercial and user standpoint, including buffers, diluents, filters, needles, syringes; carrier, package, container, vial and/or tube labels listing contents and/or instructions for use, and package inserts with instructions for use.

A label may be present on or with the container to indicate that the composition is used for a specific therapy or non-therapeutic application, such as a prognostic, prophylactic, diagnostic, or laboratory application. A label may also indicate directions for either in vivo or in vitro use, such as those described herein. Directions and or other information may also be included on an insert(s) or label(s), which is included with or on the kit. The label may be on or associated with the container. A label may be on a container when letters, numbers, or other characters forming the label are molded or etched into the container itself. A label may be associated with a container when it is present within a receptacle or carrier that also holds the container, e.g., as a package insert. The label may indicate that the composition is used for diagnosing or treating a condition, such as a cancer a described herein.

The embodiments described above can be combined with each other as required, and the implementation of these combinations falls within the skills of the person skilled in the art.

The present invention is further illustrated by the following examples which should not be construed as further limiting. The contents of all references cited throughout this application are expressly incorporated herein by reference.

EXAMPLES

Example 1: Materials and Methods

The bacterial species chosen in the following examples are the most frequently used for fermented food and food supplements, and they are recognized as probiotic microorganisms and for their beneficial effect on human health.

Regarding the tests on the eukaryotic genus, *Saccharomyces boulardii* is the most often used as a dietary supplement or in combination with other probiotics to maximize gut health benefits; for this, we hypothesized to test it and in combination with other genera.

The bacteria used in the present experiments belong to the Lactobacillaceae family, in particular to the *Lactobacillus* genus, *Lacticaseibacillus paracasei, Lacticaseibacillus rhamnosus, Lacticaseibacillus plantarum* and *Lacticaseibacillus casei* species. All lactobacilli are Gram-positive, facultative anaerobic, homofermentative microorganisms.

The microorganism *Lacticaseibacillus paracasei* was provided by Science Power S.r.l., *Lacticaseibacillus rhamnosus* GG (LGG) was isolated from a commercial food supplement (Dicoflor capsules), *Lacticaseibacillus casei* was isolated from a dairy product and *Lacticaseibacillus plantarum* was isolated from a commercial food supplement (Femelle capsules).

Other microorganisms' genera were also used; they belong to the Bifidobacteria, *Streptococcus* and *Saccharomyces* families. In particular, *Bifidobacterium bifidum* was isolated from a commercial food supplement (*Bifidobacterium* Life Nutrition capsules), *Streptococcus salivarius* was isolated from a commercial food supplement (Bactolactis tablets) and *Saccharomyces boulardii* was isolated from a commercial food supplement (Fair & Pure capsules).

TABLE 1

| Microorganism Abbreviations | |
| --- | --- |
| LP | *Lactobacillus paracasei* |
| LGG | *Lactobacillus rhamnosus* |
| Lpl | *Lactobacillus plantarum* |
| Lc | *Lactobacillus casei* |
| Bb | *Bifidobacterium bifidum* |
| Ss | *Streptococcus salivarius* |
| Sb | *Saccharomyces boulardii* |

In particular, the fermentation process was performed under the following conditions. The microorganisms were inoculated in the broth and fermented separately for 24 hours and then a thermic inactivation was carried out. After the drying, obtained in the present experimentation by spray drying, the powders derived from the two processes were mixed (50:50 and 80:20) (i.e., LP 50%+LGG 50% and LP 80%+LGG 20%).

The first microorganism was inoculated in the broth and fermented for 6 or 24 hours. After an abatement the second microorganism was added to the exhaust broth and a second fermentation was carried out for 24 hours, followed by a second abatement.

Specifically, the following conditions were tested: 24-hour fermentation of the first microorganism (LP or LGG)+24-hour fermentation of the second microorganism (LGG or LP); 6-hour fermentation of the first microorganism (LP or LGG)+24-hour fermentation of the second microorganism (LGG or LP).

All the fermented products were then dried by a sprydrying process.

In all tested cases the process was characterized according to microbiological parameters, with definition of the microorganism's growth curve and according chemical parameters, with quantification of the lactic acid produced, as the main metabolite of microbial metabolism.

Experimental Set Using Other *Lactobacillus* Species (Lpl and Lc) and Other Genera (Bb, Ss and Sb)

Not all the combinations of the first experimental set were tested, but based on the results obtained from this, the most indicative combinations for the purpose have been studied.

The microorganisms (Lpl, Lc, Bb, Ss and Sb) were inoculated in the broth and fermented separately for 24 hours and then a thermic inactivation was carried out. The fermented inactivated broths was then dried by spray drying process. The powders derived were also mixed to obtain a postbiotic composition (Lpl 50%+Lc 50% and Bb 34%+Ss 33%+Sb 33%).

Other *Lactobacillus* species: the first microorganism (Lpl) was inoculated in the broth and fermented for 6 hours. After an abatement, the second microorganism (Lc) was added to the inactivated broth and a second fermentation was carried out for 24 hours, followed by a second abatement. Similarly, a serial fermentation process was conducted by reversing the order of the microorganisms. The fermented inactivated broths were then dried by a spry drying process.

Other genera: the first microorganism (Bb) was inoculated in the broth and fermented for 6 hours. After an abatement, the second microorganism (Ss) was added to the inactivated broth and a second fermentation was carried out for 6 hours, followed by a second abatement. A third microorganism (Sb) was inoculated, and a third fermentation was carried out for 24 h followed by a further abatement. The fermented inactivated broth was then dried by a spry drying process.

In all tested cases the process was characterized according to microbiological parameters, with definition of the microorganism's growth and according to chemical parameters, with quantification of the lactic acid produced.

Strains and Revitalization

The microorganisms were stored at −80° C. in cryovials with glycerol (20%) and reactivated through incubation at 37° C. for 24 h in MRS broth (Sigma-Aldrich) for all microorganisms belonging to the *Lactobacillus* family and *Streptococcus salivarius; Bifidobacterium bifidum* was reactivated through incubation at 37° C. for 24 h in BSM-broth (Millipore); *Saccharomyces boulardii* was reactivated through incubation at 37° C. for 24 h in Yeast Mold Broth (Difco).

The cell density in the inoculum broths was $10^8$ CFU/mL.

Fermentation

Fermentations were carried out using a batch reactor (1 L) equipped with an external jacket for the circulation of a service fluid (water) from a thermostatically controlled water bath. The MRS medium was inoculated (1% v/v), and fermentation was performed for a specific number of hours according to each embodiment of the two experimental sets, by setting a stirring speed of 81 rpm.

The fermentation process was carried out under controlled temperature and pH conditions (37° C. and 6.2, respectively). Fermented samples were withdrawn aseptically from the reactor at specific times.

Analytical Methods

Microbiological Analyses

Serial dilutions and the spread plate method on Petri plates filled with De Man, Rogosa, and Sharpe (MRS) agar (Oxoid, Basingstoke, UK), BSM agar (Millipore) and Yeast Mold agar (Difco), and were performed for lactobacilli and *Streptococcus, Bifidobacterium* and *Saccharomyces* counting, respectively.

MacConkey agar (Oxoid, Basingstoke, UK) and Gelatin Peptone Bios Agar (Biolife, Milan, Italy) were used to control the presence of microbial contaminants. All plates were incubated at 37° C. for 48 hours before reading.

Lactic Acid Production

Lactic acid production was monitored by high-performance liquid chromatography (HPLC) using an Agilent Technologies 1100 equipped with a Phenomemenx Synergi Hydro-RP C18 column (250 mm×4.6 mm and a pore size of 4 μm) with a visible/UV detector. The mobile phase consisted of a 0.27% $KH_2PO_4$ aqueous solution at pH=1.5 modified with $H_3PO_4$ with a flow rate 1 ml/min. The column temperature was set at 60° C. and the wavelength at 210 nm.

Biological Tests

Cell Model

The human enterocyte cell line Caco-2 (American Type Culture Collection, Teddington, Middlesex TW11 0LY, United Kingdom) was used for all experiments. These cells, after 14 days post confluence, reach the morpho-functional characteristics of enterocytes of the human small intestine. Cells were grown in Dulbecco's Modified Eagles's Medium (DMEM-Gibco, Berlin, Germany) supplemented with 20% fetal bovine serum (Lonza, Visp, Switzerland), 1% L-glutamine (Lonza), 1% essential amino acids, and 1% penicillin/streptomycin (Lonza). The cells were plated and cultured at 37° C. in 5% $CO_2$. All experiments were performed when cells had reached full functional differentiation (after 14 days of post-confluence culture).

Cell Stimulation Protocol

Before cell stimulation, the present inventors dosed the protein amount of postbiotic products with the Bradford method and normalized for the protein concentration. The used dose of 11.5 mg/mL was established by dose-response experiments. Human enterocytes were stimulated for 48 hours with the postbiotic products studied. Cells stimulated with culture medium alone were used as a control. All experiments were performed in triplicate and were repeated 2 times.

Analysis of the Production of the Innate Immunity Peptide HBD-2

After cell stimulation, the supernatant was collected and stored at −80° C. The concentration of HBD-2 was determined by using an ELISA kit specific (Hycult Biotech, Uden, The Netherlands), with a sensitivity limit of 0.1 ng/ml.

Analysis of Intestinal Barrier Integrity Markers by Real Time PCR

After collecting the supernatant, the cells were also collected and centrifuged at 1200 rpm for 10 minutes and used for total RNA extraction using TRIZOL (Gibco BRL, Paisley, Scotland), following the manufacturer's instructions. Real Time PCR was performed using TaqMan probes: occludin (Hs00170162_m1), zonula occludens-1 (ZO-1, Hs01551871_m1) and mucin 5AC (MUC5AC, Hs01365616_m1). TaqMan probes for these genes were inventoried and tested by the manufacturing company's quality control (QC) department (Applied Biosystems, Waltham, Massachusetts, United States). The amplification conditions used were the following: 2 min. at 50° C., 10 min. at 95° C., and 40 cycles of 25 sec at 95° C. and 1 min. at 60° C. The expression of each gene was normalized to that of glyceraldehyde-3-phosphate dehydrogenase (GAPDH, Hs02786624_g1) to obtain a relative quantification of the transcript of interest. The relative expression of each gene was calculated with the 2-ΔΔCT method: (ΔΔCT=ΔCTsample-ΔCTcontrol). Each sample was analyzed in triplicate.

The characterization of the fermentation processes for all microorganisms and conditions tested are reported below in Example 2.

Example 2: Results

The LGG and LP microorganisms were fermented separately, inactivated, dried and then mixed together. The growth curves were obtained for 24 hours cultivation of LGG and LP, respectively, as shown in FIGS. 4A (LGG) and B (LP).

Figures 5A, 5B:
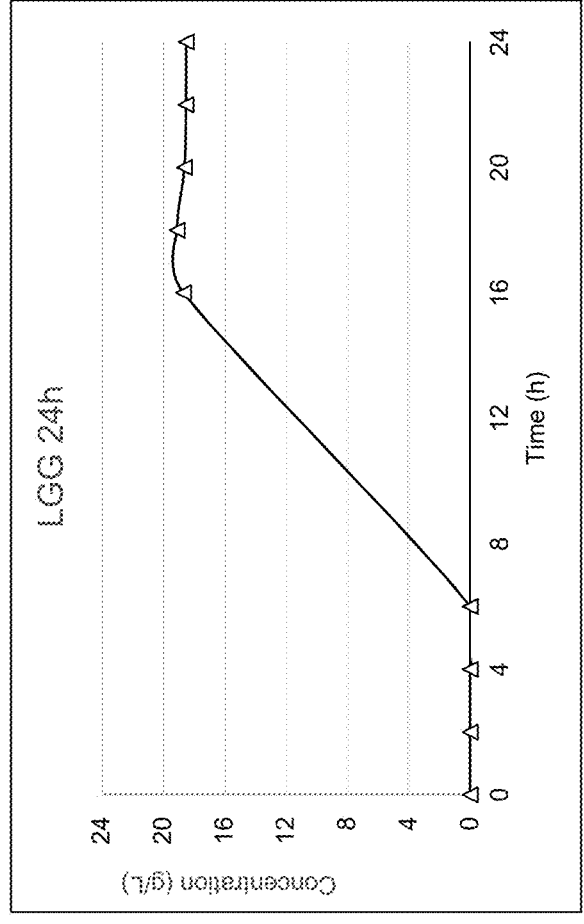
FIGS. 5A-5B illustrate LGG's 24 h lactic acid accumulation curve (FIG. 5A) and LP's 24 h lactic acid accumulation curve (FIG. 5B).

During the 24 hours bacterial growth, the inventors characterized also fermentations of the two microorganisms in terms of lactic acid production, and the results are shown in FIGS. 5A (LGG) and 5B (LP).

The results obtained by the present inventors demonstrate that both tested microorganisms can ferment the broth, reaching a final concentration of about $10^9$ CFU/ml and a final lactic acid production of about 20 g/L. The fermentation products have been inactivated, to kill the bacterial population thereby obtaining a postbiotic and then dried by a spray drying process.

The inactivated fermentation products obtained in form of powder by the dehydration process were then mixed to form a postbiotic composition (50:50 and 80:20 ratio of LP/LGG) and used for stimulation experiments on CaCo-2 cells to check the biological effect of the composition.

Figure 6:
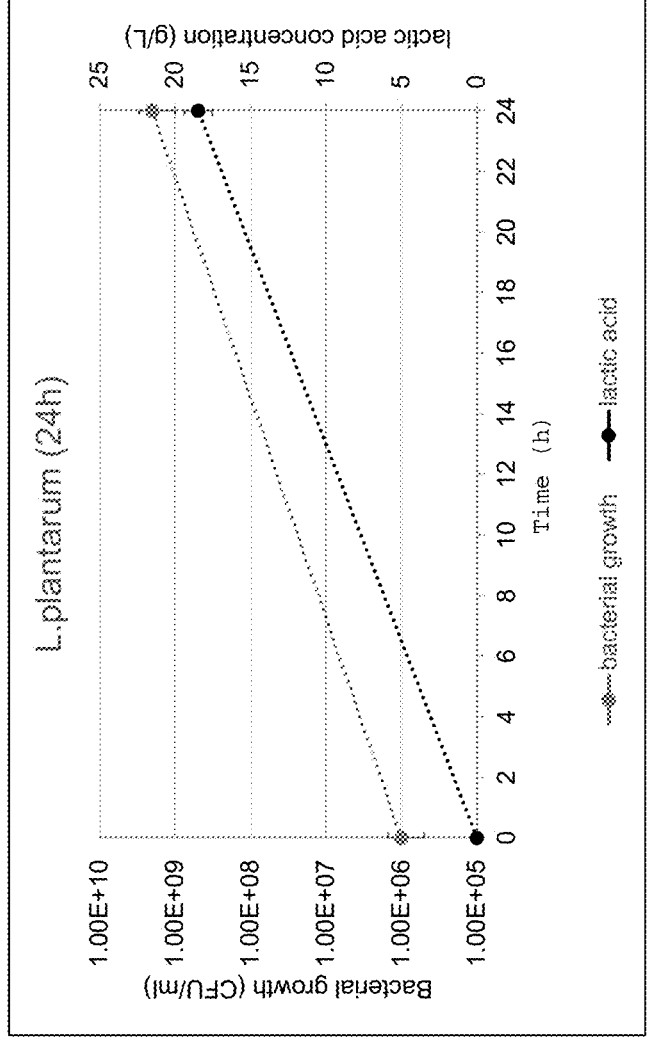
FIG. 6 illustrates bacterial growth and lactic acid production *Lacticaseibacillus plantarum* (Lpl) after 24 h of fermentation.
Figure 7:
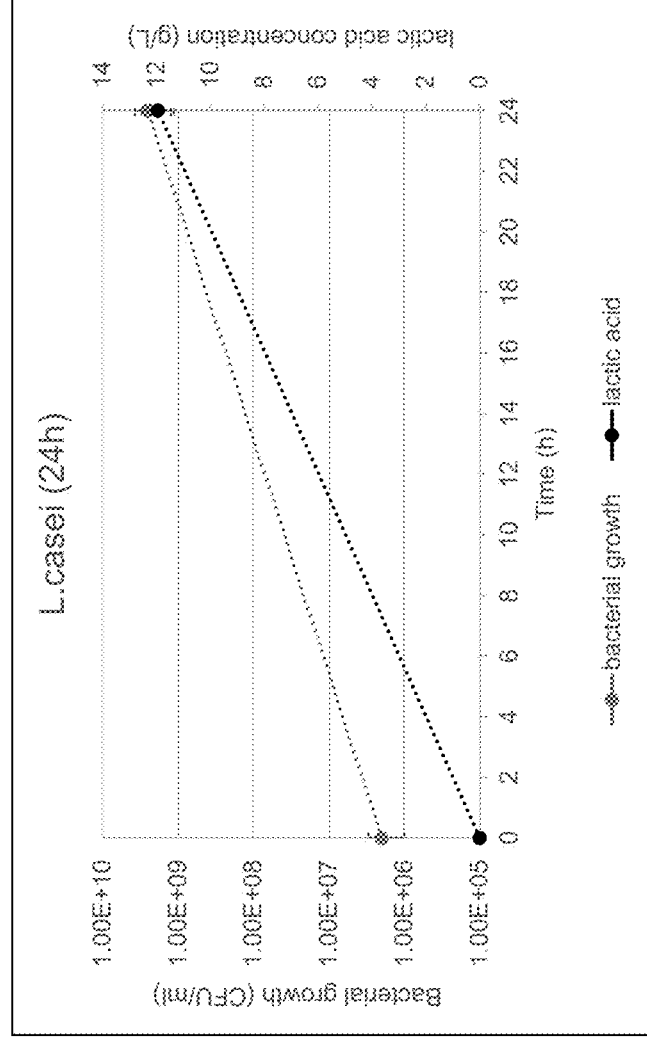
FIG. 7 illustrates bacterial growth and lactic acid production of *Lacticaseibacillus casei* (Lc) after 24 h of fermentation.

As for testing other *Lactobacillus* species, *Lacticaseibacillus plantarum* (Lpl) and *Lacticaseibacillus casei* (Lc) were fermented separately for 24 h. Their bacterial growth and lactic acid production curves obtained after 24 hours of fermentation are reported in FIGS. 6 and 7, respectively.

The results obtained demonstrated that both tested microorganisms ferment efficiently the broth, reaching a final concentration of $10^9$ CFU/ml and a final lactic acid concentration of 18.46 g/L and 11.95 g/L for Lpl and Lc, respectively.

The fermented broths were inactivated, to kill the bacterial population, thereby obtaining postbiotics and then dried by a spray drying process for the subsequent biological assay.

The inactivated fermented powders were then mixed to form a postbiotic composition (Lpl 50%+Lc 50%) and tested on Caco-2 cells.

Figure 8A:
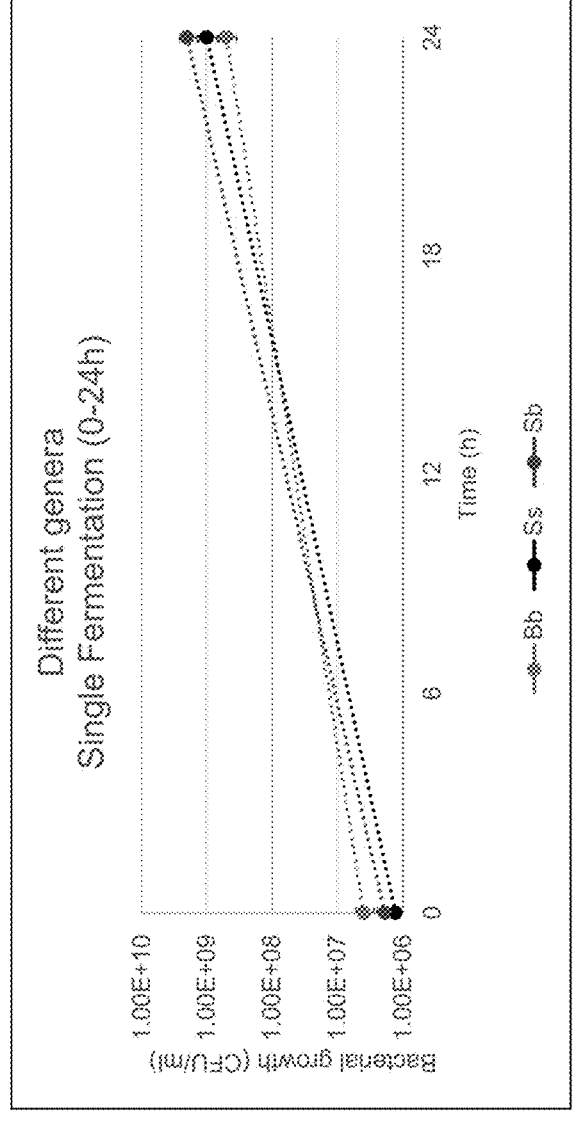
FIGS. 8A-8B illustrate the bacterial growth (FIG. 8A) and lactic acid production (FIG. 8B) of different microorganisms' genera (*Bifidobacterium bifidum*—Bb, *Streptococcus salivarius*—Ss, and *Saccharomyces boulardii*—Sb after 24 h of fermentation.
Figure 8B:
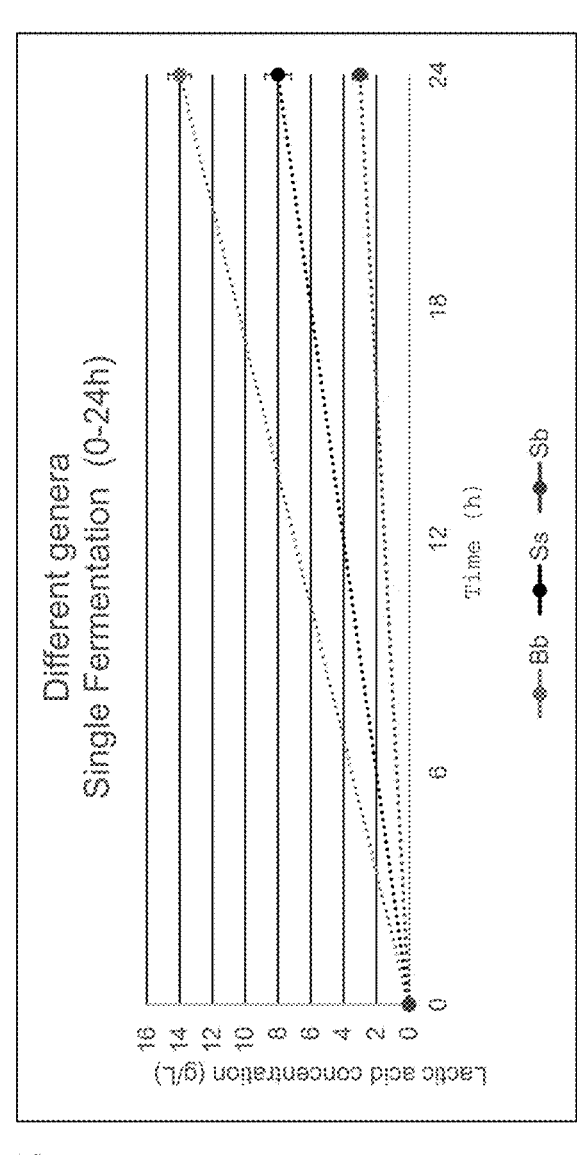

As for testing of other microorganisms' genera, *Bifidobacterium bifidum* (Bb), *Streptococcus salivarius* (Ss) and *Saccharomyces boulardii* (Sb) were fermented separately for 24 h. Their bacterial growth and lactic acid production curves obtained after 24 hours of fermentation are reported in FIGS. 8A and 8B.

The results obtained demonstrated that the three different microorganisms ferment efficiently the broth, reaching a final concentration of $10^8$ CFU/ml for Bb and $10^9$ CFU/ml for Ss and Sb; a lactic acid production of 14 g/L, 8 g/L and 3 g/L was detected after 24 h of fermentation for Bb, Ss and Sb, respectively.

The three fermented broths were subsequently inactivated, to kill the bacterial population, thereby obtaining postbiotics that were then dried by a spray drying process to be used in the biological assay; the inactivated fermented powders were then mixed to form a postbiotic composition (Bb 34%+Ss 33%+Sb 33%) and tested on Caco-2 cells.

Results obtained from multiple sequential fermentation (second embodiment of the method of the invention) are as follows:

A 48 h fermentation process was carried out using the *Lacticaseibacillus rhamnosus* (LGG) as first microorganism and the *Lacticaseibacillus paracasei* (LP) as the second microorganism. Briefly, after the first 24 hours of fermentation with LGG, a heat treatment was carried out to kill the bacteria biomass and subsequently LP was inoculated in the inactivated fermentation product without any addition of fresh nutrients to the broth. At the end of the second 24 h fermentation with LP, a heat inactivation step was carried out again.

Figure 9A:
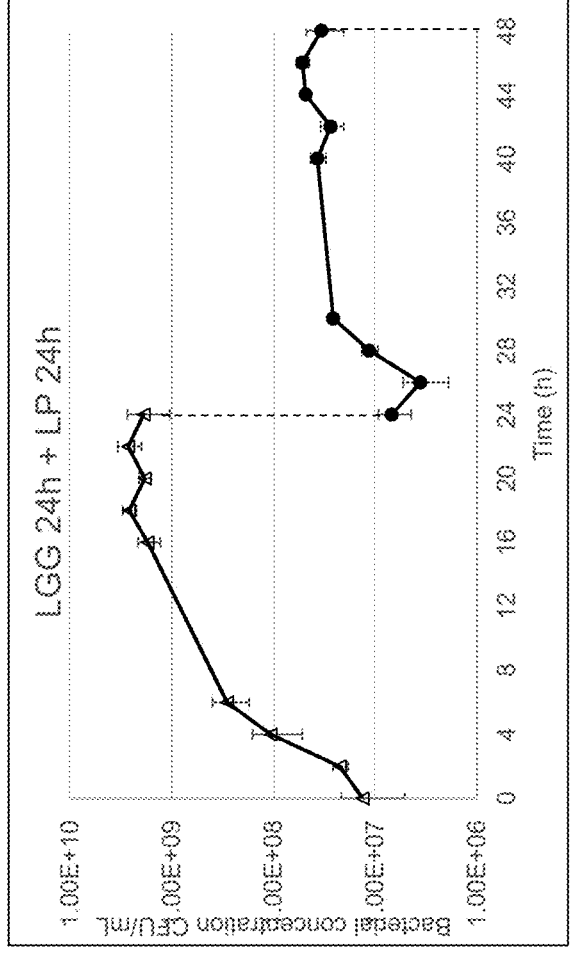
FIGS. 9A-9B illustrate the growth curve (FIG. 9A) and lactic acid accumulation curve (FIG. 9B) of a serial fermentation process that includes 24 hours with LGG and 24 hours with LP.

As shown in FIG. 9A, during the first 24 hours of fermentation, LGG showed a microbial growth ($\Delta$ log) of 2 log, with a final bacterial concentration of $1.9*10^9$ CFU/mL. After the inactivation of the first microorganism, the second microorganism (LP) was inoculated that showed a growth increase ($\Delta$ log) of about 1 log with a final bacterial concentration of $3.4*10^7$ CFU/mL.

Figure 9B:
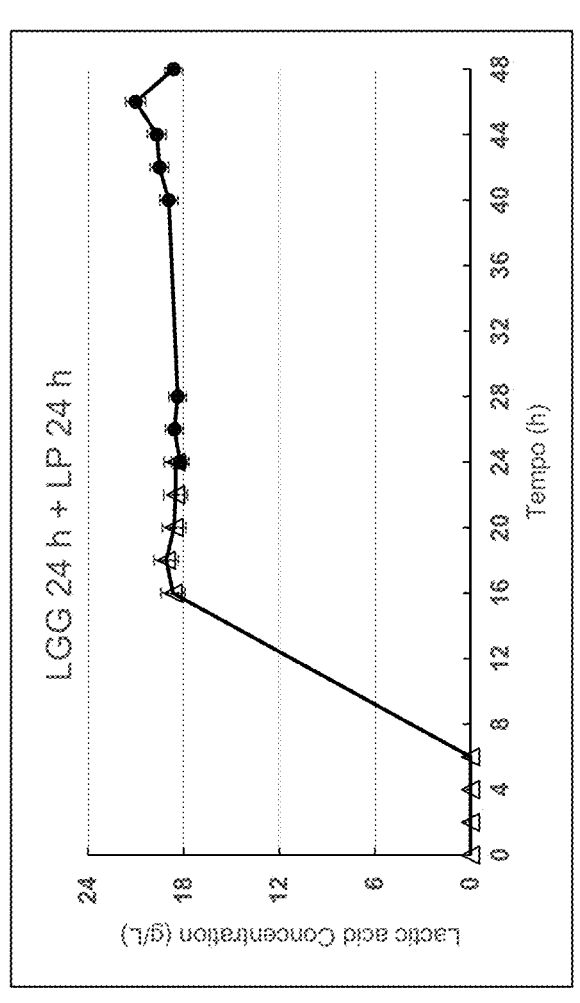

During the entire process 18 g/L of lactic acid was produced, almost entirely produced during the first 24 h fermentation (LGG); during the second stage of the process the lactic acid concentration remains approximatively constant (FIG. 9B).

Figures 10A, 10B:
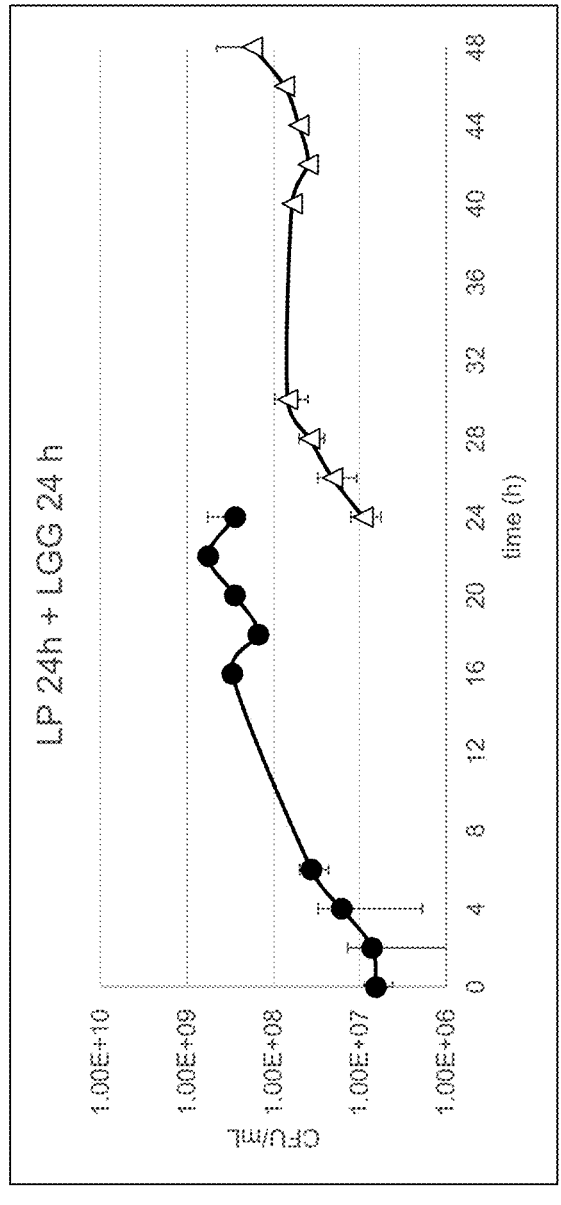
FIGS. 10A-10B illustrate the growth curve (FIG. 10A) and lactic acid accumulation curve (FIG. 10B) of a serial fermentation process that includes 24 hours with LP and 24 hours with LGG.

As further experiment, the method of the invention was carried out by inverting the order of inoculation of the fermenting microorganisms. The first inoculated microorganism, LP, fermented the culture broth for 24 h, subsequently the bacterial biomass was inactivated by a mild heat treatment. Without adding any nutrient to the fermented broth, the second 24 h fermentation was carried out by inoculating the second microorganism (LGG). At the end of the second 24 h of fermentation with LGG, heat inactivation was carried out again. During the first 24 hours of fermentation, LP had a microbial growth of 2 log ($\Delta$ log), with a final bacterial concentration of $5.7*10^8$ CFU/mL. After microbial killing, the inoculation of LGG was performed, starting with a bacterial concentration of 6 log. During the following 24 hours, an increase growth ($\Delta$ log) close to 2 log was observed, with a final bacterial concentration of $1.8*10^8$ CFU/mL (FIG. 10A). As shown in FIG. 10B, an overall production of about 20.5 g/L of lactic acid was observed during the process.

The present inventors carried out a further experiment on multiple sequential fermentation according to the invention, by assessing bacterial growth and lactic acid production upon fermentation with LGG for 6 hours, followed by fermentation with LP for 24 hours.

Figures 11A, 11B:
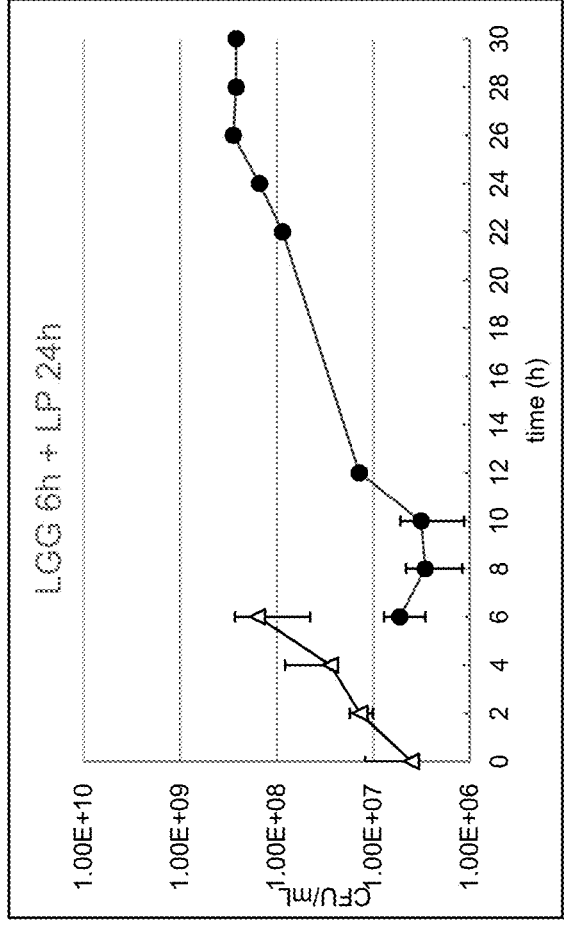
FIGS. 11A-11B illustrate the growth curve (FIG. 11A) and lactic acid accumulation curve (FIG. 11B) of a serial fermentation process that includes 6 hours with LGG and 24 hours with LP.

As shown in FIG. 11A, at the end of the 6 hours of fermentation LGG reached a bacterial load of $1.58*10^8$ CFU/ml, with an increase ($\Delta$ log) of about 2 logs compared to time 0. Also in this experiment, the second microorganism (LP) was added after the inactivation of the first fermenting microorganism and without the addition of any type of nutrients to the fermented broth. After 24 hour of fermentation, LP reached a bacterial growth of $2.6*10^8$ CFU/mL with a $\Delta$ log of 2 logs.

At the end of the above described sequential fermentations, a final concentration of 20 g/L of lactic acid was observed, with a maximum production of 22 g/L at 28 h (FIG. 11B).

The present inventors carried out once more a sequential fermentation experiment by inverting the order of microorganism inoculations. At the end of 6 hours fermentation, LP reached a bacterial load of $3.6*10^7$ CFU/mL. After 24 hours of processing, an increase of LGG growth of 2 log was observed, with a final bacterial concentration of $2.8*10^9$ CFU/mL (FIG. 12A).

Figures 12A, 12B:
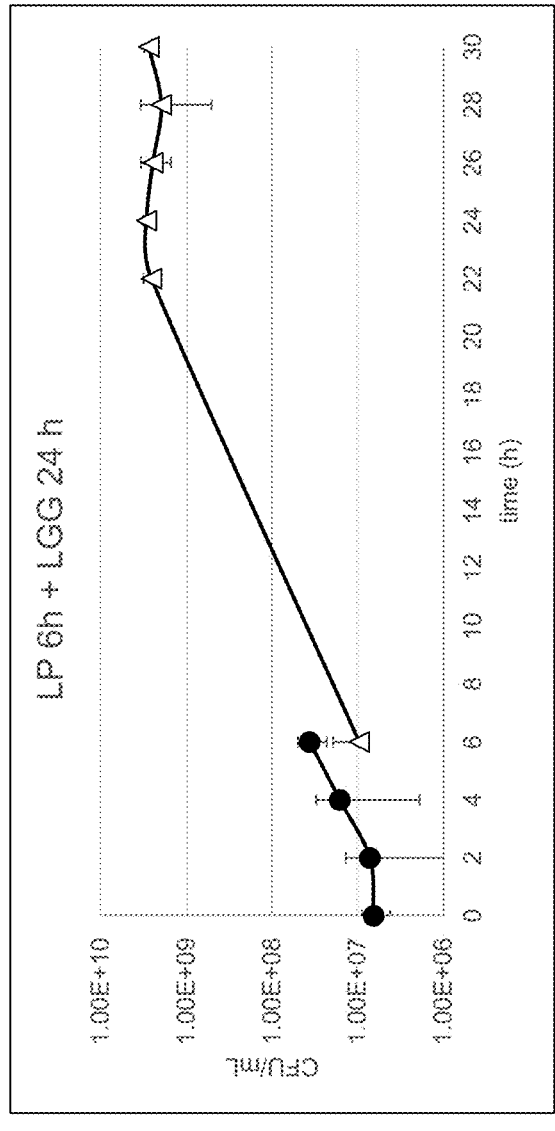
FIGS. 12A-12B illustrate the growth curve (FIG. 12A) and lactic acid accumulation curve (FIG. 12B) of a serial fermentation process that includes 6 hours with LP and 24 hours with LGG.

In this experiment, the production of lactic acid was at the same level as observed in the LP (24 h)+LGG (24 h) experiment, with a concentration of 20.7 g/L (FIG. 12B.

In all the above described assayed conditions of the method of the inventions, a microbial concentration sufficient to guarantee a functional effect is obtained (since higher than $10^7$ CFU/mL). The production of lactic acid is also around an average value of 20 g/L. As for other *lactobacillus* species, a fermentation of 30 h was carried out using the *Lacticaseibacillus plantarum* (Lpl) as first microorganism and *Lacticaseibacillus casei* (Lc) as second microorganism. Briefly, after the first 6 hours of fermentation with Lpl, a heat treatment was carried out to kill the bacteria biomass and subsequently Lc was inoculated in the inactivated fermented broth without any addition of fresh nutrients. At the end of 24 h of fermentation with Lc, a heat inactivation step was carried out again.

Figures 13A, 13B:
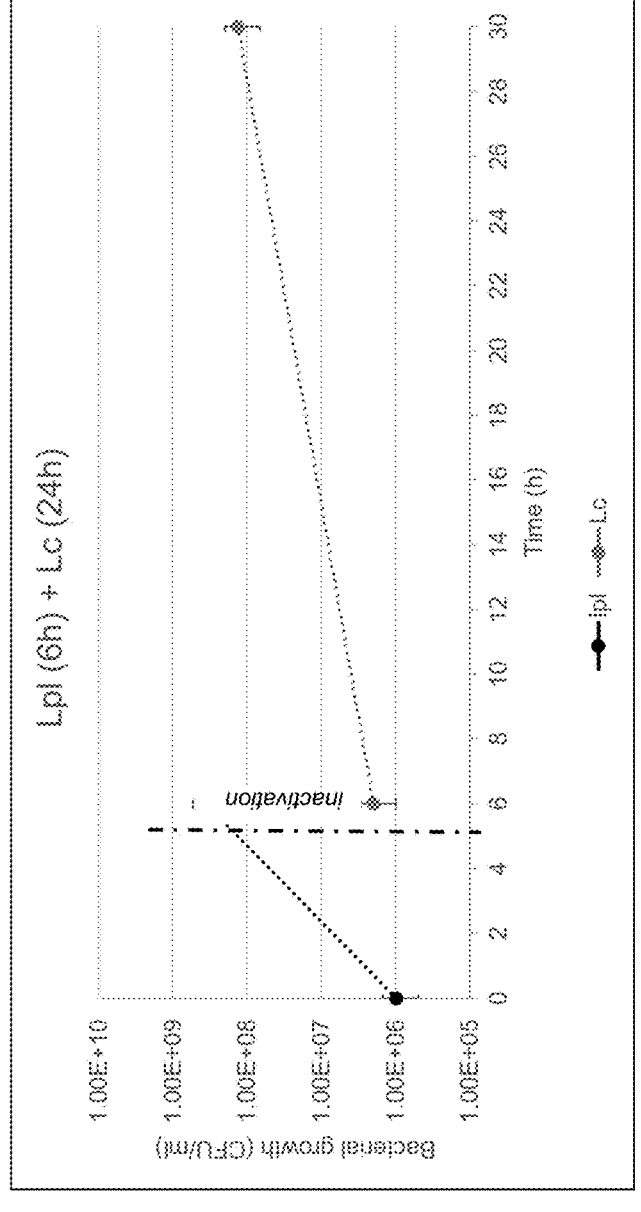
FIGS. 13A-13B illustrate the bacterial growth (FIG. 13A) and lactic acid production (FIG. 13B) of a serial fermentation process that includes 6 hours with Lpl and 24 hours with Lc.

As shown FIGS. 13A and 13B, after the first 6 hours of fermentation, Lpl showed a microbial growth increase ($\Delta$ log) of 2 log, achieving a bacterial charge of $3.6*10^8$ CFU/mL with a lactic acid concentration of 2 g/L (FIG. 13B); after, a mild heat treatment was carried to inactivate the first microorganism and the second microorganism (Lc) was inoculated in the fermented broth; Lc showed a growth increase ($\Delta$ log) of 2 log with a bacterial load of $1.34*10^8$ CFU/mL after 24 h of fermentation. During the entire process, 14 g/L of lactic acid was produced.

Figure 14A:
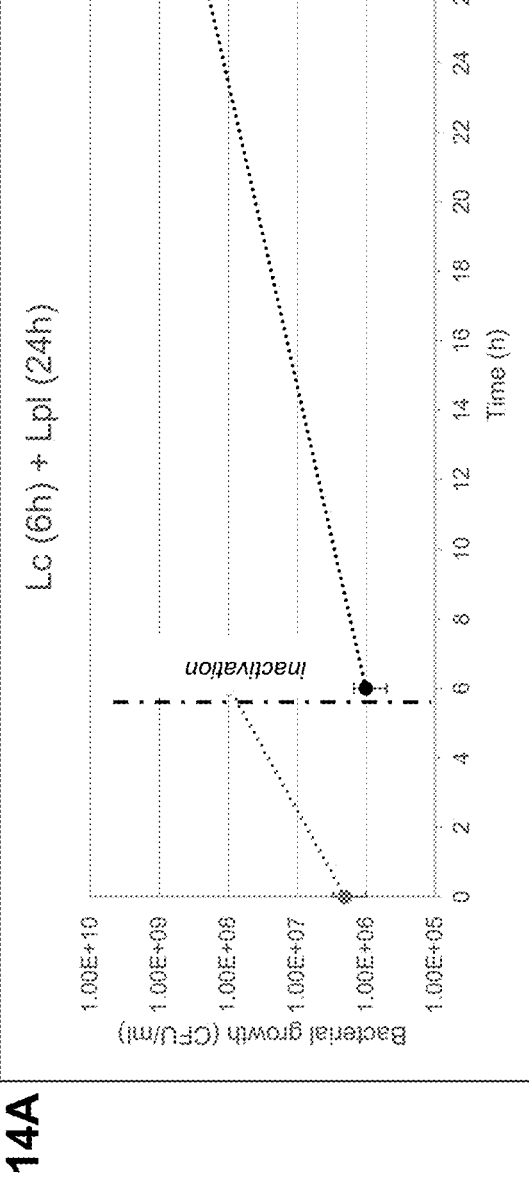
FIGS. 14A-14B illustrate the bacterial growth (FIG. 14A) and lactic acid production (FIG. 14B) of a serial fermentation process that includes 6 hours with Lc and 24 hours with Lpl.
Figure 14B:
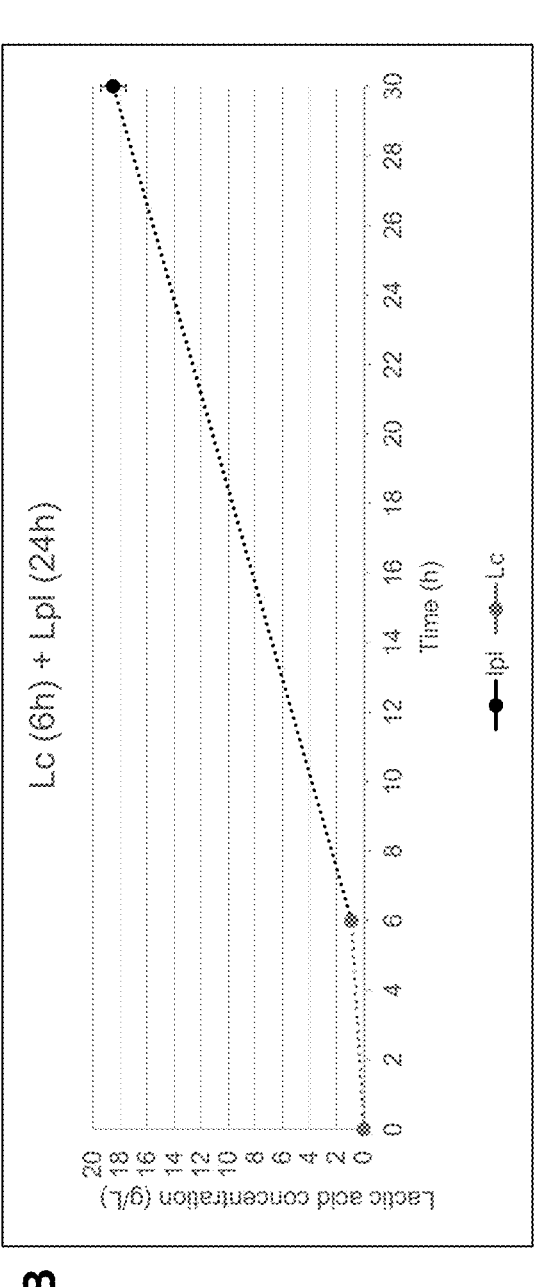

A further experiment was performed by inverting the order of inoculations of the fermenting microorganisms. The first inoculated microorganism, Lc, fermented the culture media for 6 h, subsequently, the bacterial biomass was inactivated by a mild heat treatment. Without adding any nutrients to the fermented broth, other 24 h of fermentation was carried out by inoculating the second microorganism, Lpl. At the end of the second fermentation, a heat inactivation was carried out again. As shown in the FIGS. 14A and 14B, during the first 6 hours of fermentation, Lc showed a microbial growth increase ($\Delta$ log) of about 2 log, with a final bacterial charge of $9.5*10^7$ CFU/mL and a lactic acid production of 0.9 g/L; subsequently a mild heat treatment was carried to inactivate the first microorganism. The second microorganism (Lpl) was inoculated in the fermented broth, showing a growth increase ($\Delta$ log) of 2 log with a bacterial charge of 5.6*10^8 CFU/mL after 24 h of fermentation. During the entire process, 18.5 g/L of lactic acid was produced.

As for testing of other genera, a fermentation process of 36 h was carried out using the *Bifidobacterium bifidum* (Bb) as first microorganism for 6 h of fermentation, the *Streptococcus salivarius* (Ss) as second microorganism for 6 h of fermentation and *Saccharomyces boulardii* (Sb) as third microorganism for 24 h of fermentation. Briefly, after the first 6 hours with Bb, a heat treatment was carried out to kill the bacteria biomass and subsequently Ss was inoculated in the inactivated fermented broth, without any addition of fresh nutrients; Ss fermented the broth for other 6 h. At the end of this period a heat inactivation step was carried out again. Sb was inoculated without any addition of fresh nutrients to the fermented broth and the third fermentation was carried out for 24 h. After this period a heat treatment to inactivate the bacterial biomass was carried out.

Figures 15A, 15B:
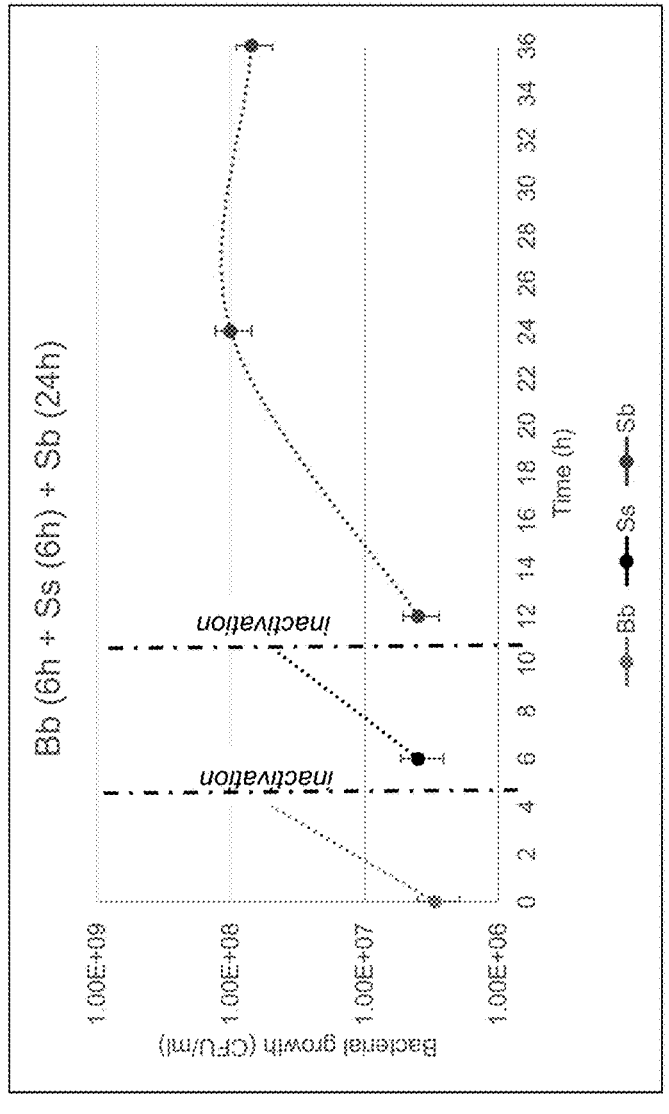
FIGS. 15A-15B illustrate the bacterial growth (FIG. 15A) and lactic acid production (FIG. 15B) of a serial fermentation process that includes 6 hours with Bb, 6 h with Ss and 24 h with Sb.

As shown in FIGS. 15A and 15B, during the first 6 hours of fermentation, Bb showed a microbial growth increase (Δ log) of 2 log, reaching a bacterial charge of 2.0*10^8 CFU/mL and a lactic acid concentration of 1.2 g/L; a mild heat treatment was carried to inactivate the first microorganism and the second microorganism (Ss) was inoculated; Ss showed a growth increase (Δ log) in 6 h of 2 log with a bacterial charge of 1.0*10^8 CFU/mL and a total lactic acid concentration of 2.1 g/L; an additional heat treatment was carried out to kill Ss' biomass and Sb was inoculated achieving a bacterial growth of 1.0*10^8 CFU/mL after 12 h of fermentation that was maintained more or less constant after other 12 h of process (7.0*10^7 CFU/mL). During the entire process (36 h), 7.8 g/L of lactic acid was produced.

The fermentation results demonstrated that all the bacteria tested (LP, LGG, Lpl, Lc, Bb, Ss and Sb), both for single fermentations and for the various combinations of the serial process, showed good microbial growth (reaching 8 and 9 logs CFU/ml), such that they could be considered to have probiotic properties (it is generally accepted that probiotic products should have a minimum concentration of $10^6$ CFU/mL or gram and that a total amount of $10^8$ to $10^9$ of probiotic microorganisms should be consumed daily to have a probiotic effect) with a good production of lactic acid.

Surprisingly, in the sequential fermentation method according to the invention, where the first microorganism consumes the nutrients of the broth, the second and eventually third inoculated microorganism can ferment effectively with a high production of biomass and lactic acid. Consequently, the above experiments prove that a "postbiotic broth" can be used as a fermenting medium for other microorganism ensuring an adequate metabolic activity.

Biological Results

Evaluation of Immune Biomarker Beta-Defensin-2 on Caco-2 Cells

The method according to the invention allows to obtain postbiotic compositions with significant bioactivities and high added value.

To assess the biological effect of the postbiotic composition according to the invention, the present inventors investigated the ability of postbiotic products, obtained by double fermentation of MRS broth, abatement and subsequent drying, to modulate innate immunity.

Figure 16:
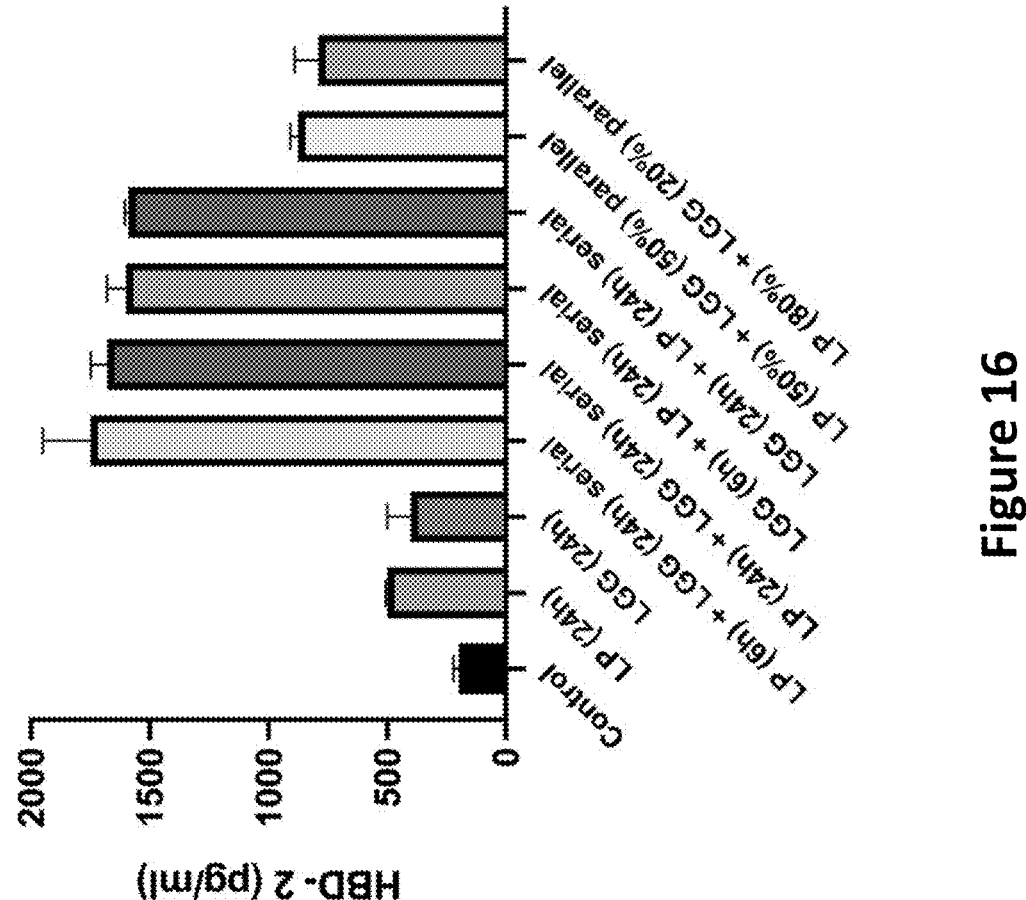
FIG. 16 illustrates the effect of postbiotics obtained from LP and LGG single fermentations, different combinations of the serial process and different composition of the parallel process on the HBD-2 peptide production in Caco-2 cells compared with the control, using ELISA test.

The postbiotic products obtained by parallel or serial fermentation of LP and LGG were used as a stimulus (at a dosage of 11.5 mg/ml) for Caco-2 cells (48 h). At the end of the stimulation, the concentration of HBD-2, used as a marker of innate immunity, was determined in the supernatant. An unstimulated (NT) supernatant was used as a control. In FIG. 16 are shown the results of HBD-2 concentration measurements in the supernatant of Caco-2 cells upon stimulation with postbiotic compositions produced according to the following methods: Controluntreated (NT); MRS fermented with LP alone for 24 h (LP (24 h)); MRS fermented with LGG alone for 24 h (LGG (24 h)); MRS serially fermented for 6 h with LP and then for 24 h with LGG (LP (6 h)+LGG (24 h) sequential); MRS serially fermented for 24 h with LP and then for 24 h with LGG (LP (24 h)+LGG (24 h) sequential); MRS serially fermented for 6 h with LGG and then for 24 h with LP (LGG (6 h)+LP (24 h) sequential); MRS serially fermented for 24 h with LGG and then for 24 h with LP (LGG (24 h)+LP (24 h) sequential); MRS fermented separately with LP and with LGG, inactivated, dried and mixed at 50% (LP (50%)+LGG (50%) parallel); MRS fermented separately with LP and with LGG, inactivated, dried and mixed 80%: 20% (LP (80%)+LGG (20%) parallel).

Similarly, postbiotics of other *Lactobacillus* spp were tested. Lpl individually fermented for 24 h (Lpl (24 h)), Lc individually fermented for 24 h (Lc (24 h)) of Lpl (24 h), Lc (24 h), Lpl (6 h)+Lc (24 h) resulting from the serial process, Lc (6 h)+Lpl (24 h) resulting from the serial process and Lc (50%)+Lpl (50%) resulting from the mixing of single fermentations (parallel process), were tested on Caco-2 cells to evaluate the production of HBD-2.

Caco-2 cells were stimulated for 48 hours with the 5 postbiotics mentioned above (with a dose of 11.5 mg/ml). Cells stimulated with culture medium alone were used as controls.

Figure 17A:
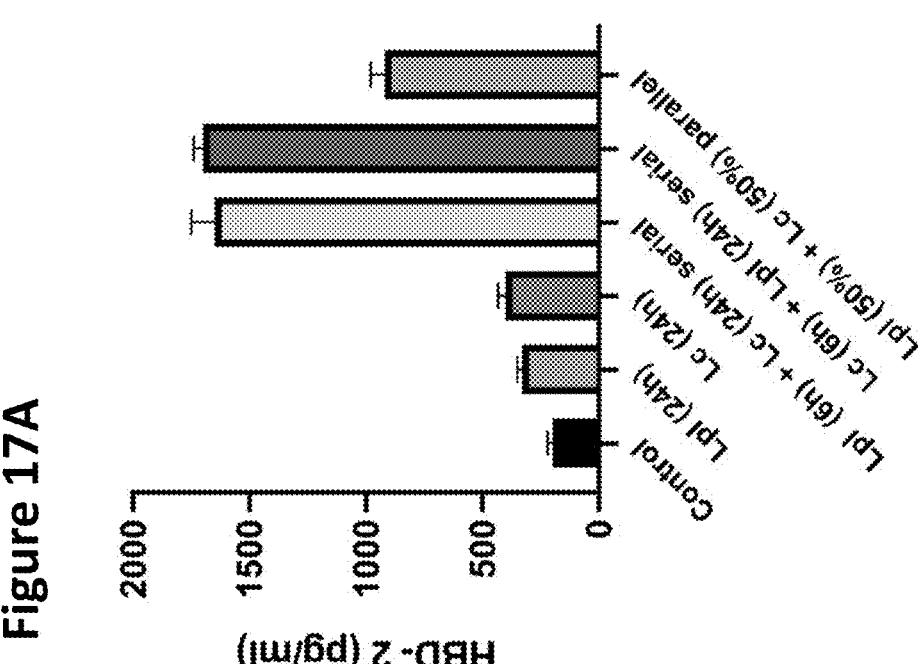
FIGS. 17A-17B illustrate the effect of postbiotics obtained from Lpl and Lc single fermentations, different combinations of the serial process and a single composition of the parallel process on the HBD-2 peptide production in Caco-2 cells compared with the control, using ELISA test (FIG. 17A).
Figure 17B:
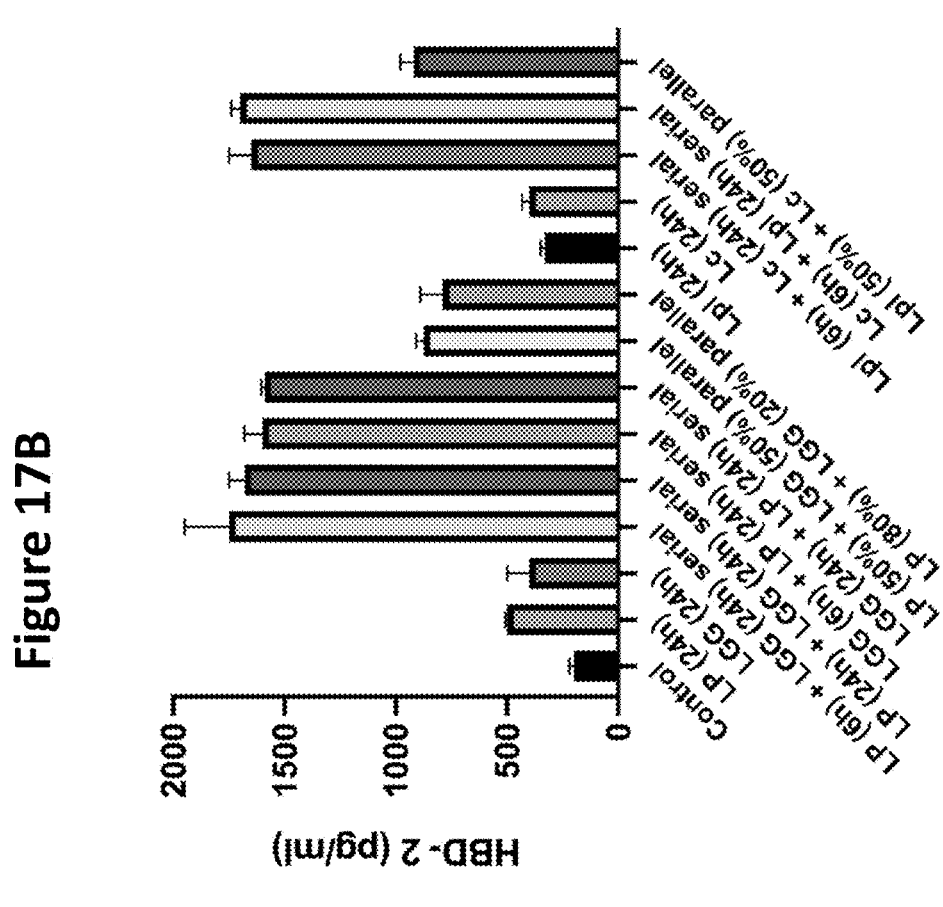

The biological results (FIGS. 17A and 17B) on CaCo-2 cells showed that postbiotics obtained from both serial and parallel process lead to a stimulation of innate immunity higher than that promoted by single fermentation. The serial process ensured a more marked production of HBD-2 compared to the parallel process.

As for testing with other microorganisms' genera, postbiotics of Bb individually fermented for 24 h (Bb (24 h)), Ss individually fermented for 24 h (Ss (24 h)), Sb individually fermented for 24 h (Sb (24 h)), Bb (24 h), Ss (24 h), Sb (24 h), Bb (6 h)+Ss (6 h)+Sb (24 h) resulting from the serial process, and Bb (34%)+Ss (33%)+Sb (33%) resulting from the mixing of single fermentations (parallel process), were tested on Caco-2 cells to evaluate the production of HBD-2.

Caco-2 cells were stimulated for 48 hours with the postbiotics mentioned above (with a dose of 11.5 mg/ml). Cells stimulated with culture medium alone were used as control.

Figure 18:
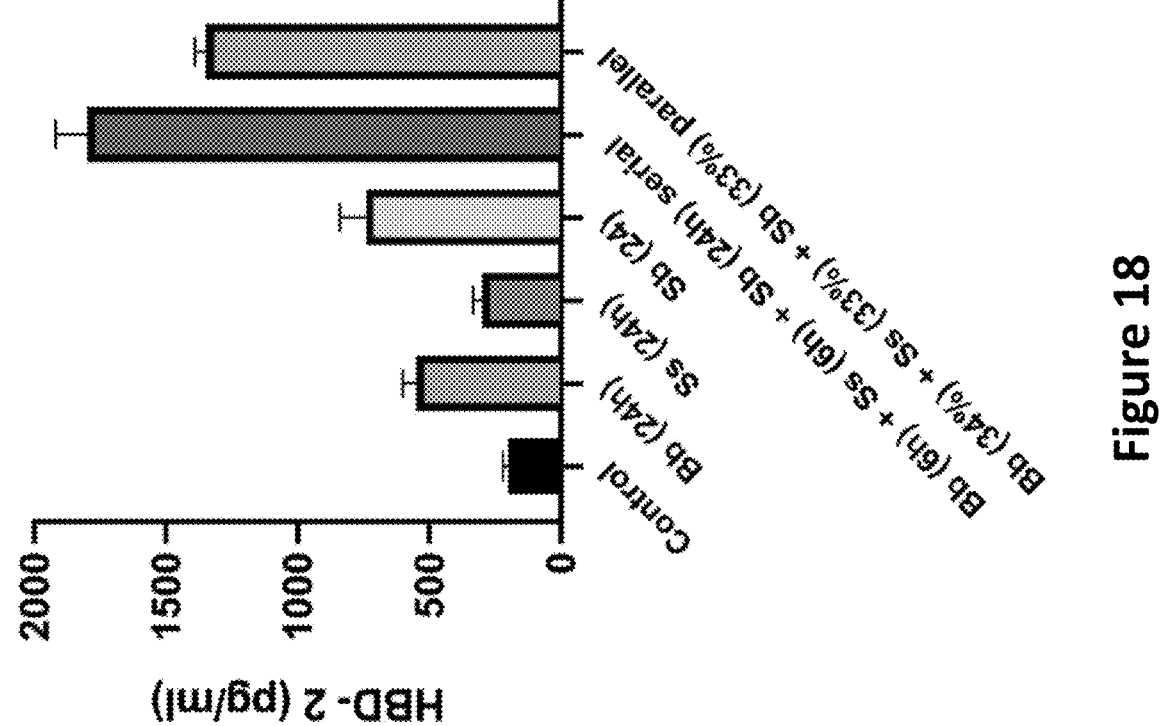
FIG. 18 shows the effect of postbiotics obtained from Bb, Ss and Sb single fermentations, from a single combination of serial process and a single composition of the parallel process on the HBD-2 peptide production in Caco-2 cells compared with the control, using ELISA test.

The biological results (FIG. 18) on CaCo-2 cells showed that postbiotics obtained from both sequential and parallel fermentations lead to a stimulation of innate immunity higher than that promoted by single fermentation. The sequential process ensured a more marked production of HBD-2 compared to the parallel process.

The biological results on CaCo-2 cells show that the method of the invention, either in the parallel fermentation embodiment or in the sequential fermentation embodiment using and combining different microorganisms' genera, leads to the production of a postbiotic composition that favor a synergistic effect, providing a stimulation of the innate immunity higher than that promoted by individual microorganisms. Of note, a difference between sequential and parallel fermentation according to the invention is observed: the parallel process ensured a double production of HBD-2 compared to the single microorganism, while for sequential fermentation the results tripled. Therefore, in the sequential fermentation embodiment, the method of the invention leads to a combined metabolism of the two or three microorganisms involved amplifying the biological response, probably allowing the production of new metabolites, which can promote a greater production of functional markers.

As regards parallel fermentations of LP and LGG, both formulations (LP50%+LGG50% and LP80%+LGG 20%) (50:50; 80:20 LP/LGG) showed a synergistic effect on HBD-2 without significant differences.

Expression of Intestinal Barrier Integrity Biomarkers on Caco-2 Cells

The integrity of the intestinal barrier plays a crucial role in protection against infections and many chronic non-communicable diseases, such as obesity, allergies, autoimmune diseases, cancer, and degenerative diseases of the central nervous system.

The effects on intestinal barrier system of postbiotics obtained from single fermentation of LP (LP (24 h)) and LGG (LGG (24 h)), and from the mixing of single fermentations (parallel process) (LP 80%+LGG 20%) were evaluated and compared to a commercial postbiotic. Cells stimulated with cell culture medium alone (without postbiotics) were used as a control.

Figures 19A, 19B:
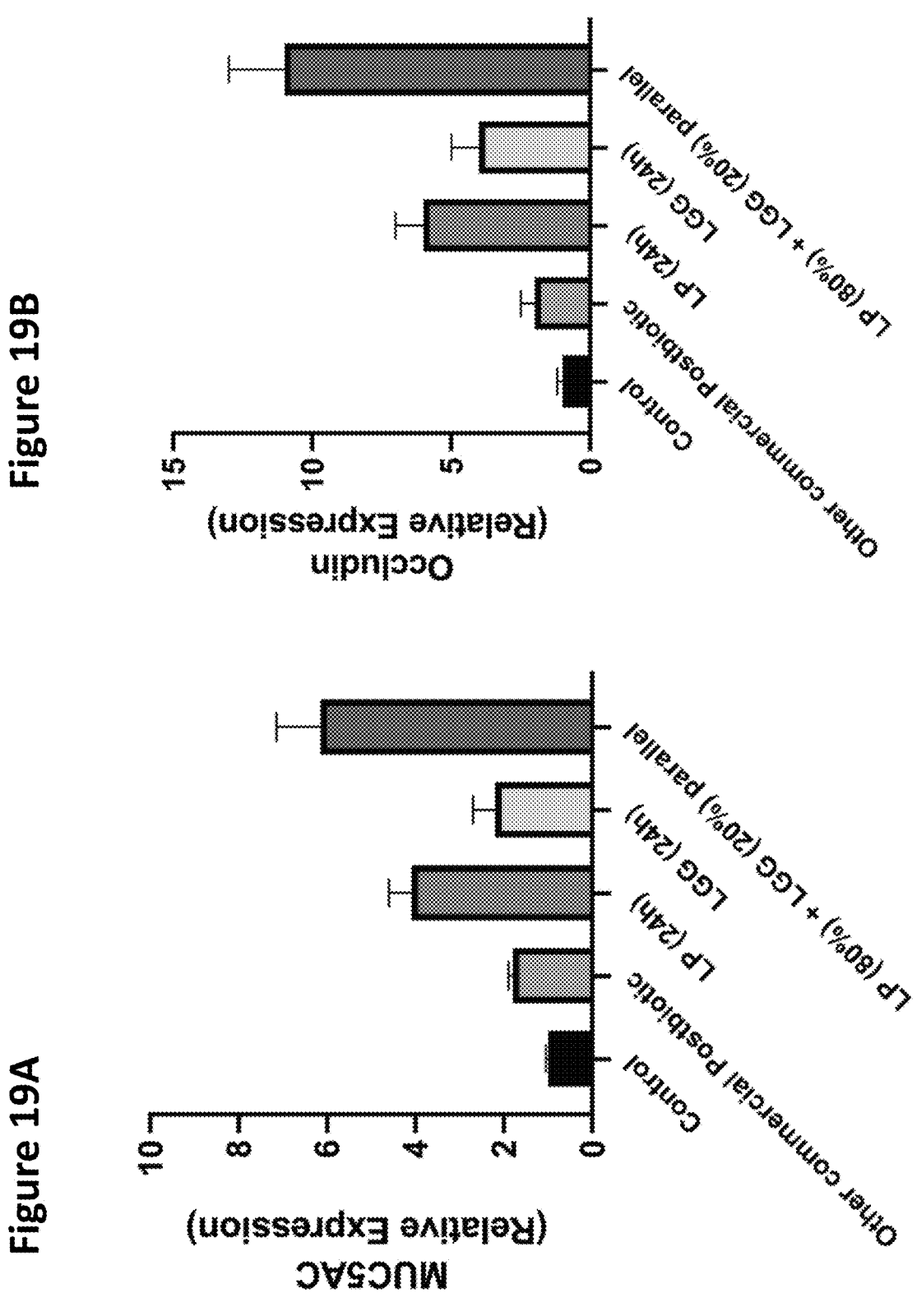
FIGS. 19A-19C illustrate the effect of postbiotics obtained from LP and LGG single fermentations and from the parallel process on the expression of the intestinal barrier integrity biomarkers MUC5AC (FIG. 19A), Occludin (FIG. 19B), and ZO-1 (FIG. 19C) in human enterocytes compared to the control and to a commercial postbiotic.
Figure 19C:
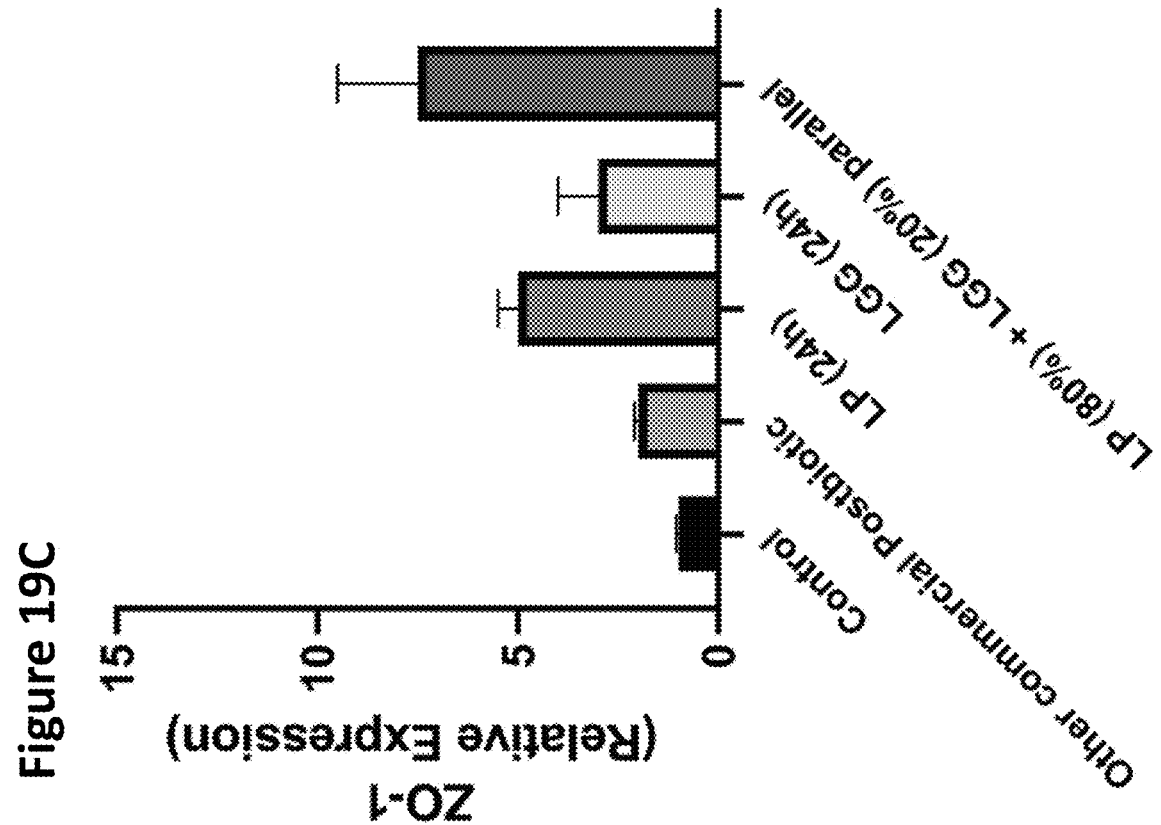

As shown in the FIG. 19, the incubation with the commercial postbiotic did not determine any effect on the three biomarkers (tight junction proteins, occludin and ZO-1, and epithelial mucus layer protein MUC5AC); on the contrary, LP (24 h) and LGG (24 h) were able to positively modulate all the biomarkers analyzed. Also in this case, the postbiotic composition LP 80%+LGG 20% obtained by the parallel process was able to determine a significantly greater stimulation effect than the other postbiotics on all the biomarkers analyzed.

Overall, the above results show that the methods of the invention obtain postbiotic compositions exhibiting unique biological characteristics compared to fermentation methods that make use of a single bacterium or multiple bacteria that propagate in the same matrix at the same time. These results may depend on multiple factors, including the absence of growth competition between bacteria and the absence of inhibition in the production of certain metabolites by others. Significant levels of certain biological activities cannot be achieved with a single bacterium and therefore such activities may be combined to obtain complementary or synergistic effects.

The methods according to the invention also obtain a biological activity with significantly lower dosages than traditional processes, limiting the quantitative use and/or obtaining more evident results at the same dosage, with undoubted economic and/or functional advantages.

Example 3: Composition of Postbiotic Capsules Comprising a Source of L-Tryptophan L-tryptophan is a proteinogenic amino acid and as such used for protein biosynthesis; besides this L-tryptophan is metabolized to compounds such as nicotinic acid mononucleotide, nicotinamide dinucleotide, and serotonin, each of which has specific biochemical functions and thereby affects physiology. L-tryptophan typically enters the body via normal dietary ingestion of L-tryptophan-containing proteins included in food stuffs. Additionally, L-tryptophan as amino acid can also be ingested in the form of dietary supplements.

Mammalian non-proteinogenic L-tryptophan metabolism occurs in mammalian cells as well as in select microbial cells; gut microbial L-tryptophan metabolism thereby contributes to the fecal as well as the circulating pool of L-tryptophan metabolites in mammals (Dodd D. et al., *Nature* 2017, 551(7682):648-652). Of note, some L-tryptophan metabolites, including indole-3 lactic acid (ILA) and indole-3 acetic acid (IAA), appear to be exclusively produced by gut microbes and not by host cells (Lamas B. et al., *Nat. Med.* 2016, 22(6):598-605). In line with this, fecal levels of IAA and L-kynurenine are drastically reduced in germ-free compared to conventional mice. Gut microbiota composition and L-tryptophan availability are therefore major determinants of bioavailability of these compounds.

Health effects of L-tryptophan metabolites are inferred by mechanistic studies, animal studies and by human association studies. Kynurenine and IAA are linked to psychological functions such as mood, appetite, and anxiety, supposedly via effects on neuroinflammation as well as L-tryptophan uptake via the blood-brain-barrier, and Trp-to-serotonin metabolization (Ogyu K. et al., *Neurosci. Biobehav. Rev.* 2018, 90:16-25 and Osadchiy V. et al., *PLOS One* 2018, 13(8): e0201772). Kynurenine promotes expansion of gut mucosal RORγt (+) IL-22(+) ILC3 cells, which in turn stimulate proliferation of mucus-producing goblet cells and thereby support gut barrier integrity (Qi H et al., *Commun. Biol.* 2019, 2:171). ILA has been described to protect against inflammatory bowel diseases through modulation of mucosal CD4+ T-cell differentiation (Cervantes-Barragan L. et al., *Lactobacillus reuteri* (*Limosilactobacillus reuteri*) induces gut intraepithelial CD4(+) CD8alphaalpha (+) T cells. *Science* 2017, 357(6353):806-810). Some L-tryptophan metabolites are agonists of the arylhydrocarbon receptor (AhR) (Krishnan S. et al., *Cell Rep.* 2018, 23(4): 1099-1111), a transcription factor that regulates the expression of genes involved in xenobiotics metabolism, immunity, the expression of interleukin-22, in various organs, including the liver, gut, lung, and brain. AhR thereby affects various health conditions, e.g. chronic-inflammatory diseases of the gut (colitis), lung (e.g. asthma bronchiale), and brain (e.g. major depressive disorder). Other L-tryptophan metabolites like indole-3-propionic acid reportedly engage the pregnane-X receptor and thereby regulate intestinal barrier function (Venkatesh M. et al., *Immunity* 2014, 41(2):296-310). Combining L-tryptophan with the postbiotic compositions described herein may therefore provide beneficial metabolization of L-tryptophan in a subject.

A postbiotic composition prepared according to a method of the invention can be prepared with L-tryptophan for filling into hydroxypropyl methyl-cellulose (HPMC) capsules (size 00 or other). L-tryptophan may be added as a free amino acid or a modification thereof, or as a dipeptide or in a protein. The postbiotic composition is prepared with either 50 mg, 250 mg, or 800 mg of L-tryptophan and filled into HPMC capsules. The capsules may further contain amino acids selected from L-ornithine, L-aspartate, L-lysine, and L-arginine. Alternatively, the capsules may be formulated by using pH-dependent polymers such as cellulose acetate phthalates (CAP), hydroxypropyl methyl-cellulose phthalate (HPMCP) 50 and 55, copolymers of methacrylic acid and methyl methacrylate (e.g., Eudragit® S 100, Eudragit® L, Eudragit® FS, and Eudragit® P4135 F).

The capsules may further contain further carbohydrate ingredients, selected from arabinoxylans, barley grain fibre, oat grain fibre, rye fibre, wheat bran fibre, inulins, fructooligosaccharides (FOS), galactooligosaccharides (GOS), resistant starch, beta-glucans, glucomannans, galactoglucomannans, guar gum and xylooligosaccharides.

The capsules may further contain one or more plant extracts, selected from ginger, cinnamon, grapefruit, parsley, turmeric, *curcuma*, olive fruit, *Panax ginseng*, horseradish, garlic, broccoli, *spirulina*, pomegranate, cauliflower, kale, cilantro, green tea, onions, and milk thistle.

The capsules may further contain astaxanthin, charcoal, chitosan, glutathione, monacolin K, plant sterols, plant stanols, sulforaphane, collagen, hyalurone, and/or phosphatidylcholine.

The capsules may comprise further vitamins selected from biotin, vitamin A, vitamin B1 (thiamine), vitamin B2 (riboflavin), vitamin B3 (niacin), vitamin B5 (pantothenic acid), vitamin B9 (folic acid or folate), vitamin C (ascorbic acid), vitamin D (calciferols), vitamin E (tocopherols and tocotrienols) and vitamin K (quinones) or minerals selected from sulfur, iron, chlorine, calcium, chromium, cobalt, copper, magnesium, manganese, molybdenum, iodine, selenium, and zinc.

Example 4: Effects of *L. paracasei* NPB01 Cell Wall Polysaccharides on Cell Viability, Immune Response and Epithelial Barrier in Human Enterocytes

*Lacticaseibacillus paracasei* is a gram-positive, homofermentative species of lactic acid bacteria commonly used in fermented foods and in postbiotic products (Kiousi D E et al., Front Microbiol. 2022; 13:922689). *L. paracasei* strains have been isolated from several environments, including dairy products, plants, and human gastrointestinal tract. The consumption of foods fermented with *L. paracasei* strains could confer beneficial effects on human health (Bengoa A A et al., Foods. 2021; 10(10):2239). This study investigated the structure of the cell wall polysaccharides of a new *L. paracasei* strain isolated from human gut microbiome, named *L. paracasei* NPB01, and tested their effects on cell viability, immune response and epithelial barrier in human enterocytes. The results of this study further inform on the safety profile of postbiotic compositions comprising *L. paracasei* NPB01.

Methods

Bacterial Culture

*L. paracasei* NPB01 (DSM 34367), a gram positive homofermentative bacterium, was stored at −80° C. in MRS broth (Oxoid, Basingstoke, UK) with 20% glycerol. Before each fermentation it was revitalized using fresh MRS broth (1:10) for 24 h at 37° C., and a bacterial concentration of $10^8$ CFU/mL was found at the end of the revitalization.

The revitalized bacterium was then used as inoculum (1% v/v) for fermenting 1 L of fresh MRS broth. The fermentation was carried out for 24 h at 37° C. and at the end of the process a concentration of $10^8$ CFU/mL was found. The postbiotic was obtained by inactivating the bacterium at 85° C. for 20 s and the product was stored as a freeze-dried composition.

Bacterial Cell Wall Polysaccharides Extraction

*L. paracasei* postbiotic-derived polysaccharides were extracted as previously described (Vinogradov, E V et al., Carbohydr. Res. 2015, 413:93-99). The pellet obtained was suspended in 20 mL of water and extracted with 50% n-butanol, stirring at room temperature for 1 h. The organic phase was discarded, and the aqueous phase was deproteinated by addition of 5% TCA, stirring at 4° C. for 48 h. After that, the suspension was centrifuged (9000 rpm, 15 min, 4° C.) and an aqueous solution of 50% HF was added to the pellet, stirring for 48 h at 4° C. Finally, the suspension was centrifuged (7500 rpm, 30 min, 4° C.) and the supernatant was freeze-dried, giving a final yield of 0.79 mg/g of dried cells.

In the second step, bacterial glycans were extracted. Polysaccharides (starting from 2 g of pellet) were suspended in 30 mL of water and autoclaved (sterilizing cycle at 120° C.×20 min). The supernatant obtained after a centrifugation (8000 rpm×10 min, 4° C.) was filtered on a 0.45 μm filter and freeze-dried. The crude product was obtained with a final yield of 333 mg/g of bacterial cells.

Bacterial Glycans Purification

The crude postbiotic product was purified through a combination of chromatographic techniques. It was firstly used a size exclusion chromatography on Sephacryl HR-300 resin (1.5×45 cm, Cytiva 17-0599-01), packed and eluted with ammonium bicarbonate 50 mM, and the eluate was monitored by a refractive index detector. Next, an anion exchange chromatography on Q-sepharose fast-flow (1×1.5 ml, Cytiva 17-0510-01) was performed to separate the mixture of teichoic acid and capsule polysaccharide 1 (CPS-1) and, generally, to obtain the pure glycans, without nucleic acids contaminants. The elution was done with a stepwise gradient of NaCl (10, 100, 200, 400, 700, and 1000 mM); the teichoic acid was eluted with an NaCl gradient of 200 mM to 1 M. Each solution was concentrated by freeze-drying and desalted on Biogel P10 (1.5×10.5 ml), ran in water, and the eluate was monitored by a refractive index detector.

GLC-MS Analysis

Compositional analysis of *L. paracasei* postbiotic derived polysaccharides was performed by deriving them into acetylated O-methyl glycosides. After that, the absolute configuration of the monosaccharides was determined by analyzing their acetylated 2-O-octyl derivatives obtained by the reaction with an optically pure alcohol (R-(−)-octanol). Identification of the derivatives was inferred by GLC-MS analysis by comparing the retention time of the peaks in the sample with those from the in-house built standards (acetylated monosaccharides functionalized with pure octanol and its racemic mixture). The sugar linkage pattern of the capsule polysaccharide 2 (CPS-2) was defined by the partially methylated and acetylated alditols method (De Castro, C. et al., Methods Enzymol. 2010; 480:89-115). Finally, all these derivatives were analysed by using a GLC-MS Agilent Technologies 7820A (Santa Clara, CA, USA) equipped with a mass selective detector 5977B, an automatic injector 7693A and a HP-5 ms capillary column (Agilent, 30 m×0.25 mm i.d., 0.25 mm as film thickness, flow rate 1.2 ml/min, He as carrier gas). Electron impact mass spectra were recorded with ionization energy of 70 eV. The temperature program used was: 150° C. for 3 min, 150 up to 280° C. at 3° C./min, 300° C. for 5 min.

Acetylated O-methyl Glycosides

The polysaccharide sample (0.2 mg) was treated with 1 ml HCl/MeOH (1.25 M, 80° C., 16 h) followed by an acetylation step with 50 ml acetic anhydride in 100 ml pyridine (80° C., 30 min). The phosphodiester bond of the teichoic acid was first hydrolysed with 50 ml of HF 50% at 25° C. for 5 h.

Acetylated Octyl Glycosides (OAG)

*L. paracasei* postbiotic derived polysaccharides were treated with 100 mL of R-(−)-octanol and 15 mL of acetyl chloride at 60° C., O.N. Octanol excess was eliminated under air flux. Finally, the octyl glycosides were acetylated by adding 100 mL of pyridine and 50 mL of acetic anhydride at 80° C. for 30 min.

Partially Methylated Alditols Acetates (AAPM)

The polysaccharide sample (0.5 mg) was dissolved in anhydrous DMSO (1 mL) and a spun of spatula of powdered NaOH was added. The suspension was stirred at RT for 4 h, sonicating often to facilitate the dissolution of NaOH in DMSO. After that, the deprotonated alcoholic groups were methylated with 200 ml of $CH_3I$, left stirring at 25 C, 17 h. The solution was extracted with $H_2O/CHCl_3$ (3:1 v/v) five times, by centrifuging at 2500 rpm for 3 min and replacing the top layer with $H_2O$ each time. Then, the sample was hydrolysed with 200 ml of trifluoroacetic acid 2 M, at 120° C. for 2 h. After that, the anomeric function was marked and reduced by adding the tip of a small spun of $NaBD_4$ and 200 ml of EtOH. The sample was kept capped at 25 C for 1 h. The $NaBD_4$ excess was destroyed with few drops of glacial AcOH, subsequently neutralized with MeOH. Finally, sample was acetylated with acetic anhydride (50 ml) and pyridine (100 ml).

NMR Spectroscopy $^1H$ and 2D NMR spectra were recorded using a Bruker 600 MHz and a Bruker 1.2 GHz spectrometers, equipped with an inverse cryoprobe with gradients along the z axis. The samples were solved in 550 mL of $D_2O$ and the spectra were calibrated with internal acetone ($d_H$=2.225 ppm; $d_C$=31.45 ppm). Total Correlation Spectroscopy (TOCSY) and Nuclear Overhauser Enhancement Spectroscopy (NOESY) experiments were performed using data sets (t1× t2) of 2048× 512 points. Heteronuclear Single-Quantum Coherence (HSQC) and Heteronuclear Multiple Bond Correlation (HMBC) experiments were performed in the $^1H$-detection mode by single-quantum coherence with proton decoupling in the $^{13}C$ domain using data sets of 2048×512 points. HSQC was performed using sensitivity improvement and the phase-sensitive mode using echo/antiecho gradient selection, with multiplicity editing during the selection step. HMBC was optimized on long-range coupling constants, with a low-pass J filter to suppress one-bond correlations, using gradient pulses for selection, and a 60 ms delay was used for the evolution of long-range correlations. HMBC spectra were optimized for 6-15 Hz coupling constants. For transformation, the data matrix in both homo- and heteronuclear experiments was extended to 4096×2048 points and transformed by applying a qsine or a sine window function (Speciale I. et al., Carbohydr. Polym. 2022; 277:118885).

Spectra of the mixture of TA+CPS-1 were acquired at 298 K. TOCSY and NOESY mixing time was set to 100 and 200 ms, respectively, and were recorded, along with COSY experiment, with 24 scans. 100 scans were recorded for HMBC and HSQC-TOCSY and 60 for HSQC experiments. Spectra of the CPS-1 pure isolate was recorded at 315 K, with a number of scans of 32 for TOCSY and 70 for HSQC experiment. TOCSY mixing time was set to 100 ms. CPS-2 spectra were recorded at 293 K. TOCSY and NOESY mixing time was set to 100 and 200 ms, respectively, and 16 scans for each one and for COSY spectrum were recorded. 128, 512 and 192 scans were acquired for HSQC, HMBC and HSQC-TOCSY spectrum, respectively. All the spectra were transformed and analyzed with Bruker Topspin NMR DATA analysis software.

Human Enterocyte Cell Line and Cell Assays

Caco-2 cells (ATCC, Middlesex, United Kingdom; accession number HTB-37) were grown in Dulbecco modified Eagle medium with a high glucose concentration (4.5 g/L) and L-glutamine, supplemented with 10% FBS, 1% nonessential amino acids, 1% sodium pyruvate, and 1% penicillin/ streptomycin (Thermo Fisher Scientific). The cells were incubated at 37° C. in a humidified atmosphere containing 5% carbon dioxide. The culture medium was changed every 2 days.

Caco-2 cells were stimulated after 15 days post-confluence with four different concentrations (1, 10, 100 and 1000 µg/ml) of pelleted L. paracasei NPB-01 postbiotic, or with the pure CPS-1, CPS-2, and TA for 48 h. Cells exposed to only medium were used as negative control (NT). Afterward, the cells were harvested and stored at −20° C. for further use.

The toxicity of L. paracasei NPB-01 postbiotic, CPS-1, CPS-2, and TA was checked by trypan blue exclusion test, by counting the number of viable Caco-2 cells with and without the treatment at known concentrations (1 to 1000 mg/ml) as previously reported (W. Strober. Curr. Protoc. Immunol. 111 (1) (2015), p. A3-B24). An aliquot of cell suspension was mixed gently with equal volume of 0.2% Trypan blue dye (0.5% in PBS) and kept at room temperature for 3 min. The live and dead cells were counted with a hemocytometer on an inverted microscope.

Cathelicid LL-37, an innate immunity compound able to exert an antimicrobial action against fungal, bacterial, and viral pathogens (Ridvard K E and Overhage J. Antibiotics. 2021; 10(6):650), was selected as an immune response biomarker. Occludin, a major peptide involved in the regulation of the tight junctions' network (Brunner J et al. Adv. Drug Deliv. Rev. 2021:171:266-288), was selected as a biomarker of epithelial barrier regulation.

The expression of LL-37 and occludin was determined by Quantitative Real-Time PCR. Briefly, total RNA was extracted from stimulated Caco-2 cells with TRIzol reagent (Gibco BRL, Paisley, UK). RNA samples were analysed using the NanoDrop 2000c spectrophotometer (Thermo Scientific) and purity was verified by A260/280 and A260/230 absorbance ratios. RNA reverse transcribed in cDNA with a High-Capacity RNA-to-cDNA™ Kit (Life Technologies, Waltham, MA, USA) according to the manufacturer's instructions. Complementary DNA (cDNA) was stored at −80° C. until use. Quantitative real-time PCR (qRT-PCR) analysis was performed using Taqman Gene Expression Master Mix (Applied Biosystems, Vilnius, Lithuania) to evaluate the expression of LL-37 (Hs00189038_m1) and occludin (Hs05465837_g1). The TaqMan probes for these genes were inventoried and tested by Applied Biosystems manufacturing facility (QC). Data were analysed using the comparative threshold cycle method. The glucoronidase beta (GUS-B) gene was used to normalize the level of mRNA expression (TaqMan probes: Hs00939627_m1).

Statistical Analysis

The Kolmogorov-Smirnov test was used to determine whether variables were normally distributed. Descriptive statistics are reported as means and standard deviations for continuous variables when data were normally distributed. Differences among groups were compared by one-way ANOVA test. Differences among continuous variables were compared by the independent sample t-test. Differences were considered statistically significant at $p<0.05$. All data were collected in a dedicated database and analyzed by a using GraphPad Prism 7.

Results

Isolation and Identification of L. paracasei Polysaccharides

The polysaccharide material was isolated from the postbiotic derived from L. paracasei MRS fermentation. The pellet was suspended in water and extracted by heat treatment (120° C., 20 min). The crude postbiotic product was present in solution after centrifugation.

Afterward, the crude glycans underwent several steps of purification by size-exclusion and anion-exchange chromatography. Through size-exclusion chromatography on Sephacryl HR-300, four main fractions were separated (FIG. 20A), and their profiles were analysed by $^1H$ NMR (FIG. 20B); two important fractions containing polysaccharides were identified by this purification, RBC/16/$A_0$ and RBC/

16/A. RBC/16/A$_0$ was eluted from the size-exclusion chromatography in the flatline of the chromatogram and it represents the *L. paracasei* CPS (CPS-1) with a higher molecular weight (MW) with respect to the RBC/16/A fraction (CPS-2).

Both fractions RBC/16/A$_0$ and RBC/16/A were further purified by anion-exchange chromatography on Q-sepharose fast-flow, eluting with an increasing gradient of NaCl, and each obtained fraction was subsequently desalted on Biogel P-10 resin and eluted in pure water. Finally, from the fraction RBC/16/A$_0$ two different polymers were isolated, a teichoic acid (TA) and a capsular polysaccharide (CPS-1), respectively, whereas from the fraction RBC/16/A a second capsular polysaccharide (CPS-2) was obtained. Specifically, the teichoic acid was eluted with a final yield of 0.24 mg/g$_{dried-cells}$, while CPS-1 and CPS-2 were eluted a final yield of 8 mg/g$_{dried-cells}$ and 56 mg/g$_{dried-cells}$, respectively. Therefore, among the three glycans, the CPS-2 was the most abundant.

The structure of the *L. paracasei* glycans was determined by analyzing the complete set of homo- and heteronuclear 2D NMR experiments (COSY, TOCSY, NOESY, $^1$H-$^{13}$C HSQC, $^1$H-$^{13}$C HMBC). The spin system of each residue was assigned by COSY and TOCSY spectra, while $^1$H, $^{13}$C HSQC spectrum was used to assign the carbon chemical shift values.

For CPS-1 and TA, the total set of 2D NMR spectra was acquired in their mixed state. Purification by anion-exchange chromatography was subsequently performed, and the comparison of the $^1$H, $^{13}$C HSQC (FIG. 21A) and the proton (FIG. 22B) spectra of the mixture with those of the pure glycans (FIGS. 22A and 22C), confirmed their purity.

Figures 20A, 20B:
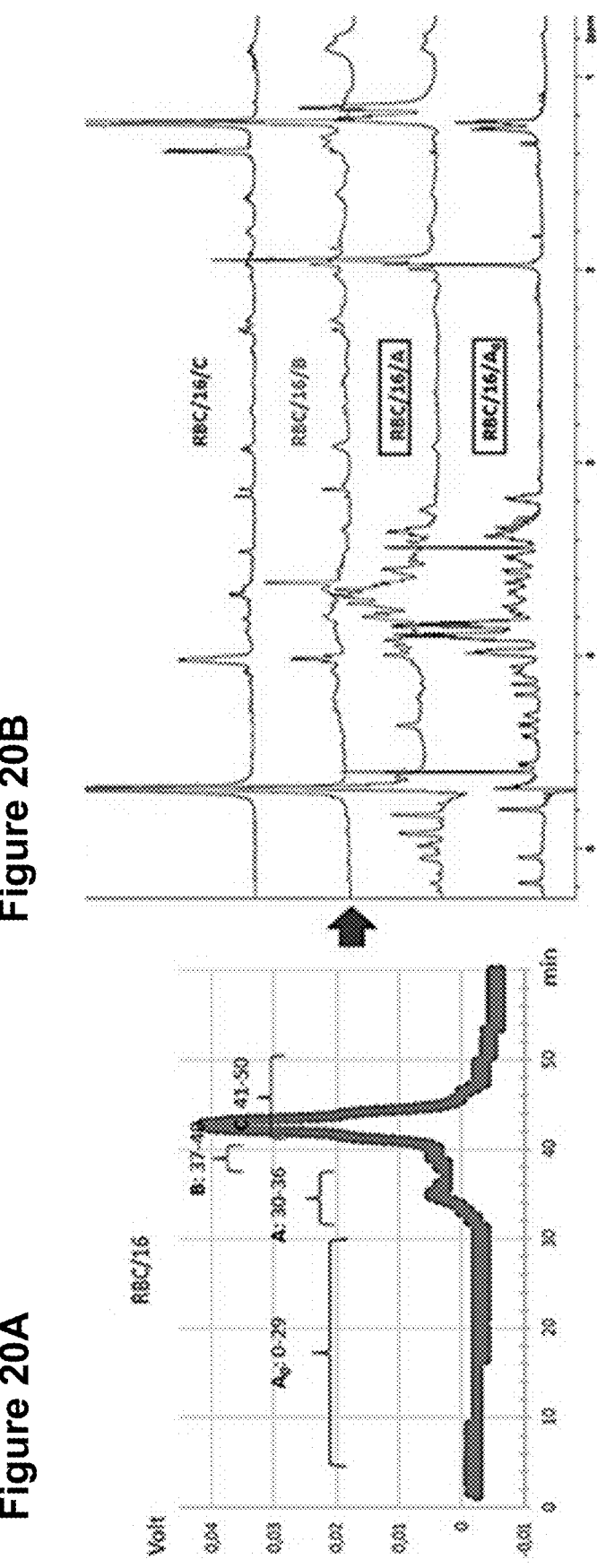
FIGS. 20A-20B show the chromatographic profile observed from size-exclusion chromatography via Sephacryl HR-300 (FIG. 20A) of *L. paracasei* NPB01 polysaccharides and the NMR proton spectra (600 MHZ, 298 K, $D_2O$) of the fractions obtained after purification on Sephacryl HR-300 (FIG. 20B).
Figure 23:
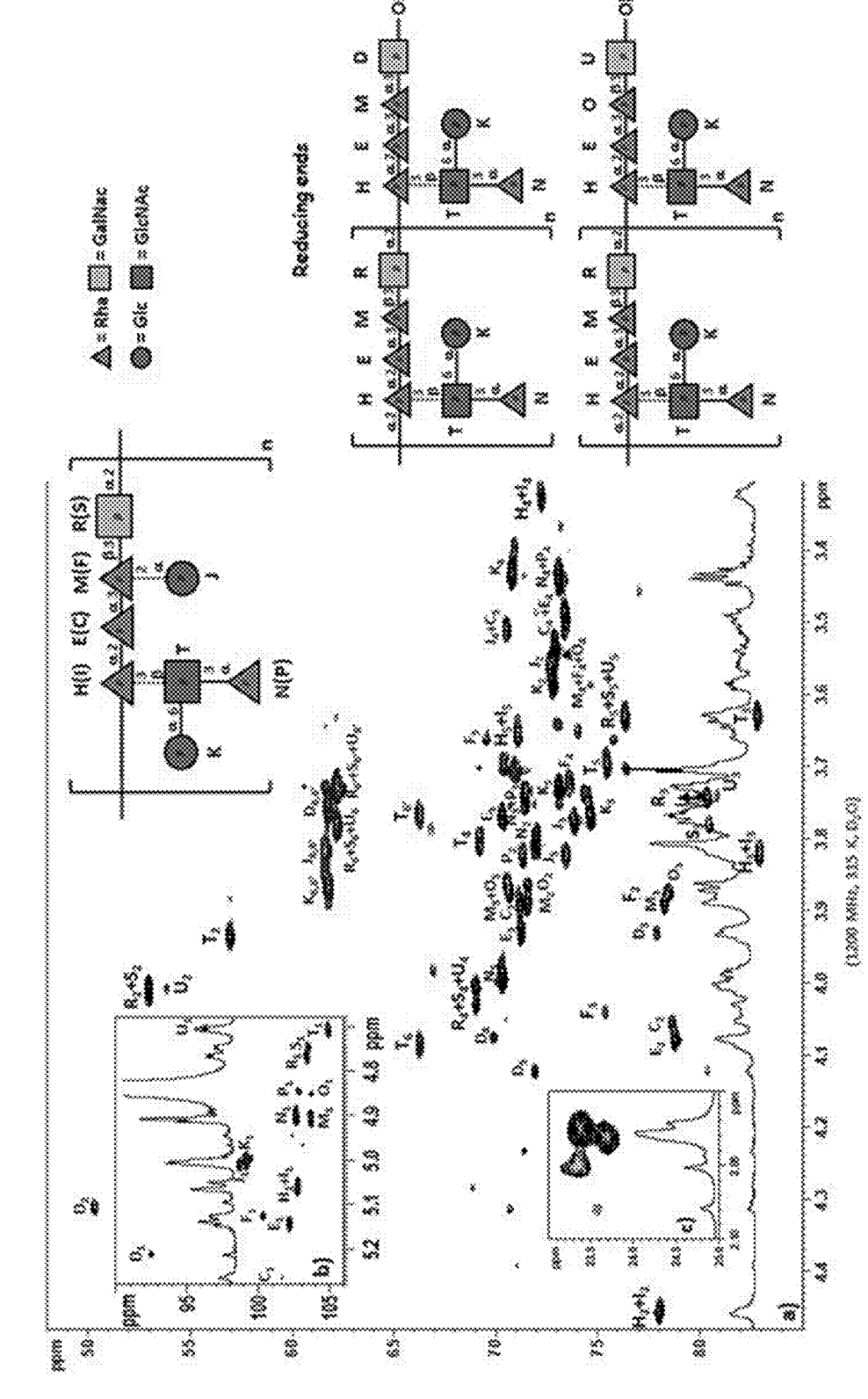
FIG. 23 shows the ring proton region of the HSQC spectrum (1200 MHZ, 293 K, $D_2O$) of the CPS-2 isolated from *L. paracasei* NPB01 along with the proton NMR profile. Letters refer to the carbohydrate residues as reported in the figure and drawn according to the SNFG. Arabic numerals refer to the proton/carbon atoms of the respective residue. In particular, when the substituent "J" is present and the dimer K6→IT is absent, residues are called with the capital letters between brackets.

For CPS-2, by combining the information of $^{13}$C HSQC and $^1$H NMR spectra (FIG. 23), it was possible to distinguish and identify fifteen major anomeric signals between 5.3-4.6 ppm, a crowded ring proton region (4.5-3.2 ppm), a group of acetyl signals between 2.1-1.9 ppm, and several methyl signals at ca. 1.3 ppm, attributable to the different rhamnose units. The anomeric signals were labeled with capital letters. Additionally, the CPS-2 of *L. paracasei* NPB01 is a small-sized polymer, which is in fact eluted as the most retained in the size-exclusion chromatography (FIG. 20A). Finally, CPS-2 monosaccharide linkages were further confirmed by methylation analysis (De Castro, C. et al., Methods Enzymol. 2010; 480:89-115) which identified the presence of a terminal rhamnose, a 2-substituted, a 3-substituted and a 2,3-substituted rhamnose, of a terminal glucose, a 6-substituted and a 3,6-substituted glucosamine and of a 3-substituted galactosamine. The other unmarked (and small) peaks are impurities.

Cell Viability and Regulation of Immune Response and Epithelial Barrier in Human Enterocytes To determine whether the *L. paracasei* NPB01 postbiotic, CPS-1, CPS-2, or TA were toxic to human enterocytes, cell viability was assessed by performing a trypan blue exclusion assay for 2 h with cells incubated with CPS-1, CPS-2, or TA up to the concentration of 1000 µg/ml for 48 hours. None of these compounds were found to be cytotoxic to Caco-2 cells. Since no cytotoxic effects were recorded at the highest dose (1000 µg/ml), the concentration was deemed safe for studying the biological action of these compounds in human enterocytes.

The *L. paracasei* NPB01 postbiotic was able to stimulate the expression of LL-37 and occludin in human enterocytes. Similarly, purified CPS-2 was able to upregulate the expression of both biomarkers in human cells. Purified CPS-1 and TA were each able to only modulate occludin expression. Dose response experiments revealed that 1 µg/ml *L. para-*

*casei* NPB01 postbiotic and 10 µg/ml CPS-2 were effective doses for the regulation of LL-37 expression. For the regulation of occludin expression, 10 µg/ml *L. paracasei* NPB01 postbiotic, 100 µg/ml CPS-1, 1 µg/ml CPS-2, and 10 µg/ml TA were found to be effective doses.

Figures 24A, 24B:
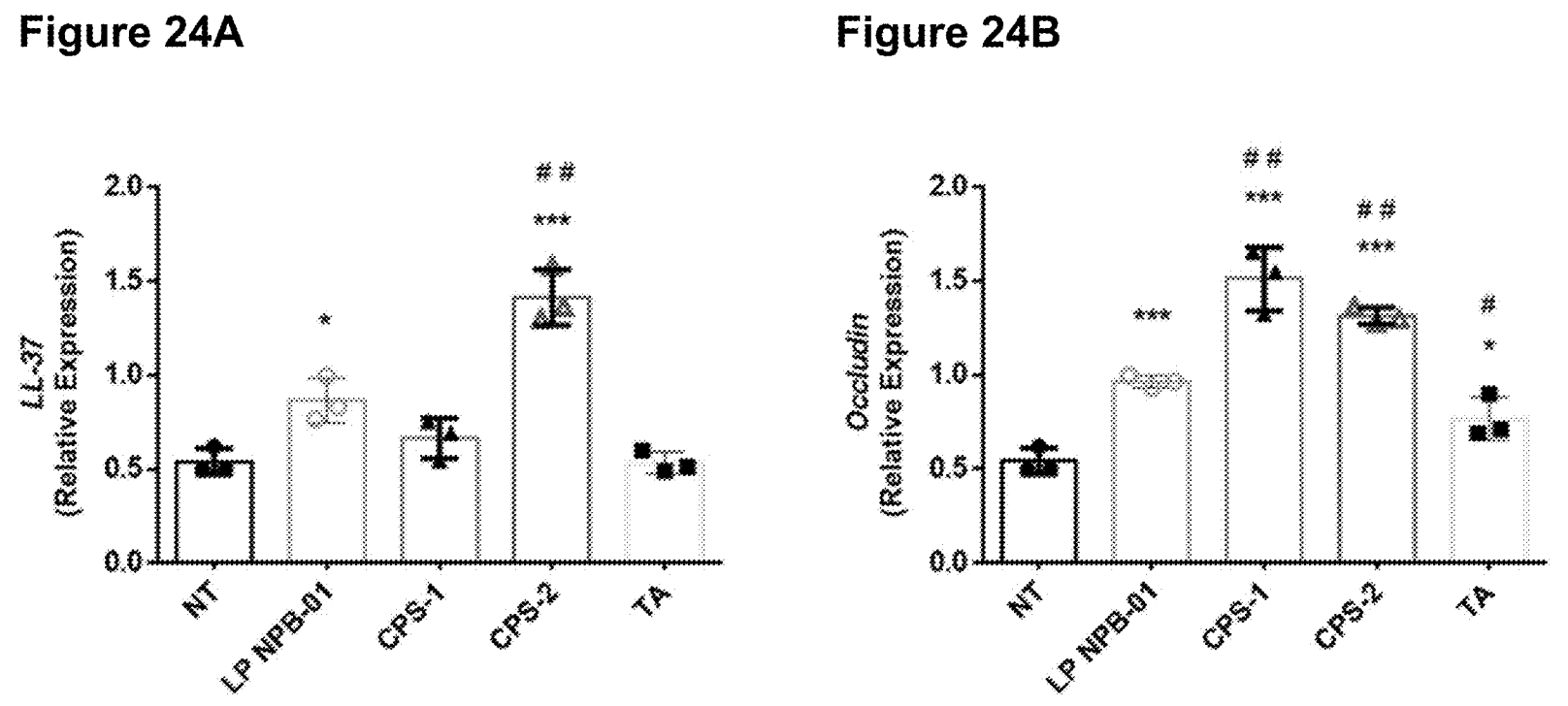

FIGS. 24A-24B show the effects elicited by the higher effective doses of *L. paracasei* NPB01 postbiotic, CPS-1, CPS-2, and TA. The effects were higher after stimulation with CPS-2 for both LL-37 and Occludin. The effects were higher after stimulation with CPS-1 for occludin expression compared to stimulation with TA.

These results indicate that *L. paracasei* NPB01 postbiotic, and the *L. paracasei* NPB01-derived polysaccharides TA, CPS-1, and CPS-2, can exert a beneficial action on immune response and gut barrier biomarkers in human enterocytes. These effects resemble those reported for another *L. paracasei* strain (i.e., CBAL74) (Paparo L. et al., Benef. Microbes. 2018; 9(1):165-172), suggesting that different *L. paracasei* strains could exert a similar beneficial action on human cell functions.

Example 5: Postbiotic Modulation of the Human Gut Microbiome

The effects of the direct interaction between postbiotics and microbes of the human gut microbiome are still largely unexplored. *B. velenzensis* MV4 and *P. megaterium* MV30 are two *bacillus* strains belonging to the Firmicutes phyla, recently isolated from healthy gut microbiome (Vittoria M. et al., Microorganisms. 2023; 11(8):1978). These two microorganisms exert a role in protecting the host against infections, oxidative stress, and inflammation. In addition, these microbes contribute to the optimal production of short chain fatty acids in the gut lumen. The short chain fatty acids, and in particular butyrate, are responsible for the regulation of a myriad of beneficial actions on human health at the intestinal and extraintestinal level (De Filippis F. et al., Nature Comm. 2021; 12(1):1-11). In particular, at the intestinal level, butyrate can improve ion absorption, cell proliferation, cell differentiation, intestinal barrier function, immune-regulation, oxidative stress, intestinal motility, visceral perception, and rectal compliance; and, at the extraintestinal level, butyrate can improve insulin sensitivity, cholesterol synthesis, energy expenditure, ammonia scavenging, stimulation of β-oxidation of very long chain fatty acids, stimulation of peroxisome proliferation, cystic transmembrane conductance regulator (CFTR) functioning, neurogenesis, and fetal hemoglobin (HbF) production (Canani, R. B., et al., World J Gastroenterol 2011; 17(12):1519-1528).

In this study, the ability of two different postbiotic products to modulate the growth of *B. velenzensis* MV4 and *P. megaterium* MV30 was evaluated.

Methods

Strains and Pre-Culture

*P. megaterium* MV30 and *B. velenzensis* MV4 were cultured overnight at 37° C. in the minimal microbial growth medium M9 (Sigma Aldrich St. Louis, MA, USA). After pre-culture, the optical density at 600 nm was measured using a spectrophotometer. The samples were then diluted with M9 broth to achieve an optical density of 0.1 in each well of a multi-well plate, which was the chosen absorbance value prior to initiating stimulation with the postbiotic product.

Postbiotic Products

Two different postbiotic products were evaluated. The first product (LP6h:LGG24 h) was obtained through two sequential fermentations carried out in MRS broth (Sigma Aldrich). In the first fermentation, MRS broth was inoculated with *Lacticaseibacillus paracasei* NPB01 (LP) and left to ferment for 6 hours at 37° C. After heat inactivation, the same broth was inoculated with *Lactobacillus rhamnosus* GG (LGG) and left to ferment for 24 hours at 37° C. The second fermentation was followed by heat inactivation and spray-drying to obtain a dried postbiotic product (LP6h: LGG24 h).

The second postbiotic product was obtained through two separate fermentation processes: a first MRS broth was fermented by *L. paracasei* NPB01, and in parallel, a second fermentation was carried out by *L. rhamnosus* GG. In both cases, the fermentation lasted 24 hours at 37° C. At the end of the fermentation, heat inactivation and spray-drying resulted in the production of two separate dried postbiotic products. These powders were then mixed in a 80:20 ratio of LP:LGG.

Stimulation with the Postbiotic Products
Results

Figures 25A, 25B:
FIGS. 25A-25B show the effects of 6-hour postbiotic stimulation on the OD600 absorbances of *P. megaterium* MV30 (FIG. 25A) and *B. velenzensis* MV4 (FIG. 25B).

*P. megaterium* MV30 and *B. velenzensis* MV4 were stimulated for 6 h with each postbiotic product and the absorbances were read at 600 nm. As shown in FIGS. 25A-25B, the presence of each postbiotic product promoted a nearly 300% increase in the OD600 for *P. megaterium* MV30 (FIG. 25A), and a close to 150% increase for *B. velenzensis* MV4 (FIG. 25B) compared to the control. These results indicate that the postbiotic products generated using the methods described herein result in a significant increase in two species of intestinal microbiota.

Example 6: Effects of Postbiotic Products on Human Intestinal Epithelium Cells Methods
Postbiotic Products Tested Postbiotics that were tested in this study were generated from the following microorganisms: 1) *L. paracasei* NPB01 (LP); 2) *L. rhamnosus* GG (LGG); 3) LP:LGG (50:50), derived from parallel fermentation; 4) LP:LGG (80:20) derived from parallel fermentation; 5) LP 6 h+LGG 24 h derived from serial fermentation; and 6) LGG 6 h+LP 24 h derived from serial fermentation. Each of the products was derived from a fermentation in MRS and subsequent inactivation at 85° C. for 20 seconds.

Cellular Model

The effects of postbiotic products generated using the methods described herein were tested on human intestinal epithelium Caco-2 cells in monolayer (American Type Culture Collection, Middlesex, UK; accession number: HTB-37).

Cells were grown in Dulbecco's modified Eagle's medium (DMEM; Gibco, Berlin, Germany) with a high glucose concentration (4.5 g/L) and L-glutamine, supplemented with 10% fetal bovine serum (FBS, Gibco), 1% non-essential amino acids (Gibco), 1% sodium pyruvate (Gibco), 1% penicillin/streptomycin (Gibco). Cells were incubated at 37° C. in a humidified atmosphere containing 5% $CO_2$. The culture medium was changed every 2 days.

Human Enterocytes Stimulation Protocol

Caco-2 cells were stimulated 15 days post-confluence.

Cells exposed to only medium were used as negative control (NT). Afterward, the supernatants were harvested and stored at −20° C. Total RNA was extracted from stimulated and untreated cells with TRIzol reagent (Gibco BRL, Paisley, UK) and stored at −20° C. for further use.

Cell Proliferation Assay

Human enterocyte proliferation assays were assessed using MTT (the bromide salt of 3-(4,5-dimethylthiazol-2-yl)-2,5-diphenyl tetrazolium) (Sigma-Aldrich, Milan, Italy).

Cells ($10^4$ cells/well) were seeded in 24-well plates (Corning, Inc., New York, NY, USA) with or without the postbiotics at different doses (0.115-575 mg/ml) for 48 h at 37° C. in a 5% $CO_2$ incubator. NFM served as the control.

The cell viability was monitored by adding 5 mg/ml of MTT solution followed by 1 h incubation. The medium was then removed, and the converted dye was solubilised with acidic isopropanol (0.04-0.1 N HCl in absolute isopropanol). Absorbance was read at 570 nm using an Epoch Microplate Spectrophotometer (Bioteck, Winooski, VT, USA).

Quantitative Real-Time PCR

Total cellular RNA was extracted from cells with TRIzol reagent (Gibco BRL, Paisley, UK). RNA (1 μg) was reverse transcribed at 37° C. in cDNA with a High-Capacity RNA-to-cDNA™ Kit (Life Technologies, Waltham, MA, USA) according to the manufacturer's instructions. Complementary DNA (cDNA) was stored at −20° C. until use. Quantitative real-time PCR (qRT-PCR) analysis was performed to determine gene expression. After a hot start, the amplification protocol was 40 cycles of 30 s of denaturation at 95° C., 30 s of annealing at 60° C., and 1 min of elongation at 72° C. in a Light Cycler 7900HT (Applied Biosystems, Grand Island, NY, USA). The quantitative gene expression was calculated with the comparative Ct method and normalised against the Ct of glucuronidase (GUS) messenger.

Assessment of Innate Immunity Peptide Cathelicidin LL-37 by ELISA

The concentrations of LL-37 in cell supernatants were measured using specific human ELISA assay kits (Elabscience Biotechnology Inc. Wuhan, Hubei), with a detection limit of 1.56 ng/ml. The ELISAs were conducted according to the manufacturer's recommendations.

Statistical Analysis

The Kolmogorov-Smirnov test was used to determine whether variables were normally distributed. Data were analysed using unpaired t-test. The level of significance for all statistical tests was two-sided, $p < 0.05$. All data were collected in a dedicated database and analysed by a statistician using GraphPad Prism 9.3.0 (La Jolla, CA USA).

Results

The direct interaction between postbiotics and human enterocytes resulted in several beneficial effects for human health, as demonstrated in the effects seen on the human enterocyte cells. The effects of the postbiotic compositions were found to be dose-dependent. The best effective dose of postbiotic across all experimental conditions was 11.5 mg/ml.

Figure 26B:
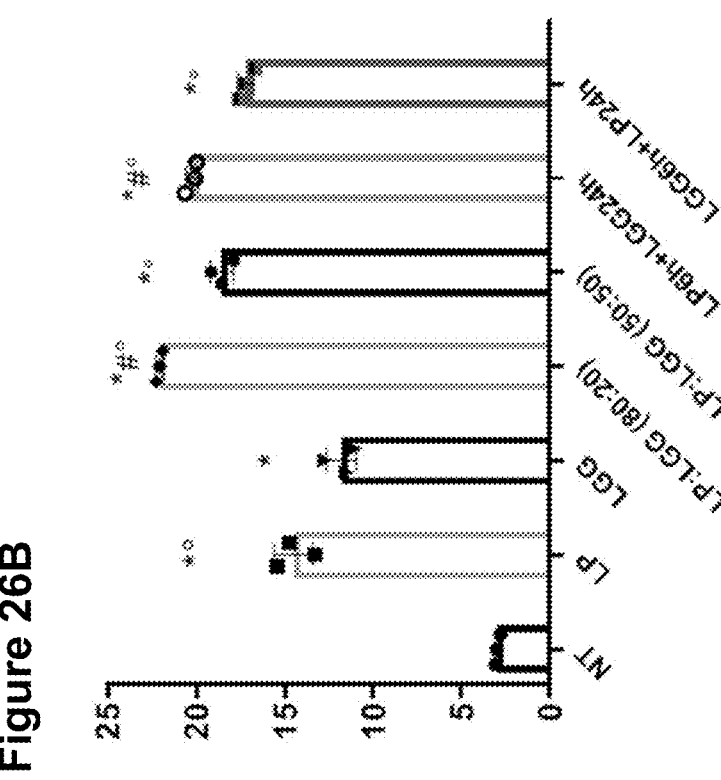
FIGS. 26A-26B show the effects of the direct interaction between postbiotics and human enterocytes (Caco-2 cells) on cell growth (expressed as percent of cell density) assessed by MTT assay (FIG. 26A) and on cell differentiation measured by lactase expression using RT-PCR (FIG. 26B). Data represent the mean (±standard deviation represented by vertical bars) of three independent experiments, each performed in duplicate. *p<0.05 vs NT, #p<0.05 vs LP, °p<0.05 vs LGG.
Figure 26A:
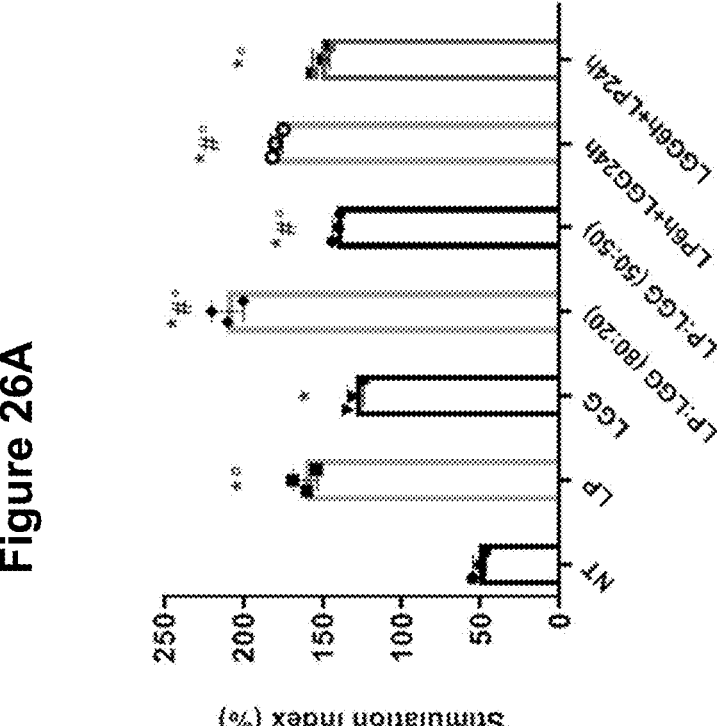

The effects of the direct interaction between postbiotics and human enterocytes on cell growth and differentiation (measured by the result of lactase expression) are depicted in FIGS. 26A-26B.

Figure 27B:
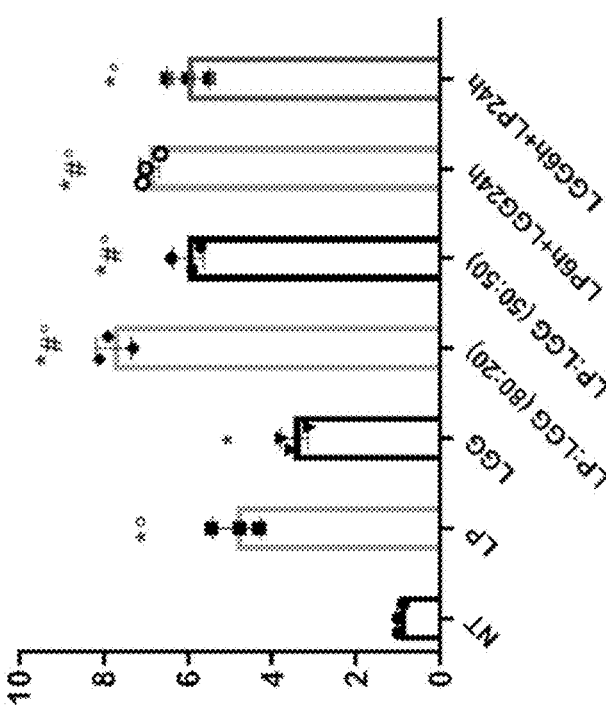
FIGS. 27A-27B show the effects of the direct interaction between postbiotics and human enterocytes (Caco-2 cells) on the tight-junction proteins occludin (FIG. 27A) and zonula occludens-1 (ZO-1) (FIG. 27B). Data represent the mean (±standard deviation represented by vertical bars) of three independent experiments, each performed in duplicate. *p<0.05 vs NT, #p<0.05 vs LP, °p<0.05 vs LGG.
Figure 27A:
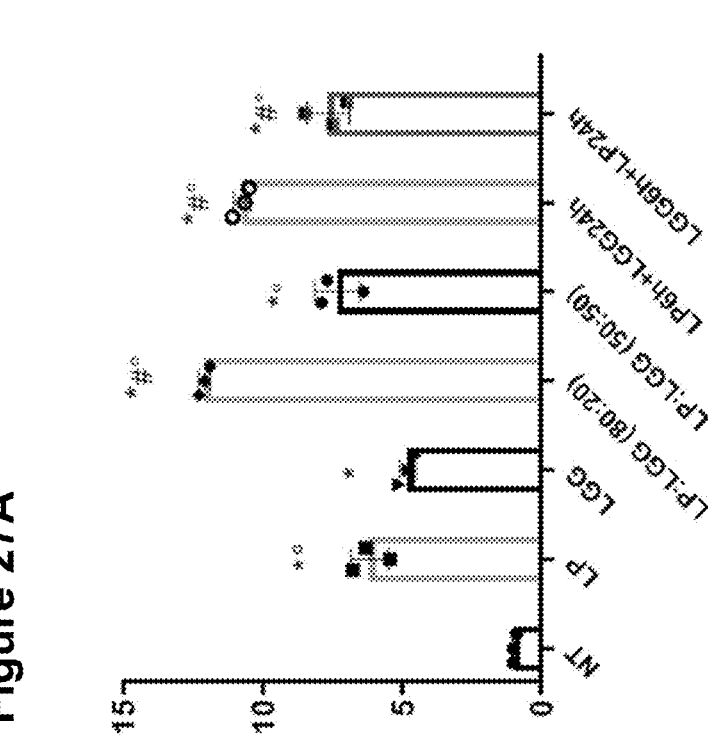

The effect on human enterocytes monolayer permeability is reported in FIGS. 27A-27B. The positive modulation of intestinal permeability was confirmed by the up-regulation of tight junction (TJ) proteins expression, namely, occludin and zonula occludens 1 (ZO-1), observed after stimulation with postbiotics. No effect was observed in unstimulated cells (NT).

Figure 28:
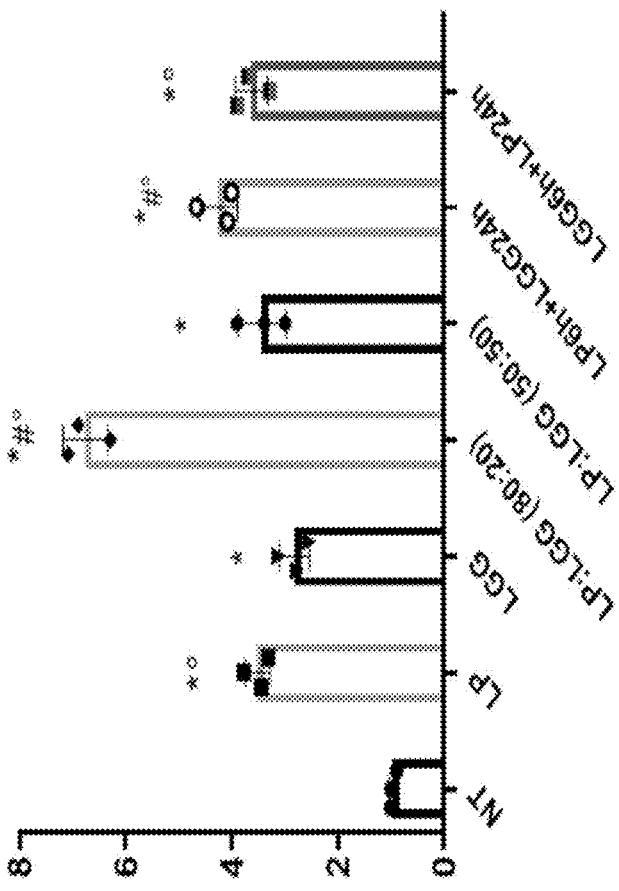
FIG. 28 shows the effect of the direct interaction between postbiotics and human enterocytes (Caco-2 cells) on mucus (MUC2) production. Data represent the mean (±standard deviation represented by vertical bars) of three independent experiments, each performed in duplicate. *p<0.05 vs NT, #p<0.05 vs LP, °p<0.05 vs LGG.

The postbiotics were also able to up-regulate MUC2 expression (FIG. 28).

Figure 29:
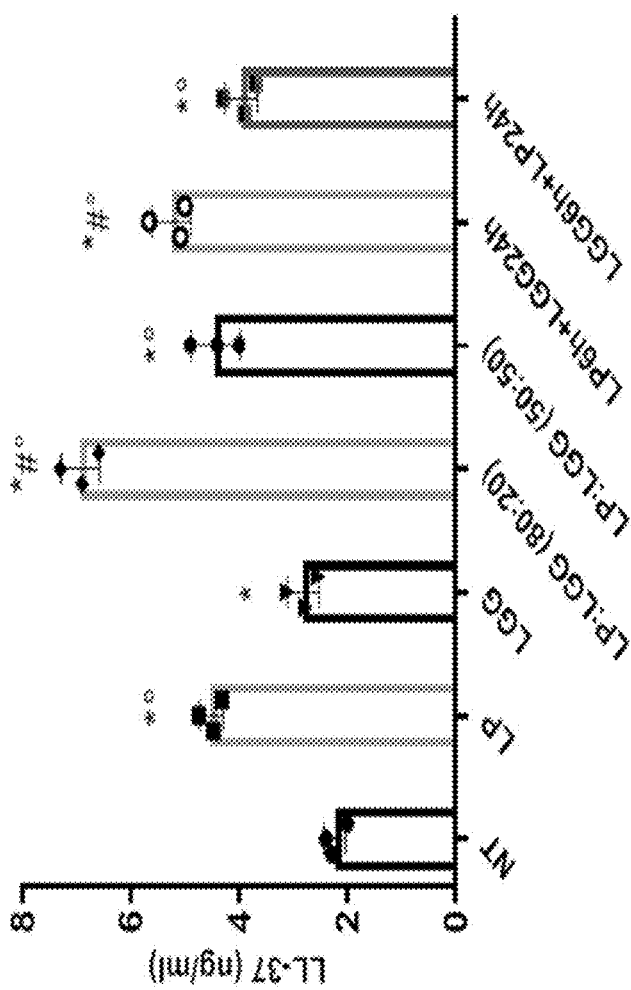
FIG. 29 shows the effect of the direct interaction between postbiotics and human enterocytes (Caco-2 cells) on stimulation of innate immunity peptide cathelicidin LL-37. The LL-37 production was assessed in cell supernatants by ELISA. Data represent the mean (±standard deviation represented by vertical bars) of three independent experiments, each performed in duplicate. *p<0.05 vs NT, #p<0.05 vs LP, °p<0.05 vs LGG.

As shown in FIG. 29, postbiotics elicited a significant increase of chatelicidin LL-37 production by human enterocytes.

Example 7: Additional Effects of Postbiotic
Products on Human Intestinal Epithelium Cells

Rationale

Serial fermentation was used to combine and reproduce four microorganisms: *L. paracasei* NPB-01 (LP), *B. animalis* subsp. *lactis* (Bal), *A. muciniphila* (Akk), and *E. coli* Nissle 1917 (Ecn)—members of four respective main phylas present in the resident intestinal microbiota: Firmicutes, Actinobacteria, Verrucomicrobia, and Proteobacteria.

Materials and Methods

Materials

LP was provided by Science Power S.r.l.; Bal was isolated from commercial food supplement, OptiBac Bifido & Fibre; Akk was isolated from the feces of healthy children; and Ecn was isolated from commercial food supplement, EcN Integratore Alimentare.

Single Fermentation Conditions

Media & Fermentation: 24-hour, single fermentations were performed for each microorganism: LP and Bal were grown on MRS broth for 24 hours and subsequently inactivated by a mild heat treatment; Akk was grown on BHI broth supplemented with porcin mucin for 24 hours and then inactivated by a mild heat treatment; Ecn was grown on LB broth for 24 hours and then inactivated by a mild heat treatment.

Bacterial Growth: Bacterial growth, in CFU/mL, was measured after single fermentation.

Drying: The resultant single-strain postbiotic composition was dried via spray-drying for use in subsequent biological assays.

Serial Fermentation Conditions

Media: To facilitate suitable growth of all microorganisms, the fermentation medium comprised: 34% MRS, 33% BHI supplemented with porcin mucin, and 33% LB broth.

Fermentation: First, LP was fermented in the fermentation medium for 6 hours before a mild heat treatment was applied to inactivate the fermentation broth. Bal was subsequently added to the fermentation broth and fermented for 6 hours before a mild heat treatment was applied to inactivate the fermentation broth. Akk was subsequently added to the fermentation broth and fermented for 12 hours before a mild heat treatment was applied to inactivate the fermentation broth. Last, Ecn was subsequently added to the fermentation broth and fermented for 12 hours before a mild heat treatment was applied to inactivate the fermentation broth.

Bacterial Growth: Bacterial growth, in CFU/mL, was measured after each serial fermentation step.

Drying: The resultant multi-strain postbiotic composition was dried via spray-drying for use in subsequent biological assays.

Biological Evaluation: Caco-2 cells were cultured, as described in Example 4 above, and then stimulated, as described in Example 4 above, with postbiotic compositions obtained from (i) single fermentation (of LP, Bal, Akk and Ecn) and (ii) serial fermentation (of LP+Bal+Akk+Ecn). ZO-1, Occludin, and MUC-5 expression was measured.

Results

Bacterial growth of LP reached $5 \times 10^8$ CFU/mL after single fermentation of LP; bacterial growth of Bal reached $7 \times 10^8$ CFU/mL after single fermentation of Bal; bacterial growth of Akk reached $3.1 \times 10^8$ CFU/mL after single fermentation of Akk; and bacterial growth of Ecn reached $1.2 \times 10^9$ CFU/mL after single fermentation of Ecn.

Figure 30:
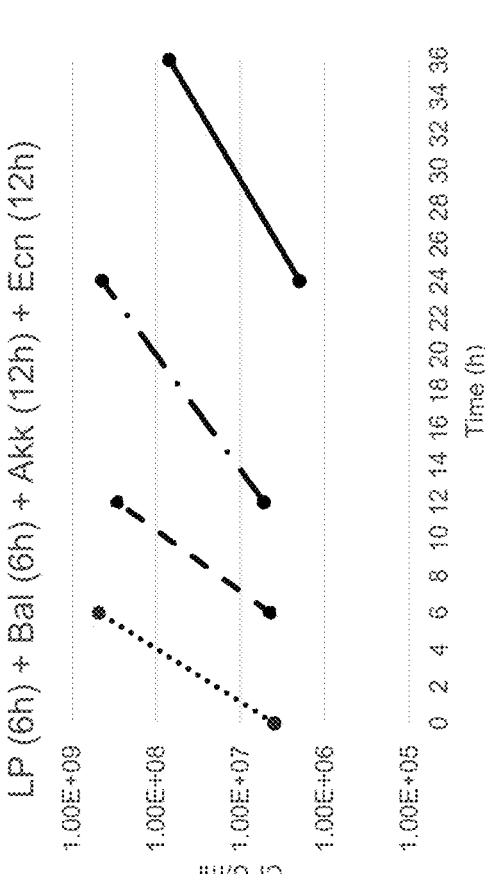
FIG. 30 shows the effect of the serial fermentation process over time (in hours) on microbial growth increase (in CFU/ml). LP, Bal, Akk, and Ecn correspond to *L. paracasei* NPB-01, *B. animalis* subsp. *lactis, A. muciniphila*, and *E. coli* Nissle 1917-respectively.

For the serial fermentation process (FIG. 30): LP showed a microbial growth increase ($\Delta$ log) of 2 log, achieving a bacterial concentration of $4.8 \times 10^8$ CFU/mL after the first 6 hours of fermentation; Bal showed a growth increase ($\Delta$ log) of 2 log, achieving a bacterial load of $2.9 \times 10^8$ CFU/mL after 6 subsequent hours of fermentation; Akk showed a growth increase ($\Delta$ log) of 2 log, achieving a bacterial concentration of $4.4 \times 10^8$ CFU/mL after 12 further subsequent hours of fermentation; and Ecn showed a growth increase ($\Delta$ log) of 1 log, achieving a bacterial load of $7.0 \times 10^7$ CFU/mL after 12 final subsequent hours of fermentation.

For the biological evaluation (FIG. 31A-31C), the LP single-strain postbiotic composition demonstrated the highest increase in occludin, ZO-1, and MUC5AC; however, the multi-strain postbiotic composition (LP+Bal+Akk+Ecn) demonstrated a significantly greater stimulation effect than all single-strain (LP, Bal, Akk, or Ecn) postbiotic compositions.

It is to be appreciated that the Detailed Description section, and not the Summary and Abstract sections, is intended to be used to interpret the claims. The Summary and Abstract sections may set forth one or more but not all exemplary embodiments of the present disclosure as contemplated by the inventor(s), and thus, are not intended to limit the present disclosure and the appended claims in any way.

The foregoing description of the specific embodiments will so fully reveal the general nature of the disclosure that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary embodiments, but should be defined only in accordance with the following claims and their equivalents.

The contents of all cited references (including literature references, U.S. or foreign patents or patent applications, and websites) that are cited throughout this application are hereby expressly incorporated by reference as if written herein in their entireties for any purpose, as are the references cited therein. Where any inconsistencies arise, material literally disclosed herein controls.

While various specific aspects have been illustrated and described, the above specification is not restrictive. It will be appreciated that various changes can be made without departing from the spirit and scope of the invention(s). Many variations will become apparent to those skilled in the art upon review of this specification.

What is claimed is:

1. A method of preparing a postbiotic composition comprising a sequential fermentation process, said sequential fermentation process comprising the steps of:
    (i) inoculating a culture medium with a first fermenting microorganism;

US 12,594,308 B2

45

(ii) fermenting the culture medium under conditions suitable for fermentation by the first fermenting microorganism, thereby obtaining a first fermentation matrix comprising the first fermenting microorganism;

(iii) inactivating the first fermenting microorganism in the first fermentation matrix to obtain a first fermentation product comprising the inactivated first fermenting microorganism and the first fermentation matrix;

(iv) inoculating the first fermentation product of step (iii) with a second fermenting microorganism;

(v) fermenting the first fermentation product under conditions suitable for fermentation by the second fermenting microorganism, thereby obtaining a second fermentation product comprising the second fermenting microorganism and the inactivated first fermenting microorganism;

(vi) inactivating the second fermenting microorganism in the second fermentation product to obtain a postbiotic composition comprising the inactivated first fermenting microorganism and the inactivated second fermenting microorganism, wherein at least one of the fermenting microorganisms is *Lacticaseibacillus paracasei* NPBO1; and optionally, after inactivating the second fermenting microorganism of step (vi), repeating steps (iv) to (vi) one or more times with an additional fermenting microorganism.

2. The method according to claim 1, wherein each fermenting microorganism is a different species from any other fermenting microorganism.

3. The method according to claim 1, wherein each fermenting microorganism is selected from the group consisting of a bacterial microorganism and a yeast microorganism.

4. The method according to claim 3, wherein the bacterial microorganism is selected from the group consisting of a *Lactobacillus* species, a *Lactococcus* species, a *Bifidobacterium* species, a *Lacticaseibacillus* species, a *Streptococcus* species, an *Akkermansia* species, and an *Escherichia* species.

5. The method according to claim 3, wherein the yeast microorganism is selected from a *Saccharomyces* species.

6. The method according to claim 1, wherein each fermenting microorganism is selected from the group consisting of *Lactobacillus paracasei, Lactobacillus rhamnosus, Lactobacillus reuteri, Lactobacillus plantarum, Lactobacillus casei, Lacticaseibacillus paracasei, Bfidobacterium bifidum, Bifidobacterium infantis, Bifidobacterium breve, Bifidobacterium longum, Streptococcus salivarius, Akkermansia muciniphila, Escherichia coli,* and *Saccharomyces boulardii.*

7. The method according to claim 1, further comprising drying the inactivated fermentation product and wherein said dried inactivated fermentation product is optionally rehydrated in water prior to subsequent inoculation with a fermenting microorganism.

8. The method according to claim 1, further comprising the step of drying the postbiotic composition.

9. The method according to claim 1, wherein the culture medium comprises media selected from the group consisting of MRS media, Brain Heart Infusion (BHI) broth, Luria-Bertani (LB) broth, plant-derived media, functional media containing plant extracts with antioxidant, antiviral and/or antibacterial activity, culture media of natural origin, and any combination thereof.

10. The method according to claim 1, wherein the fermentation step is carried out at a temperature from 25° C. to 45° C.

11. The method according to claim 1, wherein inactivation of the fermenting microorganism comprises a procedure selected from the group consisting of heat-inactivation, chemical treatment, gamma or ultraviolet irradiation, high pressure, sonication, and any combination thereof.

12. A method of preparing a postbiotic composition comprising a sequential fermentation process, said sequential fermentation process comprising the steps of:

(i) inoculating a culture medium with a first fermenting microorganism;

(ii) fermenting the culture medium under conditions suitable for fermentation by the first fermenting microorganism, thereby obtaining a first fermentation matrix comprising the first fermenting microorganism;

(iii) inactivating the first fermenting microorganism in the first fermentation matrix to obtain a first fermentation product comprising the whole of the inactivated microbial biomass of the first fermenting microorganism and the first fermentation matrix;

(iv) inoculating the first fermentation product of step (iii) with a second fermenting microorganism;

(v) fermenting the first fermentation product under conditions suitable for fermentation by the second fermenting microorganism, thereby obtaining a second fermentation product comprising the second fermenting microorganism and the whole of the inactivated microbial biomass of the first fermenting microorganism;

(vi) inactivating the second fermenting microorganism in the second fermentation product to obtain a postbiotic composition comprising the whole of the inactivated microbial biomass of the first fermenting microorganism and the whole of the inactivated microbial biomass of the second fermenting microorganism, wherein at least one of the fermenting microorganisms is *Lacticaseibacillus paracasei* NPBO1; and optionally, after inactivating the second fermenting microorganism of step (vi), repeating steps (iv) to (vi) one or more times with an additional fermenting microorganism.

13. The method of claim 1, wherein the fermenting of the culture medium in step (ii) is carried out for a time from 2 hours to 36 hours.

14. The method of claim 13, wherein the fermenting of the culture medium in step (ii) is carried out for a time from 6 hours to 24 hours.

15. The method of claim 1, wherein the fermenting of the first fermentation product in step (v) is carried out for a time from 6 hours to 36 hours.

* * * * *